United States Patent
Katsumata et al.

(10) Patent No.: US 9,448,170 B2
(45) Date of Patent: Sep. 20, 2016

(54) HARMFUL SUBSTANCE EVALUATING METHOD AND HARMFUL SUBSTANCE EVALUATION KIT

(75) Inventors: Masakazu Katsumata, Hamamatsu (JP); Hiroshi Tsuchiya, Hamamatsu (JP); Takashi Koike, Hamamatsu (JP); Masataka Nishikawa, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 266 days.

(21) Appl. No.: 10/583,128

(22) PCT Filed: Dec. 16, 2004

(86) PCT No.: PCT/JP2004/018844
§ 371 (c)(1),
(2), (4) Date: Apr. 12, 2007

(87) PCT Pub. No.: WO2005/062027
PCT Pub. Date: Jul. 7, 2005

(65) Prior Publication Data
US 2007/0224659 A1 Sep. 27, 2007

(30) Foreign Application Priority Data
Dec. 19, 2003 (JP) .................................. 2003-421948

(51) Int. Cl.
*C12Q 1/02* (2006.01)
*C12Q 1/06* (2006.01)
*G01N 21/64* (2006.01)

(52) U.S. Cl.
CPC ................................ *G01N 21/6408* (2013.01)

(58) Field of Classification Search
CPC ...... A01N 25/00; A01N 65/00; A01N 65/03; C02F 1/00; C02F 2209/00; C02F 3/322; C12Q 1/00; C12Q 1/02; G01N 1/00; G01N 21/00; G01N 33/18; G01N 33/1866; G01N 233/405
USPC ......... 435/29, 257.1, 243, 967, 34; 424/405, 424/195.17, 93.1, 9.2
See application file for complete search history.

(56) References Cited

U.S. PATENT DOCUMENTS

| | | | |
|---|---|---|---|
| 5,225,333 A | * | 7/1993 | Krause et al. ................... 435/32 |
| 6,121,053 A | | 9/2000 | Kolber et al. |

(Continued)

FOREIGN PATENT DOCUMENTS

| | | |
|---|---|---|
| DE | 3412023 | 10/1985 |
| DE | 198 57 792 | 7/2000 |

(Continued)

OTHER PUBLICATIONS

Schmidt et al., (Biochimica et Biophysica Acta. 1987. vol. 891:22-27).*

(Continued)

*Primary Examiner* — Gary Nickol
*Assistant Examiner* — Mary Lyons
(74) *Attorney, Agent, or Firm* — Drinker Biddle & Reath LLP

(57) ABSTRACT

A biological growth inhibition factor assay method includes: a first step of mixing a photosynthetic sample, with an aqueous solution sample to prepare a test measurement solution, letting the test measurement solution stand, and then after illuminating light onto the test measurement solution for a predetermined illumination time, measuring the light amount of the delayed fluorescence that is emitted; a second step of mixing the photosynthetic sample with a standard sample, in which biological growth inhibition factors are not present, to prepare a standard measurement solution, letting the standard measurement solution stand, and then after illuminating light onto the standard measurement solution for a predetermined illumination time, measuring the light amount of the delayed fluorescence that is emitted; and a third step of computing assay values based on the light amounts of delayed fluorescence, respectively measured in the first step and the second step, and determining a comparison value of the assay values to assay biological growth inhibition factors. A biological growth inhibition factor assay method that enables analysis of a wide range of inhibition factors in a short time is thereby realized.

9 Claims, 40 Drawing Sheets

(56) References Cited

U.S. PATENT DOCUMENTS

| | | | |
|---|---|---|---|
| 6,365,129 B1 | 4/2002 | Fogarty | |
| 6,569,384 B2 | 5/2003 | Greenbaum et al. | |
| 7,704,731 B2 | 4/2010 | Bjorndal et al. | |
| 8,658,392 B2* | 2/2014 | Katsumata et al. | 435/34 |
| 2002/0102629 A1 | 8/2002 | Greenbaum et al. | |
| 2010/0159496 A1* | 6/2010 | Katsumata et al. | 435/29 |

FOREIGN PATENT DOCUMENTS

| | | |
|---|---|---|
| DE | 199 10 436 | 10/2000 |
| EP | 1 089 068 | 4/2001 |
| JP | 61-133842 | 6/1986 |
| JP | 2000002659 | 1/2000 |
| JP | 2000214089 | 8/2000 |
| JP | 2004-101196 | 4/2004 |
| JP | 2004109012 | 4/2004 |
| JP | 2004533853 | 11/2004 |
| SU | 950682 | 8/1982 |
| WO | WO 03/006684 | 1/2003 |

OTHER PUBLICATIONS

Wrobel et al., (J. of Fluorescence. 1998. vol. 8, No. 3:191-198).*

Zhihui et al. 2000 (Toxicity of Triphenyltin to Spirulina subsalsa; Bull. Environ. Contam. Toxicol. 64:723-728).*

Burger et al. 1988 (Long term delayed luminescence: A possible fast and convenient assay for nutrition deficiencies and environmental pollution damages in plants; Plant and Soil 109:79-83).*

Krause et al. 1984 (Application of Delayed Fluorescence of Phytoplankton in Limnology and Oceanography; J of Luminescence 31 & 32: 888-891).*

Gerhardt et al. 1984 (Delayed Fluorescence in Algae; J of Luminescence 31 & 32 895-898).*

Tonnina et al. 2002 (Integral Toxicity Test of Sea Waters by an Algal Biosensor; Annali de Chimica; 92: 477-484).*

Scordino et al. 1996 (Influence of the presence of atrazine in water on the in-vivo delayed luminescence of Acetabularia acetabulum; J Photochem Photobio, 32:11-17).*

Van Wijk et al. 1999 (Simultaneous measurements of delayed luminescence and chloroplast organization in Acetabularia acetabulum; J Photochem Photobiol B:Biol 49:142-149).*

Wraight et al. 1971 (Delayed fluorescence and the high energy state of chloroplasts; Eur. J. Biochem 19: 386-397).*

Katsumata et al. 2008 (New feature of delayed luminescence: Preillumination-induced concavity and convexity in delayed luminescence decay curve in the green alga Pseudokirchneriella subcapitata; J of Photochem Photobio B 90: 152-162.*

A. Scordino et al. "Influence of the presence of atrazine in water on the in-vivo delayed luminescence of Acetabularia acetabulum," Journal of Photochemistry and Photobiology B: Biology, Jan. 1, 1996, vol. 32, No. 1-2, pp. 11-17, XP55039761.

T. Gunnlaugsson et al. "Delayed lanthanide luminescence sensing of aromatic carboxylates using heptadentate triamide Tb(III) cyclen complexes: The recognition of salicylic acid in water," Chemical Communications, Jan. 1, 2002, No. 18, pp. 2134-2135, XP55038834.

Christoffers, D. et al., "The In-Vivo Fluorescence of Chlorella Fusca as a Biological Test for the Inhibition of Photosynthesis," Toxicological and Environmental Chemistry, vol. 7, 1983, pp. 61-71.

Schreiber et al., "New type of dual-channel PAM chlorophyll fluorometer for highly sensitive water toxicity biotests," Photosynthesis Research 74: 317-330, 2002.

Schmidt et al., "Long-term delayed luminescence in Scenedesmus obliquus. II. Influence of exogeneous factors," Biochimica et Biophysica Acta 891 (1987) 22-27.

Drinovec et al., "Delayed Fluorescence of Lemna minor: A Biomarker of the Effects of Copper, Cadmium, and Zinc," Bull Environ Contain Toxicol. May 2004; 72(5): 896-902.

Barger et al., "Long term delayed luminescence: A possible fast and convenient assay for nutrition deficiencies and environmental pollution damages in plants," Plant and Soil 109, 79-83 (1988).

Gerhardt et al., "Delayed Fluorescence of Algae," Journal of Luminescence 31 & 32 (1984) 895-898.

* cited by examiner

Fig.6
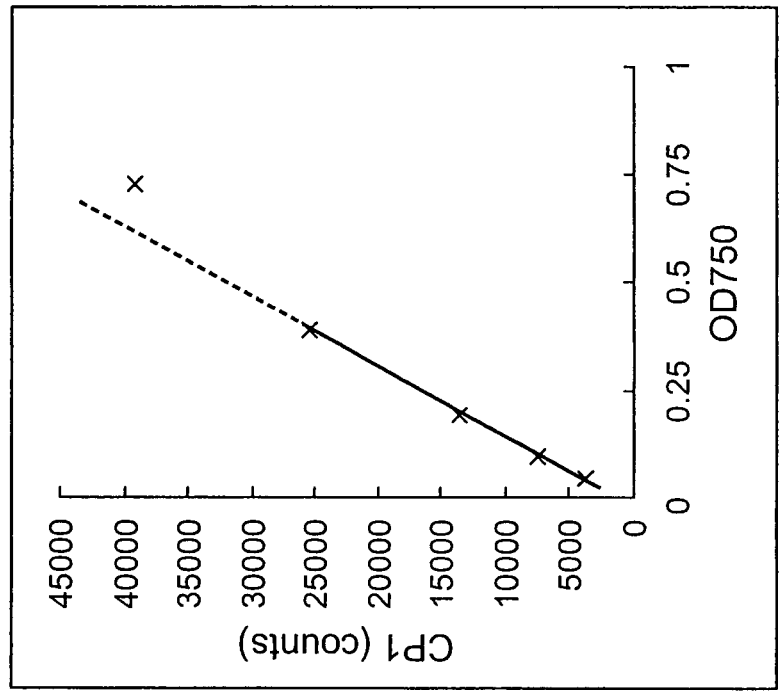
(b)
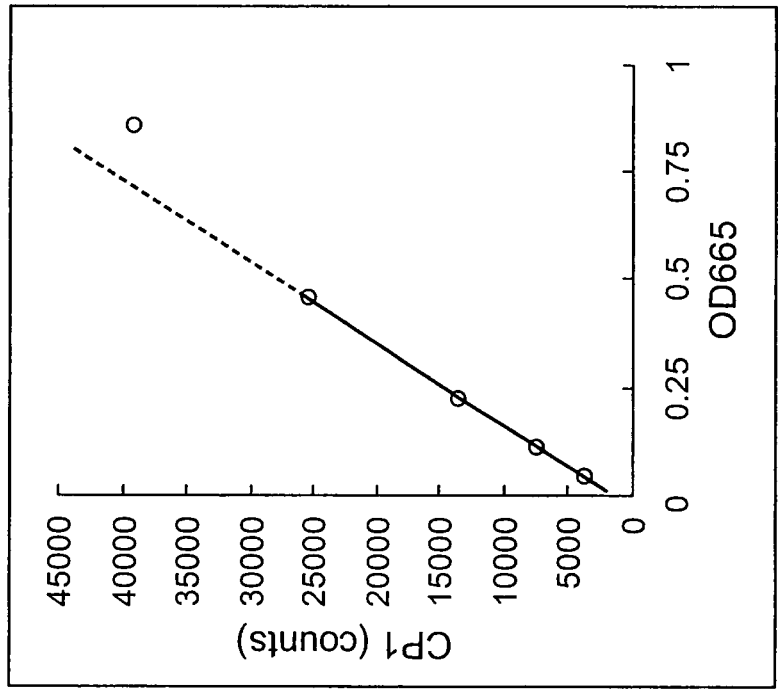
(a)

Fig.8
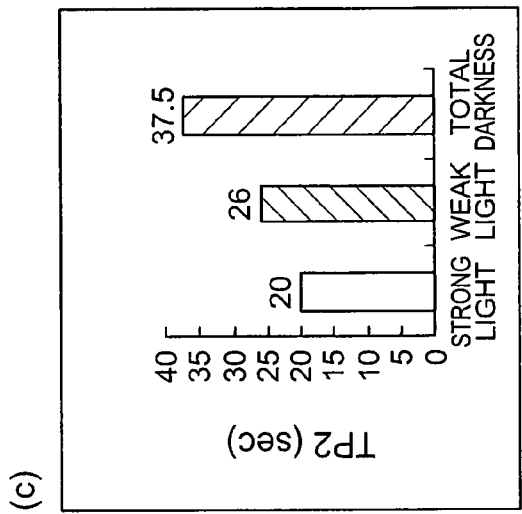
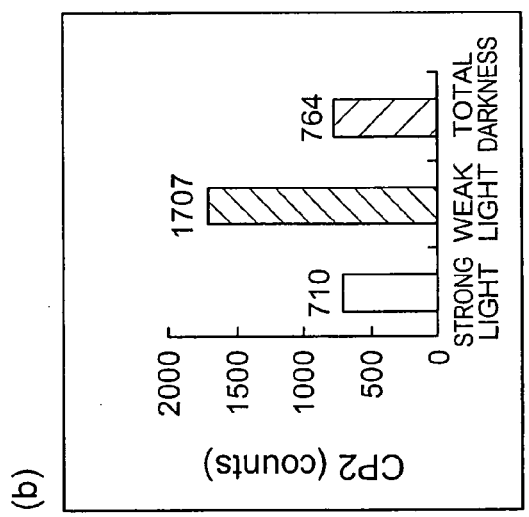
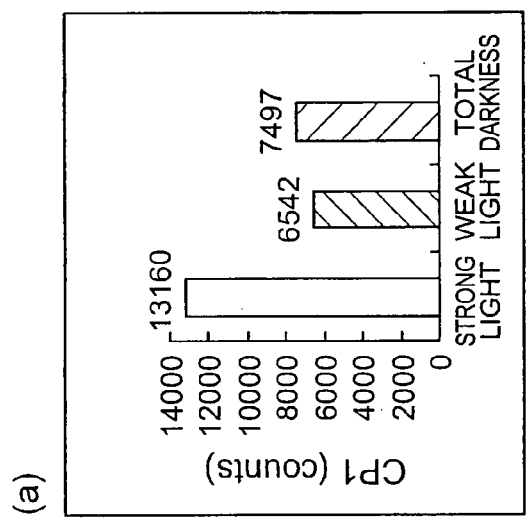

*Fig.22*
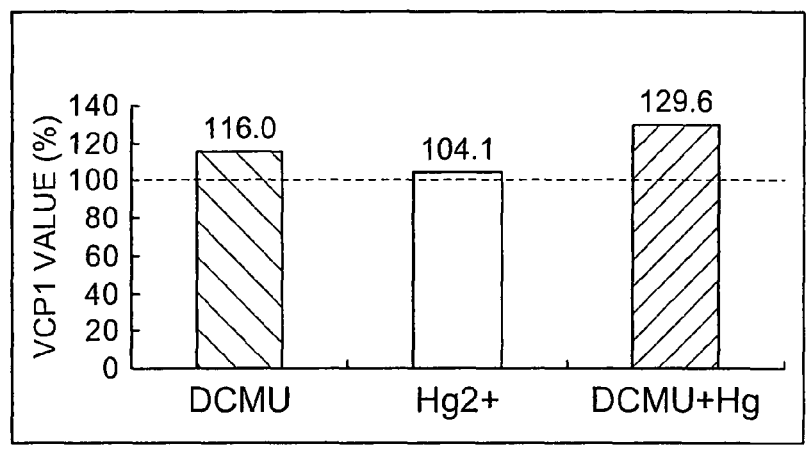
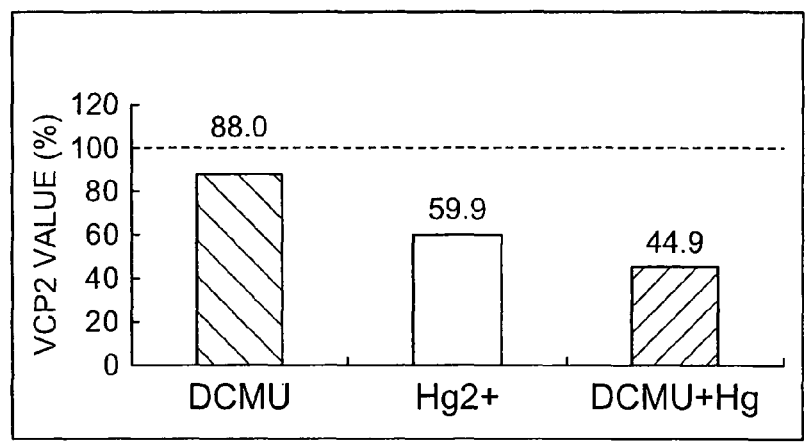
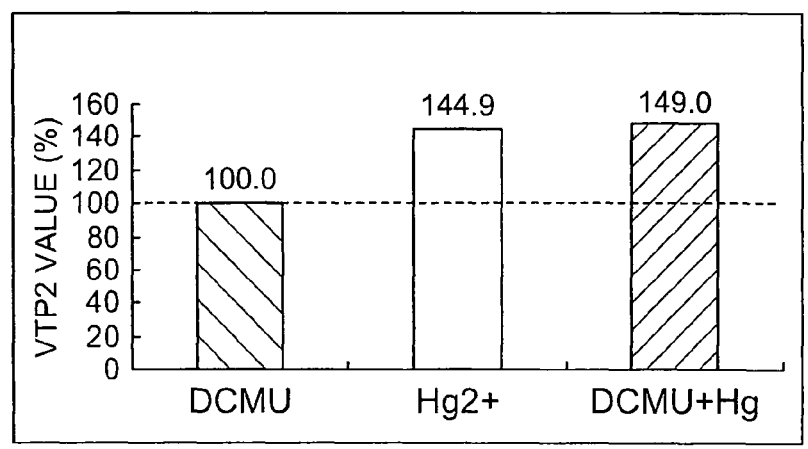

*Fig.23*
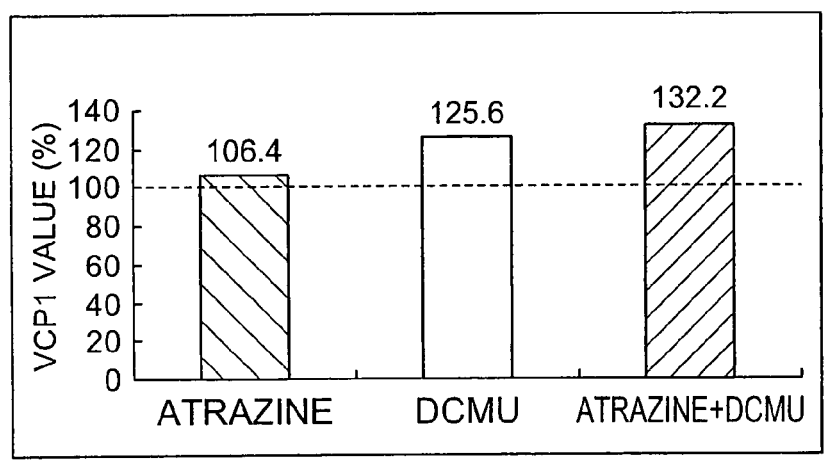
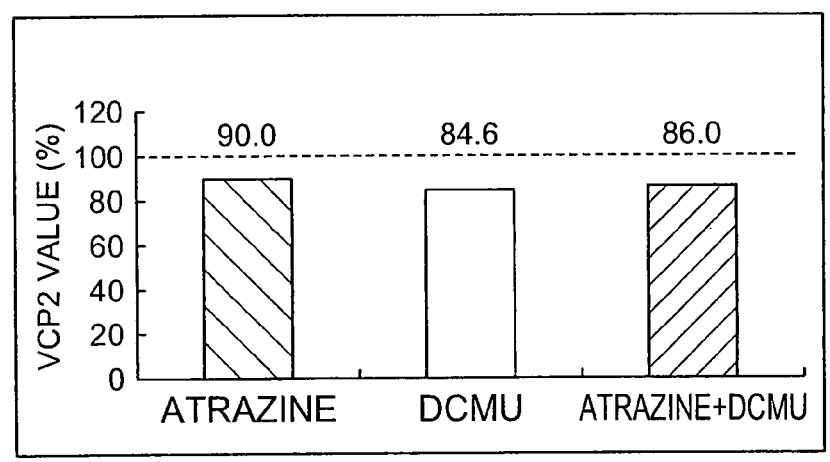
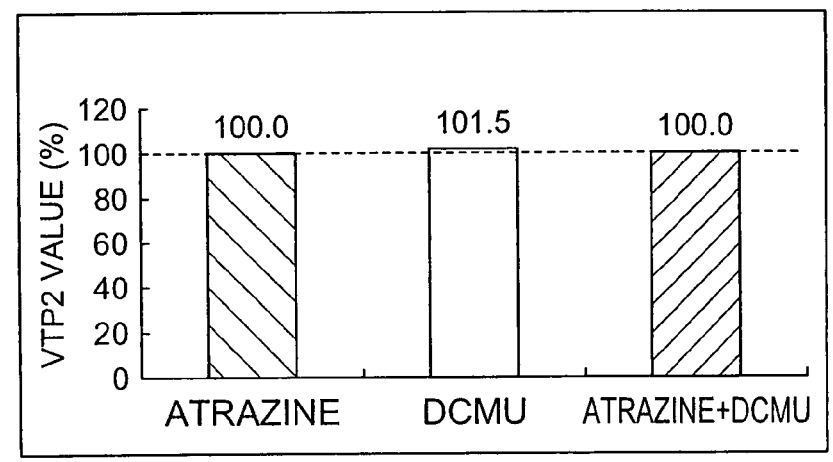

Fig.27
(a)
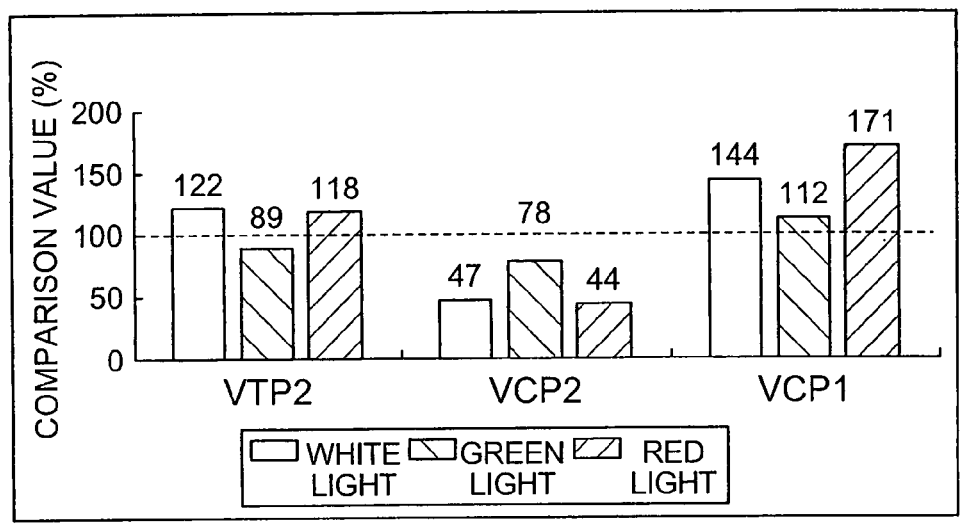
(b)
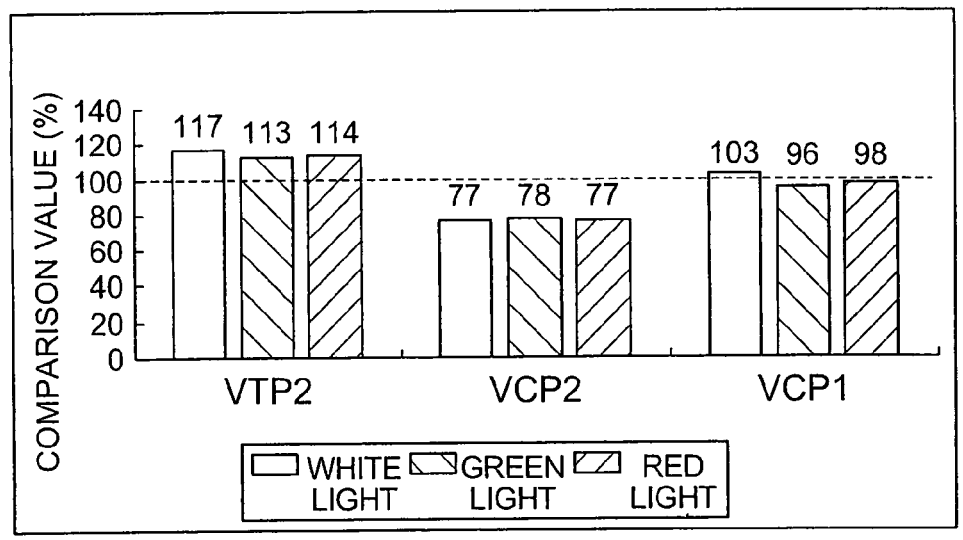

Fig.30

| | LAKE WATER | WELL WATER | TAP WATER | DISTILLED WATER | STANDARD DEVIATION |
|---|---|---|---|---|---|
| RAW WATER | 7.44 | 6.03 | 7.07 | 5.46 | 0.91 |
| HIGH SALINITY MEDIUM | 9.68 | 9.71 | 9.72 | 9.69 | 0.02 |
| LOW SALINITY MEDIUM | 8.13 | 7.77 | 8.14 | 8.29 | 0.22 |

Fig.35
(a) 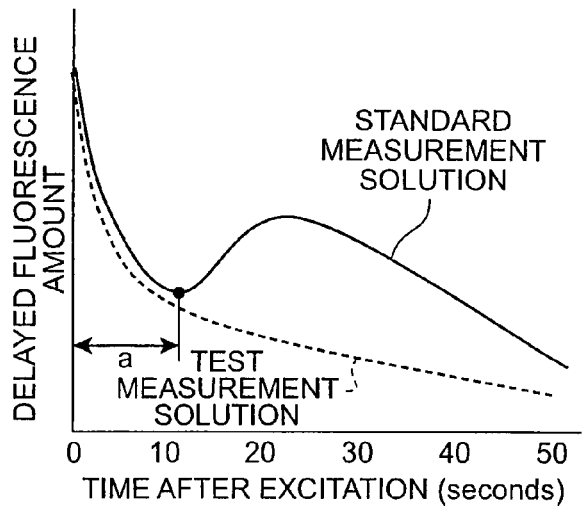
(b) 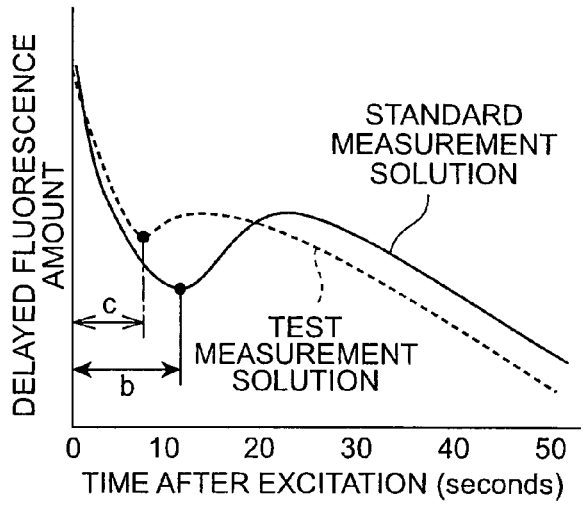
(c) 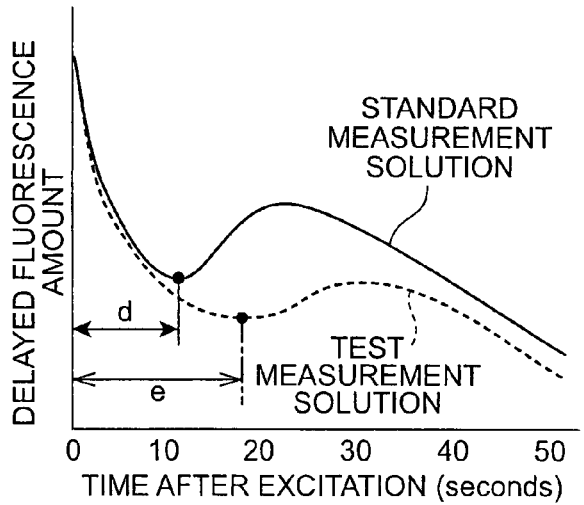

*Fig.37*
(a)
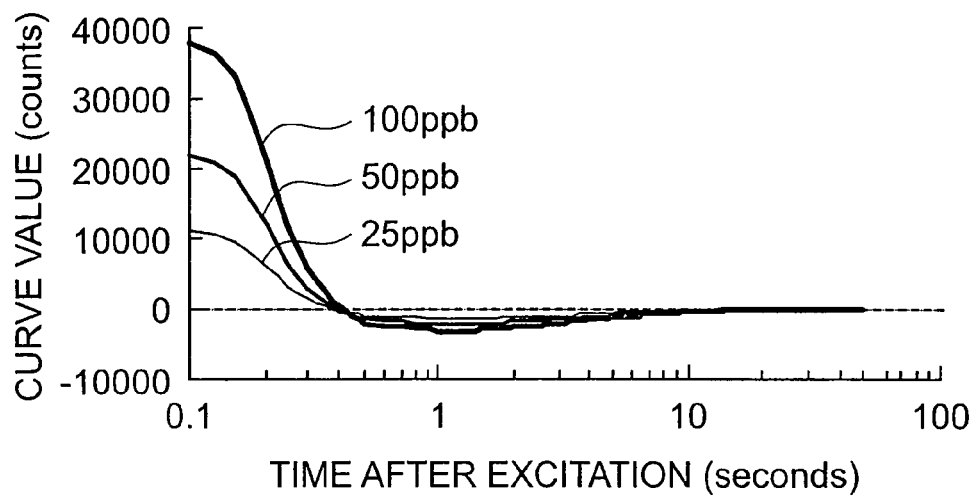
(b)
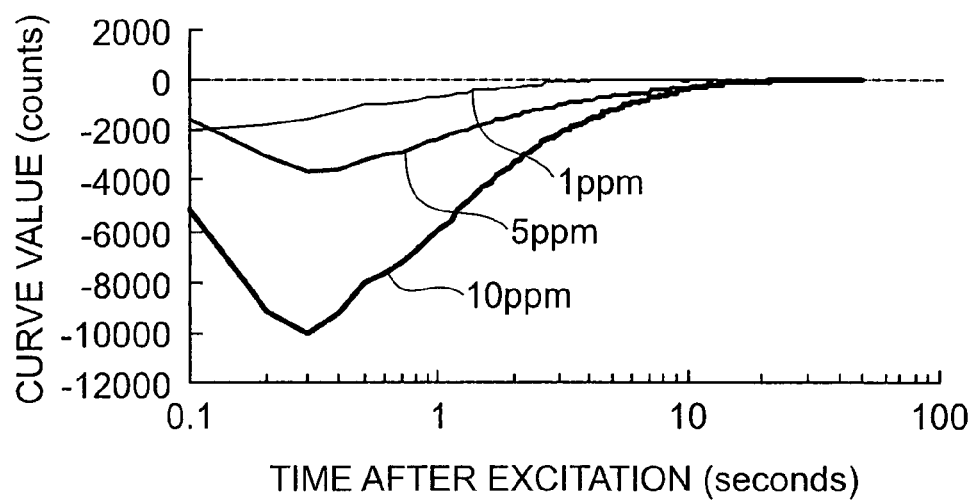

*Fig.38*
(a)
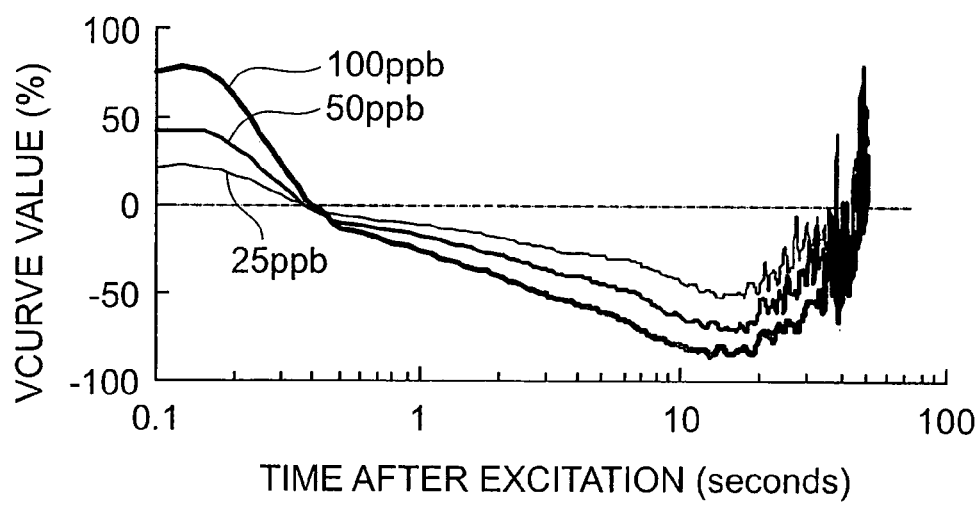
(b)
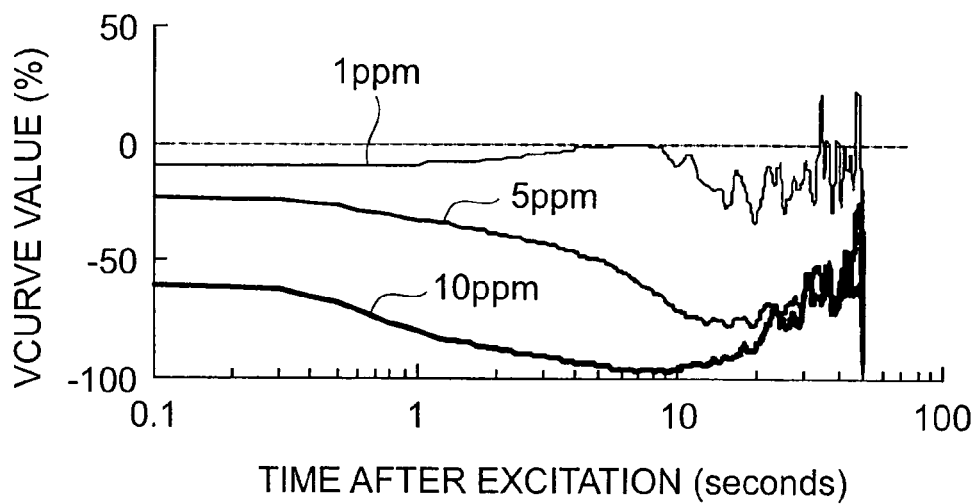

Fig.40

| PRELIMINARY ILLUMINATION CONDITIONS | PRECISION OF RESULTS OF THREE TIMES OF MEASUREMENT (STANDARD DEVIATION /AVERAGE × 100) |
|---|---|
| 2 TIMES OF MEASUREMENT CONDITIONS | 3.6 |
| 2 TIMES OF DARKNESS | 4.8 |
| 1 TIME OF MEASUREMENT CONDITIONS | 10.6 |
| 1 TIME OF DARKNESS | 14.2 |
| 1 TIME OF ILLUMINATION | 14.7 |
| LIGHT 30, DARKNESS 30 | 14.7 |
| LIGHT 1, DARKNESS 30 | 19.7 |
| NO ACCLIMATION | 21.2 |

HARMFUL SUBSTANCE EVALUATING METHOD AND HARMFUL SUBSTANCE EVALUATION KIT

TECHNICAL FIELD

This invention relates to a toxic substance assay method and a toxic substance assay kit.

BACKGROUND ART

As a method of assaying effects on living organisms of unknown chemical substances present in the environment, biological toxicity inspection of "bioassay," by which growth inhibition of bacteria, algae, water flea, fish, or other living organism is inspected, has been employed from before. Bioassay enables comprehensive detection of effects due to unknown substances or unexpected substances, interactions of chemical substances, environmental effects, and other biological effects, and is in a complementary relationship with conventional physicochemical methods such as liquid chromatography, gas chromatography, atomic absorption measurement, and enzyme immunoassay.

In bioassay, single-cell organisms, such as bacteria or algae, which enable a large number of individual organisms to be treated statistically and are short in lifecycle, or small aquatic organisms, such as small crustaceans (water fleas) or small fish, etc., which have comparatively advanced biological functions and yet are readily affected by chemical substances, etc., are used. As a specific example of a bioassay method, a method of biological effect assay by algae growth inhibition test, which is defined in guidelines of the Ministry of Environment of Japan, can be cited. The algae growth inhibition test is a method of assaying various toxicities of a tested substance on algae.

As another method, a method of measuring respiratory inhibition by measurement of luminescence by luminescent bacteria has been proposed. Also, Non-Patent Document 1 describes a method of measuring photosynthesis inhibition using chlorophyll fluorescence from algae. Non-Patent Documents 2 and 3 also describe measurement methods using delayed fluorescence.

Non-Patent Document 1: Ulrich Schreiber et al., "New type of dual-channel PAM chlorophyll fluorometer for highly sensitive water toxicity biotests", Photosynthesis Research 74, p. 317-330 (2002)

Non-Patent Document 2: Werner Schmidt and Horst Senger, "Long-term delayed luminescence in Scenedesmus obliquus. II. Influence of exogeneous factors", Biochimica et Biophysica Acta 891, p. 22-27 (1987)

Non-Patent Document 3: Joachim Burger and Werner Schmidt, "Long term delayed luminescence: A possible fast and convenient assay for nutrition deficiencies and environmental pollution damages in plants", Plant and Soil 109, p. 79-83 (1988)

DISCLOSURE OF THE INVENTION

Problems to be Solved by the Invention

However, with the above-mentioned method of biological effect assay by algae growth inhibition test, because the growth ability of a living organism is tested, operations are complicated and a long time of 24 hours to 72 hours is required to obtain test results. Meanwhile, with the measurement method described in the above-mentioned Non-Patent Document 1 and so on, though shortening of the test time is realized in part, it is still inadequate. In addition, all of these assay methods have yet to realize qualitative and quantitative analysis of a wide variety of toxic substances including unknown chemical substances. With the measurement methods described in Non-Patent Documents 2 and 3, specific methods for qualitative and quantitative analysis of toxic substances have not been examined adequately.

This invention has been made in view of the above problem and an object thereof is to provide a toxic substance assay method and a toxic substance assay kit that enable a wide range of toxic substances to be evaluated in a short time.

Means for Solving the Problems

In order to achieve the above object, this invention provides a toxic substance assay method that is a method of assaying a toxic substance present in an aqueous solution sample to be tested and includes: (1) a first step of mixing a photosynthetic sample, having a photosynthetic function, with the aqueous solution sample to prepare a test measurement solution, letting the test measurement solution stand for a predetermined standing time, and then after illuminating light onto the test measurement solution for a predetermined illumination time, measuring a light amount of a delayed fluorescence that is emitted; (2) a second step of letting a comparison measurement solution, prepared by mixing the photosynthetic sample with a comparison sample, stand for the predetermined standing time, and then after illuminating light onto the comparison measurement solution for the predetermined illumination time, measuring a light amount of the delayed fluorescence that is emitted to thereby prepare a comparison measurement result; and (3) a third step of computing assay values based on the light amounts of delayed fluorescence, respectively acquired in the first step and the second step, and determining a comparison value of the assay values to assay the toxic substance present in the aqueous solution sample, wherein (4) the assay values are elapsed times of characteristic points in temporal variations of the light amounts of delayed fluorescence acquired in the first step and the second step.

Or, this invention provides a toxic substance assay method that is a method of assaying a toxic substance present in an aqueous solution sample to be tested and includes: (1) a first step of mixing a photosynthetic sample, having a photosynthetic function, with the aqueous solution sample to prepare a test measurement solution, letting the test measurement solution stand for a predetermined standing time, and then after illuminating light onto the test measurement solution for a predetermined illumination time, measuring a light amount of a delayed fluorescence that is emitted; (2) a second step of letting a comparison measurement solution, prepared by mixing the photosynthetic sample with a comparison sample, stand for the predetermined standing time, and then after illuminating light onto the comparison measurement solution for the predetermined illumination time, measuring a light amount of the delayed fluorescence that is emitted to thereby prepare a comparison measurement result; and (3) a third step of computing assay values based on the light amounts of delayed fluorescence, respectively acquired in the first step and the second step, and determining a comparison value of the assay values to assay the toxic substance present in the aqueous solution sample, wherein (4) the assay values are temporal variations of the light amounts of delayed fluorescence acquired in the first step and the second step, and the comparison value is a value obtained by determining a difference of the temporal variations.

With such a toxic substance assay method, a plurality of toxic substances can be analyzed qualitatively and quantitatively at the same time and at high precision from characteristics obtained by a comparison of the temporal variation of the light amount of delayed fluorescence emitted from the photosynthetic sample mixed with the aqueous solution sample to be assayed and the temporal variation of the light amount of delayed fluorescence emitted from the photosynthetic sample in the comparison measurement solution containing the comparison sample that is prepared to be compared with the aqueous solution sample. By performing the assay by measuring the light amounts of delayed fluorescence, the measurement time can be shortened as a whole.

In the first of the assay methods described above, the assay values are the elapsed times of the characteristic points in the temporal variations of the light amounts of delayed fluorescence acquired in the first step and the second step. In this case, because the characteristic points in the temporal variations of the delayed fluorescence light amount vary according to each chemical substance species that is a toxic substance, by assaying the elapsed times of the characteristic points, various toxic substances can be analyzed qualitatively and quantitatively more accurately.

With the second of the assay method, the assay values are the temporal variations of the delayed fluorescence light amounts acquired in the first step and the second step, and the comparison value is a value obtained by determining a difference of the temporal variations. In this case, a point in time at which the temporal variations of the delayed fluorescence light amounts are concentrated, an inflection point, or other characteristic can be obtained to enable the chemical substance species that are toxic substances to be specified readily.

Also, with the second of the assay method described above, a method may be employed wherein the temporal variation of the light amount of delayed fluorescence acquired in the first step or the second step has a characteristic point, and in the third step, a value obtained by determining a difference of the temporal variations of the light amounts of delayed fluorescence within a predetermined range between one characteristic point and a measurement starting point or another characteristic point is used as the comparison value to assay the toxic substance. In a case where there are no characteristic points in the temporal variations of the delayed fluorescence light amounts, a value obtained by determining a difference of the temporal variations of the light amounts of delayed fluorescence over the entirety or a predetermined range can be used as the comparison value.

Or, a method may be employed wherein in the third step, a value, determined as a ratio of a value determined as a difference of the temporal variations of the light amounts of delayed fluorescence acquired in the first step and the second step, with respect to the temporal variation of the light amount of delayed fluorescence acquired in the first step or the second step, is used as the comparison value to assay the toxic substance.

Here, as the comparison sample used in the second step and the comparison measurement result, any of various comparison samples and comparison measurement results may be used. For example, a method may be employed wherein in the second step, a standard sample to be compared with is used as the comparison sample, the photosynthetic sample is mixed with the standard sample to prepare a standard measurement solution that is the comparison measurement solution, the standard measurement solution is left to stand for the predetermined standing time, and then after illuminating light onto the standard measurement solution for the predetermined illumination time, the light amount of the delayed fluorescence that is emitted is measured to acquire the comparison measurement result. In this case, a sample in which practically no toxic substances are present is preferably used as the standard sample.

Or, a method may be employed wherein in the second step, another aqueous solution sample is used as the comparison sample and a measurement result, acquired on another test measurement solution that is the comparison measurement solution prepared by mixing the other aqueous solution sample with the photosynthetic sample, is prepared as the comparison measurement result. In this case, for example, a previous measurement result may be used as the comparison measurement result.

Also, in regard to the acquisition of the comparison measurement result in the second step, a method may be employed wherein the comparison measurement result is prepared by measuring the light amount of delayed fluorescence of the comparison measurement solution in the same manner as in the first step. Or, a method may be employed wherein, in the second step, a measurement result that is acquired in advance for the comparison measurement solution is used as the comparison measurement result. In this case, the comparison measurement result that is acquired in advance is preferably stored in a memory, etc., and used upon being read out as data as necessary.

Also, it is preferable that, in the first step and the second step, the test measurement solution and the comparison measurement solution are left to stand for a predetermined standing time with light conditions being varied in each measurement, and in the third step, a variation of the comparison values according to the light conditions is evaluated. With this method, because the effect of the light conditions on the delayed fluorescence characteristics differ according to toxic substance, the distinguishing of the toxic substances in the aqueous solution sample is facilitated further by evaluating the comparison values corresponding to the changes of the light conditions during standing.

Further, the densities of the photosynthetic sample in the test measurement solution and in the comparison measurement solution are preferably within a range of densities that are in a proportional relationship with the light amount of delayed fluorescence. In this case, for example, by measuring the density of the photosynthetic sample by measuring the absorbance, etc., and then correcting the delayed fluorescence light amount based on this density, toxic substance assay of higher precision is realized.

In addition, preferably in the first step and the second step, the test measurement solution and the comparison measurement solution are homogenized before measuring the light amount of delayed fluorescence. Because by doing so, the photosynthetic sample in the measurement solution is distributed uniformly during measurement, toxic substance assay of even less error is enabled.

In regard to the photosynthetic sample mixed with the aqueous solution sample, at least one type of photosynthetic sample, selected from the group consisting of halotolerant algae, alkali-tolerant algae, and acid-tolerant algae, is preferably used. *Spirulina* can be cited as an example of such a photosynthetic sample.

This invention farther provides a toxic substance assay method that is a method of assaying a toxic substance present in an aqueous solution sample to be tested and includes: (a) a preparing step of mixing the aqueous solution sample with a photosynthetic sample, having a photosynthetic function, to prepare a test measurement solution; (b) a standing step of letting the test measurement solution stand for a predetermined standing time; (c) a measuring step of illuminating light onto the test measurement solution for a predetermined illumination time and thereafter measuring the light amount of delayed fluorescence that is emitted; (d) an assaying step of assaying a toxic substance present in the aqueous solution sample based on the light amount of delayed fluorescence acquired in the measuring step; and (e) an acclimating step, preceding the measuring step and including one of either a dark standby step of subjecting the test measurement solution to a dark standby for a predetermined standby time or a preliminary illuminating step of subjecting the test measurement solution to a preliminary light illumination and to a dark standby for a predetermined standby time.

With such a toxic substance assay method, a plurality of toxic substances can be analyzed qualitatively and quantitatively at the same time and at high precision from characteristics obtained from the temporal variations of the light amount of delayed fluorescence emitted from the photosynthetic sample mixed with the aqueous solution sample to be assayed. By performing the assay by measuring the delayed fluorescence light amount, the measurement time can be shortened as a whole. Also, by performing the acclimating step on the test measurement solution before the measuring step, the precision of measurement of the delayed fluorescence and the precision of the assay of toxic substances by the measurement results can be improved.

In a case where the adaptation step is performed before the measuring step as described above, the predetermined standby time in the dark standby step is preferably no less than 30 seconds and no more than 1 hour. Also, the ratio of the preliminary light illumination time to the dark standby time in the preliminary illuminating step is preferably equal to the ratio of the light illumination time to the dark standby time in the measuring step.

For such assay, a toxic substance assay kit, for assaying a toxic substance present in an aqueous solution sample to be tested and including: a photosynthetic sample to be mixed with the aqueous solution sample; a salt mixture for adjusting the salt concentration and the pH of the aqueous solution sample; and a mixing means that mixes the aqueous solution sample with the photosynthetic sample and with the salt mixture in a separated manner; is provided. The assay kit preferably also includes a stabilizer for homogenizing the distribution density of the photosynthetic sample. Specific gravity adjusting agents and thickening agents can be cited as examples of such a stabilizer.

Effects of the Invention

With the toxic substance assay method according to this invention, a wide range of toxic substances can be analyzed in a short time.

BRIEF DESCRIPTION OF THE DRAWINGS

FIG. 6 shows (a) a graph of an example of a relationship between absorbance at a wavelength of 665 nm and the delayed fluorescence amount, and (b) a graph of an example of a relationship between absorbance at a wavelength of 750 nm and the delayed fluorescence amount.

FIG. 8 shows (a) a graph of assay values CP1 at various light intensities, (b) a graph of assay values CP2 at various light intensities, and (c) a graph of assay values TP2 at various light intensities.

FIG. 22 shows (a) a graph of comparison values VCP1 of various test measurement solutions containing different types of biological growth inhibition factors, (b) a graph of comparison values VCP2 of various test measurement solutions containing different types of biological growth inhibition factors, and (c) a graph of comparison values VTP2 of various test measurement solutions containing different types of biological growth inhibition factors.

FIG. 23 shows (a) a graph of comparison values VCP1 of various test measurement solutions containing the same types of biological growth inhibition factors, (b) a graph of comparison values VCP2 of various test measurement solutions containing the same types of biological growth inhibition factors, and (c) a graph of comparison values VTP2 of various test measurement solutions containing the same types of biological growth inhibition factors.

FIG. 27 shows (a) a graph of comparison values concerning TPN for various light conditions during standing, and (b) a graph of comparison values concerning inorganic mercury for various light conditions during standing.

FIG. 30 is a table of adjustment examples of adjusting aqueous solution samples using a high salinity medium and a low salinity medium.

FIG. 35 shows diagrams of examples of methods of computing the Curve values when characteristics points exist in delayed fluorescence decay curves.

FIG. 37 shows graphs of the Curve values in cases where the concentration of simazine and the concentration of dichlorophenol are varied.

FIG. 38 shows graphs of the VCurve values in cases where the concentration of simazine and the concentration of dichlorophenol are varied.

FIG. 40 is a table of measurement precisions of results of measuring delayed fluorescence three times.

DESCRIPTION OF SYMBOLS

Figure 1:
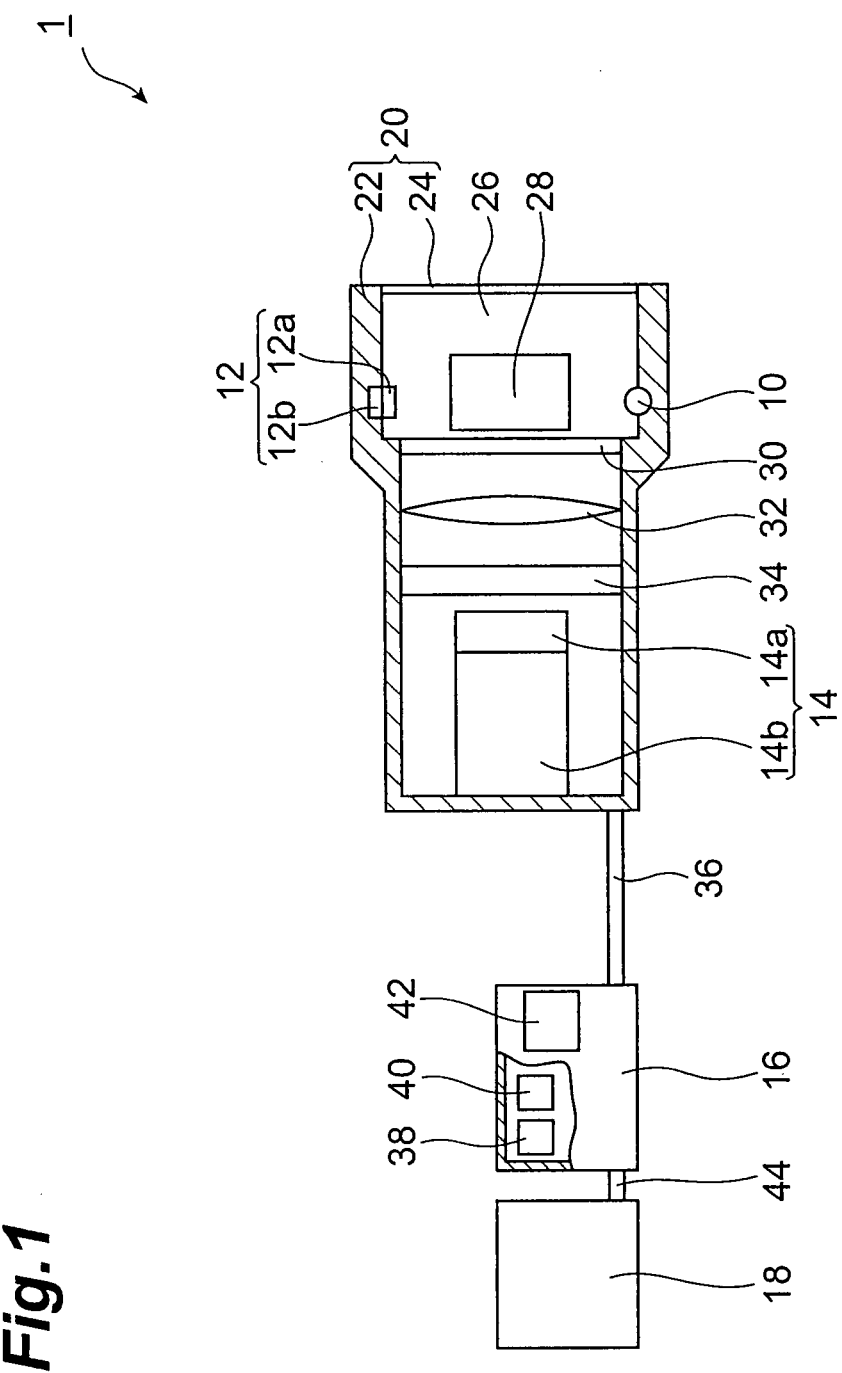
FIG. 1 is a diagram of an embodiment of a delayed fluorescence measuring device.

1—delayed fluorescence measuring device, 10—light source, 12—first measuring unit, 12a—first photosensor, 12b—scattered light amount computing unit, 14—measuring unit, 14a—second photosensor, 14b—delayed fluorescence amount computing unit, 16—analyzing unit, 18—controlling unit, 20—casing, 22—main unit, 24—lid portion, 26—entrance, 28—setting unit, 30—filter, 32—converging optical system, 34—shutter, 36, 44—cable, 38—computing unit, 40—storage unit, 42—display unit, 50—liquid sampling container, 52—aqueous solution sample, 54—adjusting solution, 56—concentrated photosynthetic sample, 58—test measurement solution, 60—liquid sampling container.

BEST MODE FOR CARRYING OUT THE INVENTION

Embodiments of this invention shall now be described, with reference to the accompanying drawings. In the drawings, components that are the same shall be provided with the same symbol and overlapping description shall be omitted.

(Delayed Fluorescence Measuring Device)

Figure 2:
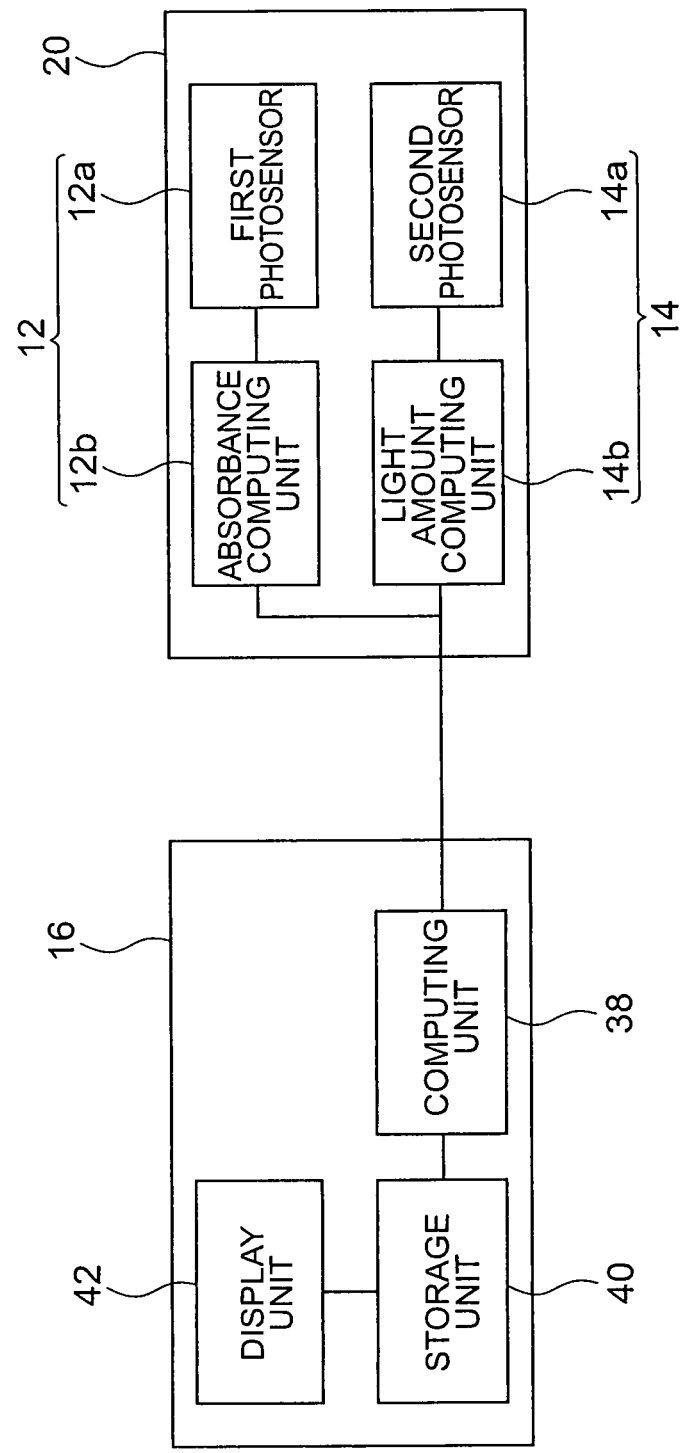
FIG. 2 is a block diagram of a portion of the delayed fluorescence measuring device of FIG. 1.

First, a delayed fluorescence measuring device for carrying out a toxic substance assay method according to this invention shall be described. FIG. 1 is a diagram of an embodiment of a delayed fluorescence measuring device, and FIG. 2 is a block diagram of a portion of the delayed fluorescence measuring device.

Delayed fluorescence measuring device 1 includes a light source 10, a first measuring unit 12, a second measuring unit 14, an analyzing unit 16, and a controlling unit 18. Light source 10 illuminates measurement light of a predetermined wavelength onto a solution to be measured, and the wavelength thereof is in a range of 280 nm to 800 nm. Here, light source 10 may be a monochromatic light source or may be a light source combining a plurality of light sources. Emission of light by light source 10 may continue for a predetermined time, or pulse lighting may be performed in an arbitrary pattern. Also, a plurality of light sources having the same or different wavelength characteristics may be made to emit light in succession, or the plurality of light sources may be made to emit light simultaneously.

First measuring unit 12 measures the absorbance or the scattered light amount of a solution with respect to the measurement light, and includes a first photosensor 12a that detects transmitted light or scattered light of the measurement light illuminated onto the solution and an absorbance or scattered light amount computing unit 12b that computes the absorbance or the scattered light amount based on a signal output by first photosensor 12a upon detection.

Second measuring unit 14 measures the light amount of delayed fluorescence emitted from a photosynthetic sample (details of which shall be described later) upon illumination of the measurement light, and includes a second photosensor 14a that detects the delayed fluorescence and a delayed fluorescence amount computing unit 14b that computes the light amount of delayed fluorescence based on a signal output by second photosensor 14a upon detection. Here, the delayed fluorescence occurs in the following manner. That is, in a biological reaction having a photosynthetic function, light energy that is absorbed by an assimilation pigment (photosynthetic pigment) is transferred in the biological reaction as chemical energy by an electron transfer pathway. In this transfer process, a portion of the chemical energy undergoes a reverse reaction and the photosynthetic pigment is re-excited by this chemical energy. Emission of fluorescence occurs from the photosynthetic pigment that is thus re-excited. Delayed fluorescence is also referred to as delayed luminescence, and in the following description, shall be referred to comprehensively as delayed fluorescence.

Light source 10, first measuring unit 12, and second measuring unit 14 are housed in casing 20 with a light blocking property. Casing 20 may be formed of a light blocking member that blocks light in itself or may be formed of a member coated with a coating, etc., that blocks light.

Casing 20 has a main unit 22 and lid portion 24. Main unit 22 has an entrance 26 formed at one end thereof. Entrance 26 is formed for placing a solution, containing a photosynthetic sample, inside casing 20, and is closed by lid portion 24.

Also, inside casing 20, a setting unit 28, in which a container (not shown), containing a solution, can be set, is disposed between light source 10 and first measuring unit 12. Setting unit 28 has, for example, a fixing claw for fixing the container and is arranged to fix the container by means of this fixing claw.

Between setting unit 28 and second measuring unit 14 inside casing 20 are disposed a filter 30, a converging optical system 32, and a shutter 34. Filter 30 is disposed so as to contact an inner wall face of casing 20 and transmits delayed fluorescence. Converging optical system 32 converges the weak delayed fluorescence. Shutter 34 is enabled to open and close, and blocks the delayed fluorescence when closed.

Analyzing unit 16 is connected via a first cable 36 to first measuring unit 12 and second measuring unit 14 and has a computing unit 38, a storage unit 40, and a display unit 42. Based on the absorbance or the scattered light amount measured by means of first measuring unit 12 and the delayed fluorescence light amount measured by means of second measuring unit 14, computing unit 38 determines, in accordance with a computing method to be described later, a comparison value correlated to a toxic substance present in a solution. Storage unit 40 successively stores the comparison values determined by computing unit 38. Display unit 42 displays or illustrates a plurality of the comparison values that are successively stored in storage unit 40.

Controlling unit 18 is connected via a second cable 44 to analyzing unit 16. Controlling unit 18 is thus connected to first measuring unit 12 and second measuring unit 14 via second cable 44 and first cable 36. Also, controlling unit 18 sends control signals for controlling the opening/closing of lid portion 24, the emission of light and the stoppage of light emission by light source 10, and the opening/closing of shutter 34.

(Toxic Substance Assay Method)

Figure 3:
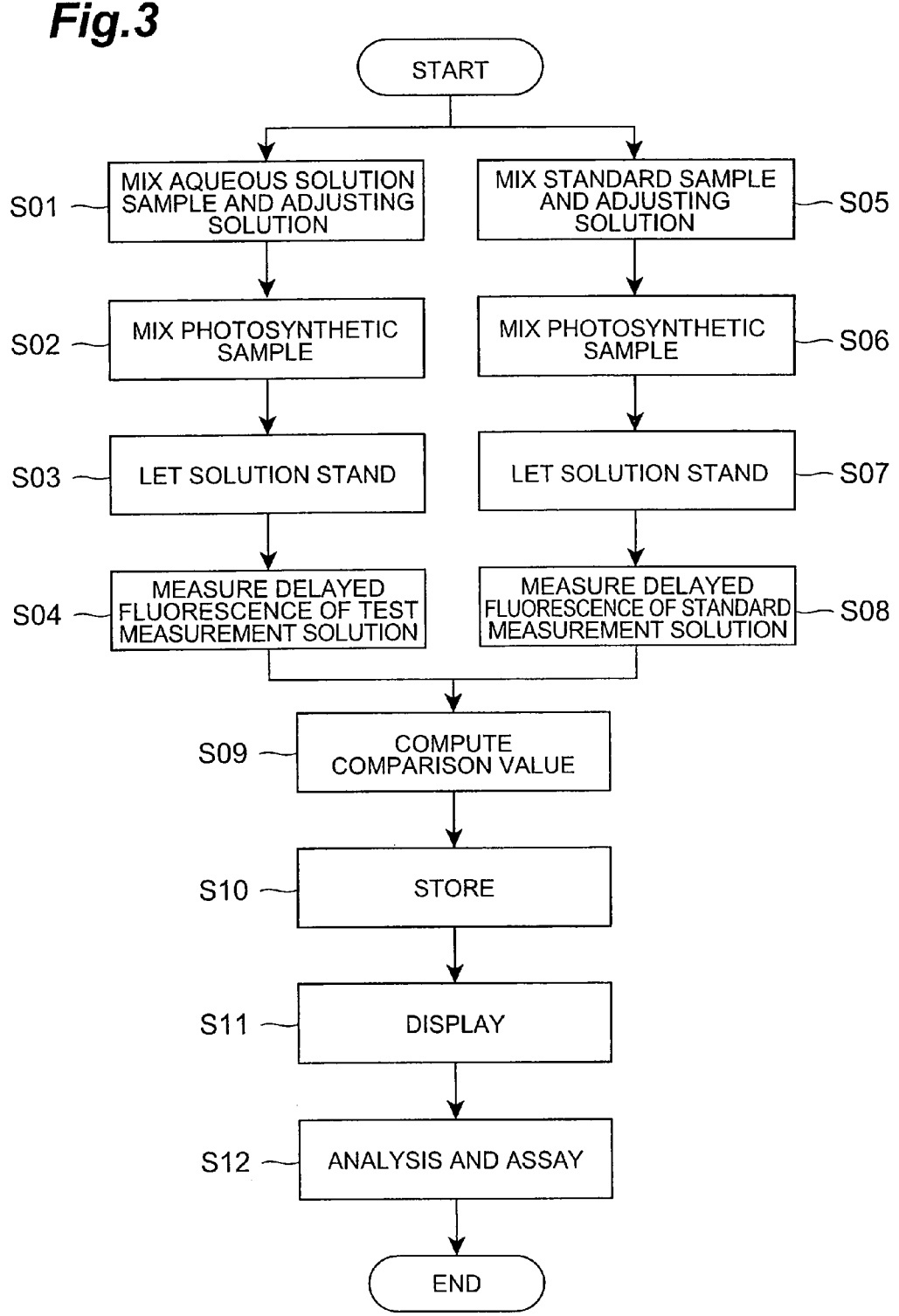
FIG. 3 is a flowchart of procedures of a biological growth inhibition factor assay method according to an embodiment of this invention.

A toxic substance assay method according to this invention shall now be described in detail. FIG. 3 is a flowchart of procedures of method of assaying biological growth inhibition factors as toxic substances. This assay method is for assaying a biological growth inhibition factor that is present in an aqueous solution sample to be tested. Here, a biological growth inhibition factor refers to a factor that exhibits growth inhibition, toxicity, or other ill effect on a biological organism, such as bacteria, algae, water flea, fish, etc.

First, the aqueous solution sample to be tested and an adjusting solution are mixed inside a cuvette or other container (step S01).

As the aqueous solution sample, water that is directly sampled from a lake, swamp, river, well water, or other natural water source, an aqueous solution that contains extracted components obtained by a general extraction method from soil, sludge, or other solid matter, an aqueous solution that is collected by rinsing a surface of a vegetable or other object sprayed with an agricultural chemical, an aqueous solution that is obtained by making a gas component be absorbed in a liquid, an aqueous solution that contains extracted components obtained by a general extraction method from a plant or animal (vegetable or meat), etc., an aqueous solution that contains extracted components obtained by a general extraction method from a tissue fluid, blood, milk, or feces or urine or other excrement sampled from a plant or animal, etc., can be used. Also, as the above-mentioned aqueous solution sample, a sample, which has been separated or concentrated in advance into water-soluble substances, hydrophobic substances, or other components that differ in characteristics by fractionation by solvent extraction, solid phase extraction, etc., may be used.

The adjusting solution is a solution that contains various salts for adjusting the salt concentration and the pH of the aqueous solution sample. In preparing a measurement solution to be used in delayed fluorescence measurement using a photosynthetic sample, the aqueous solution sample is an unknown aqueous solution, and in many cases, the salt concentration, pH, etc., thereof vary widely. It is known that the photosynthetic functions of the photosynthetic sample will be affected when the salt concentration and the pH are not within appropriate ranges. The adjusting solution is thus used to adjust the salt concentration and the pH of the measurement solution. Furthermore, in order to make measurements of high sensitivity, it is preferable for the distribution density of the photosynthetic sample in the measurement solution in a cuvette to be homogenous and unbiased and that there be no settling matter or floating matter during measurement. The adjusting solution thus preferably contains a stabilizer for homogenization so that a bias will not arise in the distribution density of the photosynthetic sample in the measurement solution. For example, the measurement solution may be homogenized by being provided with some degree of viscosity or being matched in specific gravity with the photosynthetic sample.

As examples of the solute of the adjusting solution, a salt mixture that adjusts the salt concentration and the pH of the aqueous solution sample to conditions suited for the photosynthetic sample, a stabilizer that homogenizes the distribution density of the photosynthetic sample in the measurement solution, nutrient salts that are required as minimum for a photosynthetic reaction, etc., can be cited. As a stabilizer to be contained in the adjusting solution, a specific gravity adjusting agent or a gelling agent (thickening agent), etc., needed for spatial stabilization of the photosynthetic sample during measurement, can be used. By using such a specific gravity adjusting agent, the specific gravity of the measurement solution is adjusted to substantially match that of the photosynthetic sample. This stabilizer may be contained in the photosynthetic sample, to be described below, instead of in the adjusting solution.

The photosynthetic sample is then mixed into the aqueous solution sample, which has been adjusted by the adjusting solution, inside the cuvette or other container to prepare a test measurement solution (step S02, preparing step). Here, the photosynthetic sample is mixed so that it will be of uniform concentration in the test measurement solution.

It is sufficient for the photosynthetic sample to have a photosynthetic function and be able to emit delayed fluorescence, and algae, phytoplankton, cyanobacteria, photosynthetic bacteria, a plant body or leaf or fragment thereof, cultured plant cells, such as a callus, photosynthetic organelles or thylakoid membrane extracted from a plant, an artificially synthesized membrane or protein complex that has a photosynthesis-like function, etc., can be cited as examples. As favorable examples, *Spirulina*, which is a blue-green algae, *Selenastrum*, which is a green algae, *Isochrysis*, which is a yellow algae, or a thylakoid membrane extracted from spinach, etc., can be used.

The test measurement solution prepared as described above is left to stand under predetermined light conditions for a predetermined standing time (step S03, standing step). Light conditions shall refer to such environmental conditions as the wavelength and light amount of light illuminated onto the test measurement solution during standing, and shall refer to the wavelengths and light amounts of the respective components in the case of a synthetic light.

The light amount of the delayed fluorescence that is emitted from the test measurement solution is then measured as described below to determine the temporal variation of the light amount of delayed fluorescence (step S04, measuring step).

Figure 4:
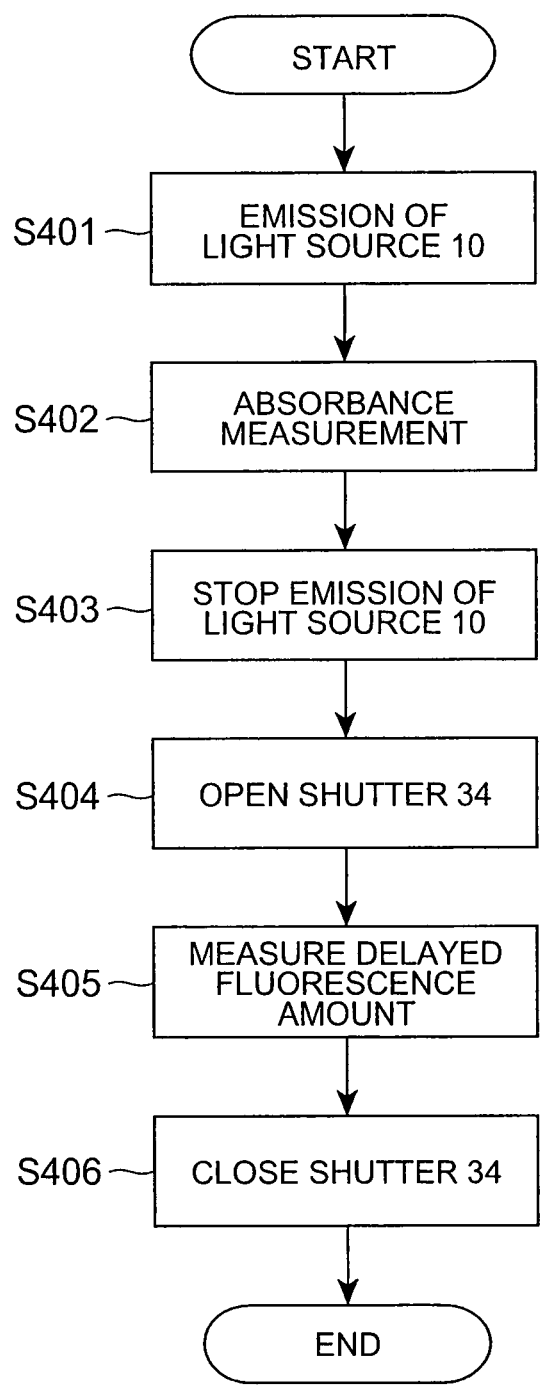
FIG. 4 is a flowchart of operations of delayed fluorescence measuring device 1 in a process of measuring a light amount of delayed fluorescence.

FIG. 4 is a flowchart of operations of delayed fluorescence measuring device 1 in the process of measuring the delayed fluorescence light amount. It shall be deemed that a container, containing the test measurement solution, is set in setting unit 28 inside casing 20.

First, controlling unit 18 sends the control signal for making light source 10 emit light. Light source 10 thereby emits light (step S401). By this light emission, a preliminary light illumination for acclimating the photosynthetic sample to the measurement light is performed on the test measurement solution and thereafter, light illumination for making delayed fluorescence occur is performed for a predetermined illumination time. When light source 10 emits light, first measuring unit 12 measures the absorbance or the scattered light amount of the test measurement solution (step S402). After measurement, first measuring unit 12 sends information concerning the absorbance or the scattered light amount to computing unit 38. Thereafter, controlling unit 18 sends the control signal for stopping the emission of light by light source 10. Light source 10 thus stops emitting light (step S403). The above-mentioned measurement of the absorbance or the scattered light amount may be performed during the preliminary light illumination.

After the stoppage of light emission, controlling unit 18 sends the control signal for opening shutter 34. Shutter 34 thus undergoes an opening operation (step S404). When shutter 34 opens, second measuring unit 14 measures the delayed fluorescence light amount (step S405). After measurement, second measuring unit 14 sends information concerning the temporal variation of the light amount of delayed fluorescence within a predetermined measurement time to computing unit 38. Thereafter, controlling unit 18 sends the control signal for closing shutter 34. Shutter 34 thus undergoes a closing operation (step S406).

Measurement of the delayed fluorescence amount concerning the test measurement solution (first step) is completed by the above processes.

Returning now to FIG. 3, a standard sample and the adjusting solution are mixed in another container, such as a cuvette, under the same conditions as step S01 (step S05). Here, the standard sample is a solution, for which it is known that a toxic substance that is a biological growth inhibition factor is not present therein, and, for example, sterilized distilled water, pure water, or other water from which impurities and bacteria have been removed, is used.

Then, under the same conditions as step S02, the photosynthetic sample is mixed with the standard sample, which has been adjusted by the adjusting solution, in the cuvette or other container to prepare a standard measurement solution (step S06). Thereafter, the delayed fluorescence amount of the standard measurement solution is measured in the same manner as steps S03 and S04 (steps S07 and S08; the above shall be referred to hereinafter as the second step).

The above-described delayed fluorescence amount measurement (steps S401 to S406) may be repeated a plurality of times on each of the test measurement solution and the standard measurement solution and average values of the measurements may be computed to improve the measurement precision.

When the temporal variations of the delayed fluorescence amounts of the test measurement solution and the standard measurement solution and the absorbances (or scattered light amounts) of the respective solutions during measurement have been measured, computing unit 38 determines a comparison value correlated to biological growth inhibition factors based on the temporal variations of the delayed fluorescence amounts (step S09).

Figure 5:
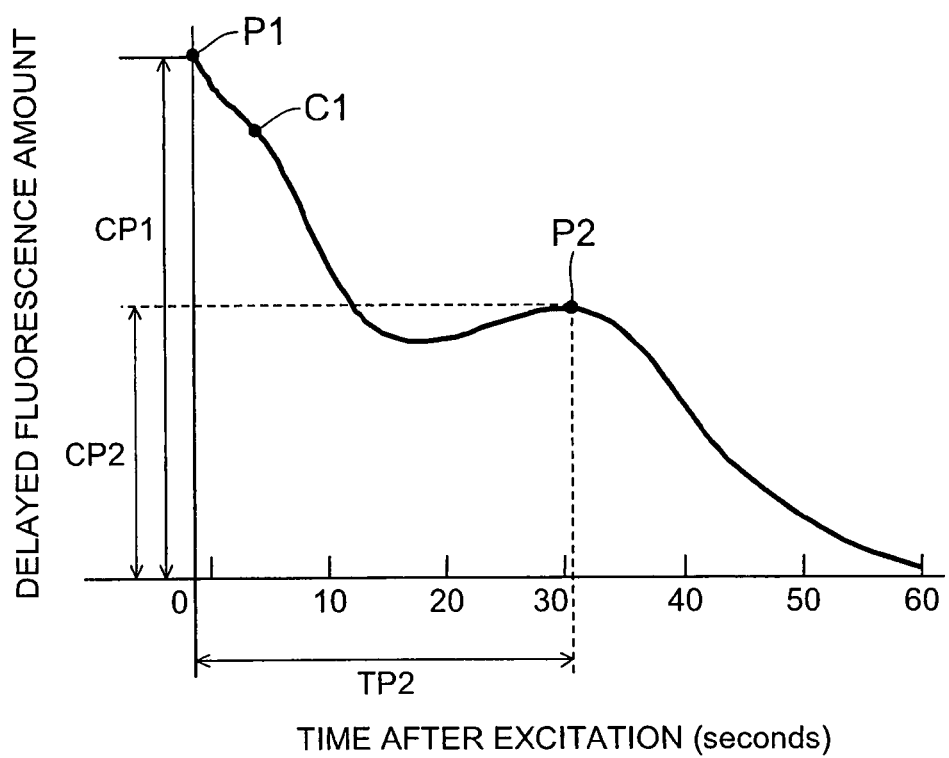
FIG. 5 is a diagram of an example of a temporal variation of the light amount of delayed fluorescence.

FIG. 5 is a diagram of an example of a temporal variation of the light amount of delayed fluorescence under standard measurement conditions. Here, the standard measurement conditions are as follows. First, *Spirulina platensis*, which is a blue-green algae and has been grown by a general method under a red monochromatic light of a wavelength of 665 nm and a light intensity of 50 $\mu mol/m^2/s$, is prepared as the photosynthetic sample, and 1.8 ml of sterilized distilled water is prepared as the standard sample. 0.6 ml of an adjusting solution, containing a standard blue-green algae culturing salt mixture of 4 times concentration and a salt mixture for pH and salt concentration adjustment, are added to the standard sample. 0.6 ml of the photosynthetic sample, containing *Spirulina platensis* at a uniform density such that the OD as absorbance at 665 nm is approximately 0.1 and containing 0.5 weight % of agar as a gelling agent, are then mixed to prepare 3 ml of the measurement solution.

Thereafter, the measurement solution is left to stand for approximately 15 minutes under a white fluorescent lamp of a light intensity of 1.5 $\mu mol/m^2/s$. Then, using delayed fluorescence measuring device 1, the photosynthetic sample is subject to 2 seconds of illumination light of 665 nm and 0.8 $mW/cm^2$ as preliminary light illumination for acclimating the sample to the measurement light conditions and then put on standby under total darkness for 60 seconds. Then, after illuminating excitation light of 665 nm and 0.8 $mW/cm^2$ for 2 seconds again, the light amount of delayed fluorescence is measured for 60 seconds at a time resolution of 0.1 seconds. This measurement of 60 seconds is executed three times and the temporal variation of the light amount of delayed fluorescence is obtained from the average values. The same applies likewise to aqueous solution samples.

As shown in FIG. 5, a delayed fluorescence decay curve (temporal variation of the light amount of delayed fluorescence) that is obtained has a first peak (P1), which is a peak of the decay curve that follows from the end of light illumination, and a second peak (P2), which appears near 25 to 35 seconds after the end of light illumination. Also, an inflection point (C1) appears at point between the first peak (P1) and the second peak (P2) and near P1. These points (characteristics points) P1, P2, and C1 exhibit characteristic variations according to the types of biological growth inhibition factors. These variations in the characteristic points are brought about by variations of the sensitivity of the photosynthetic sample to the biological growth inhibition factors. Characteristic points are not restricted to the above-mentioned three points, and a minimum point between P1 and P2 or other inflection point in the delayed fluorescence decay curve may be used as well.

Here, computing unit 38 detects the characteristic points in the delayed fluorescence decay curves of the test measurement solution and the standard measurement solution and computes assay values for assaying the characteristic points. As these assay values, a delayed fluorescence amount CP1 at P1, a delayed fluorescence amount CP2 at P2, and an elapsed time TP2 at P2 from the end of light illumination are used. Also, as assay values for assaying inflection point C1, values of the temporal variations of the light amounts of delayed fluorescence of the test measurement solution and the standard measurement solution are used.

Here, computing unit 38 also performs correction of the light amounts of delayed fluorescence or the assay values based on the absorbances (or scattered light amounts) during measurement of the respective measurement solutions. This correction is performed to correct for measurement errors due to concentration differences of the photosynthetic sample in the measurement solutions. These measurement errors occur due to the illuminated light amount and the optical path varying according to the positioning of the photosynthetic sample in setting unit 28 or according to the position of setting unit 28 itself, especially when regions of ultralow variation are to be evaluated for the photosynthetic sample. A cell density, measured based on the absorbance (or scattered light amount), can be used effectively for this correction.

To perform the above-mentioned correction precisely, the densities of the photosynthetic samples in the test measurement solution and the standard measurement solution are preferably within ranges of densities that are in a proportional relationship to the corresponding light amounts of delayed fluorescence. That is, when the photosynthetic sample density in a measurement solution is no more than a certain value, the absorbance (or scattered light amount) and the light amount of delayed fluorescence exhibit a high correlation with the photosynthetic sample density. The upper limit of this density is suitably set according to the characteristics of the photosynthetic sample.

In FIG. 6, graph (a) is a graph of an example of a relationship between absorbance (OD665) at a wavelength of 665 nm and the delayed fluorescence amount CP1, and graph (b) is a graph of an example of a relationship between absorbance (OD750) at a wavelength of 750 nm and the delayed fluorescence amount CP1. The examples of FIG. 6 show that the absorbance and the delayed fluorescence amount CP1 are highly correlated up to an absorbance (OD) of approximately 0.5. It can be understood, however, that with OD=0.5 or more, the delayed fluorescence amount exhibits an apparent decrease due to self-absorption by the photosynthetic sample itself. Thus, in this case, as long as the absorbance is within a range of OD=0.5 or less, the delayed fluorescence amount can be corrected at high precision based on the absorbance.

Computing unit 38 then computes a comparison value from the assay values to make the effect due to the biological growth inhibition factor in the aqueous solution sample more apparent. As examples of the comparison values, a VCP1 value, a VCP2 value, and a VTP2 value, obtained by determining the ratios of CP1, CP2, and TP2 obtained respectively from the test measurement solution and the standard measurement solution, and Curve values, obtained by determining differences of the temporal variations of the light amounts of delayed fluorescence respectively obtained from the test measurement solution and the standard measurement solution, are used. By evaluating these comparison values, the sensitivity of the photosynthetic sample to the biological growth inhibition factors can be evaluated appropriately.

In the present Specification, it shall be deemed that CP1 is computed as the integrated amount of delayed fluorescence [counts] from 0.1 seconds to 0.5 seconds after the end of light illumination, TP2 is computed as the time elapsed from the end of light illumination [sec] to the point at which the second peak (or a similar inflection point) appears, CP2 is computed as the integrated amount of delayed fluorescence [counts] in ±0.5 seconds with respect to the time at which the second peak (or a similar inflection point) appears, the Curve values are the differences [counts] between the delayed fluorescence decay curve, between the first peak and the second peak and including C1, of the test measurement solution and that of the standard measurement solution, and the values of VCP1, VCP2, and VTP2 are computed as the respective ratios of CP1, CP2, and TP2 of the test measurement solution with respect to those of the standard measurement solution. Specific methods of computing these assay values and comparison values may be suitably selected as necessary.

Also, to detect the biological growth inhibition factor at high sensitivity using the comparison value computed in the above manner, the photosynthetic sample is preferably adequately low in density, even within the above-mentioned range of photosynthetic sample densities that are in a proportional relationship with the light amount of delayed fluorescence.

Figure 7:
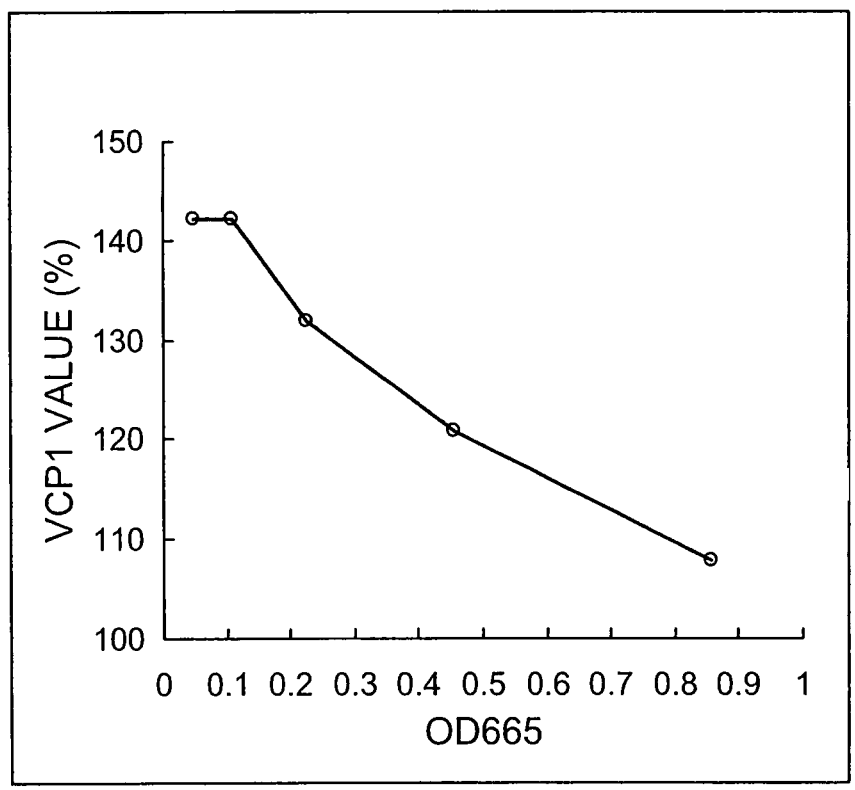
FIG. 7 is a graph of a variation of a comparison value VCP1 with respect to absorbance.

FIG. 7 shows a variation of comparison value VCP1 with respect to absorbance at the wavelength of 665 nm. These VCP1 values were obtained by measuring a measurement solution, in which an aqueous solution sample, containing DCMU at a concentration of 0.1 ppb, was mixed with a photosynthetic sample of *Spirulina platensis*. In the case where the standard measurement solution is measured, a high correlation is seen between the absorbance and the light amount of delayed fluorescence at absorbances of no more than 0.5.

As shown in FIG. 7, as the photosynthetic sample density becomes higher than that at which OD=0.1, the VCP1 value (%) decreases. Meanwhile, the correlation between the light amount of delayed fluorescence and the photosynthetic sample density is maintained up to an absorbance of approximately 0.5. This indicates that even in the range of photosynthetic sample densities at which the light amount of delayed fluorescence is not attenuated by self-absorption, the biological growth inhibition factor detection sensitivity decreases when the photosynthetic sample density is comparatively high. The biological growth inhibition of the photosynthetic sample occurs as a result of chemical substances in the aqueous solution sample permeating and becoming absorbed into the photosynthetic sample and directly or indirectly interacting with specific target biomolecules. Thus, if excess photosynthetic sample (=target biomolecules) is present with respect to an ultralow concentration of a chemical substance, the effect of the chemical substance is lowered.

Returning now to FIG. 3, when the comparison values have been determined, storage unit 40 stores the comparison values (step S10) and display unit 42 displays the stored comparison values (step S11). Here, the display is carried out, for example, by graph display of the stored comparison values. It is also preferable to display comparison values concerning other aqueous solution samples that had been stored previously so that comparisons can be made. Lastly, by analyzing by comparing the displayed comparison values with comparison values of known substances, the biological growth inhibition factors in the aqueous solution sample are determined qualitatively and quantitatively (step S12, the above steps make up the third step or the assaying step). Details of the analysis and assay methods performed in step S12 shall be described later.

The light conditions during standing of the measurement solution in step S03 are preferably controlled to predetermined conditions for making measurements of high sensitivity in a stable manner. Also, because when a photosynthetic sample is moved from a bright location to a dark location, etc., the photosynthetic sample adapts to the environment gradually with the elapse of time, it is more preferable to make measurements of the delayed florescence after keeping the photosynthetic sample under certain light conditions before measurement or upon letting a predetermined time elapse after the light environment, in which the photosynthetic sample is placed, has been changed.

FIG. 8 shows examples of assay values in various cases that differ in the light intensity during standing of the measurement solution, with *Spirulina platensis* being used as the photosynthetic sample. In FIG. 8, graph (a) is a graph of CP1 at various light intensities, graph (b) is a graph of CP2 at various light intensities, and graph (c) is a graph of TP2 at various light intensities. As shown in FIG. 8, the CP1 measured from the measurement solution placed in a bright location under strong light before measurement is larger than those at other light intensities, the CP2 measured from the measurement solution placed under weak light, is larger than those at other light intensities, and the TP2 measured from the measurement solution placed under total darkness is larger than those at other light intensities. The delayed fluorescence emitted from the photosynthetic sample thus varies according to the light intensity in the standing state, and the light intensity in the standing state thus affects the measurement and assay results of the delayed fluorescence decay curve. Due to these reasons, it is important to control the light conditions during standing of the measurement solution in order to measure and assay maxima, minima, inflection points, and other characteristic points in the delayed fluorescence decay curve with good reproducibility and stability.

Also, to obtain measurement results of good reproducibility, the photosynthetic sample that is mixed with the measurement solution is preferably grown under predetermined culturing conditions. Such predetermined culturing conditions are preferably those of a certain light environment (for example, illumination wavelength, illumination intensity). More preferably, the culturing conditions are such that the photosynthetic sample is grown under a monochromatic light source and then restrained in proliferation by being stored under a low temperature and in total darkness or under a predetermined light illumination intensity (for example, a light illumination intensity of 1 μmol/m²/s).

Figure 9:
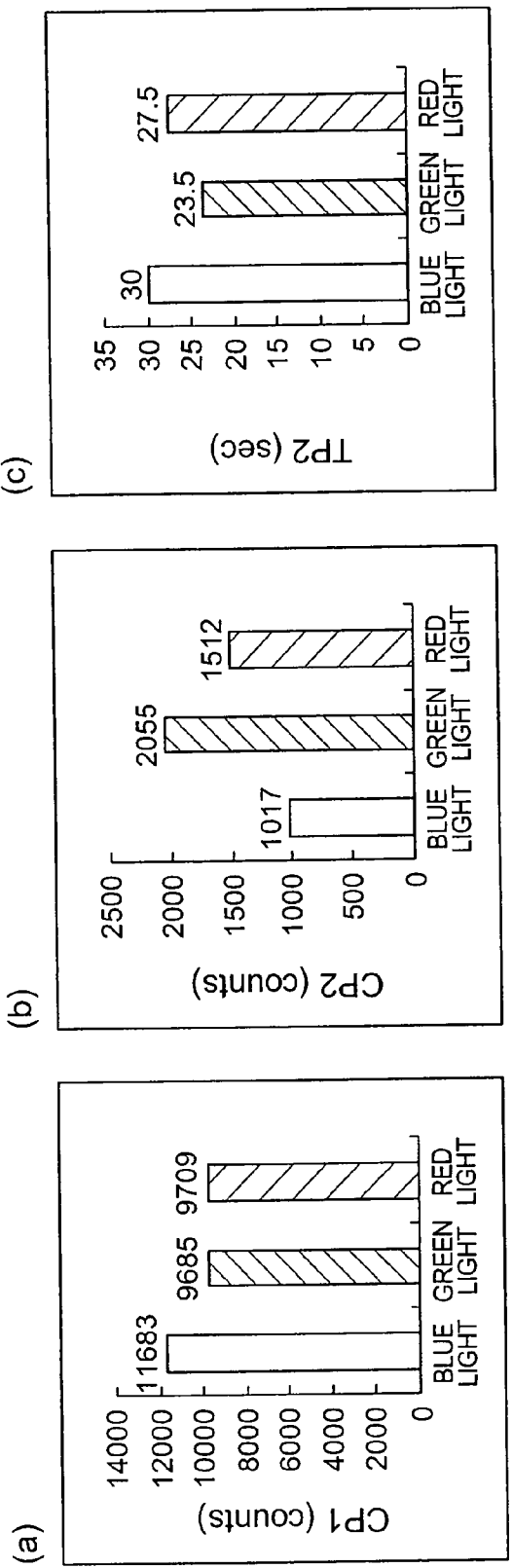
FIG. 9 shows (a) a graph of assay values CP1 for various wavelengths of light, (b) a graph of assay values CP2 for various wavelengths of light, and (c) a graph of assay values TP2 for various wavelengths of light.

FIG. 9 shows assay values for cases of using photosynthetic samples of *Spirulina platensis* grown under different light environments. In FIG. 9, graph (a) is a graph of CP1 when a culturing condition (wavelength of light) is varied, graph (b) is a graph of CP2 for various wavelengths of light, and graph (c) is a graph of TP2 for various wavelengths of light. Because the delayed fluorescence decay curve varies according to the light environment as shown in FIG. 9, the obtained assay values vary as well. Due to these reasons, it is important to grow the photosynthetic sample under predetermined culturing conditions to make high-sensitivity measurements that are standardized.

(Measurement of Known Substances)

The results of analyzing delayed fluorescence measurements made on aqueous solution samples, containing known chemical substances that act as biological growth inhibition factors, under standard measurement conditions shall now be described.

Figure 10:
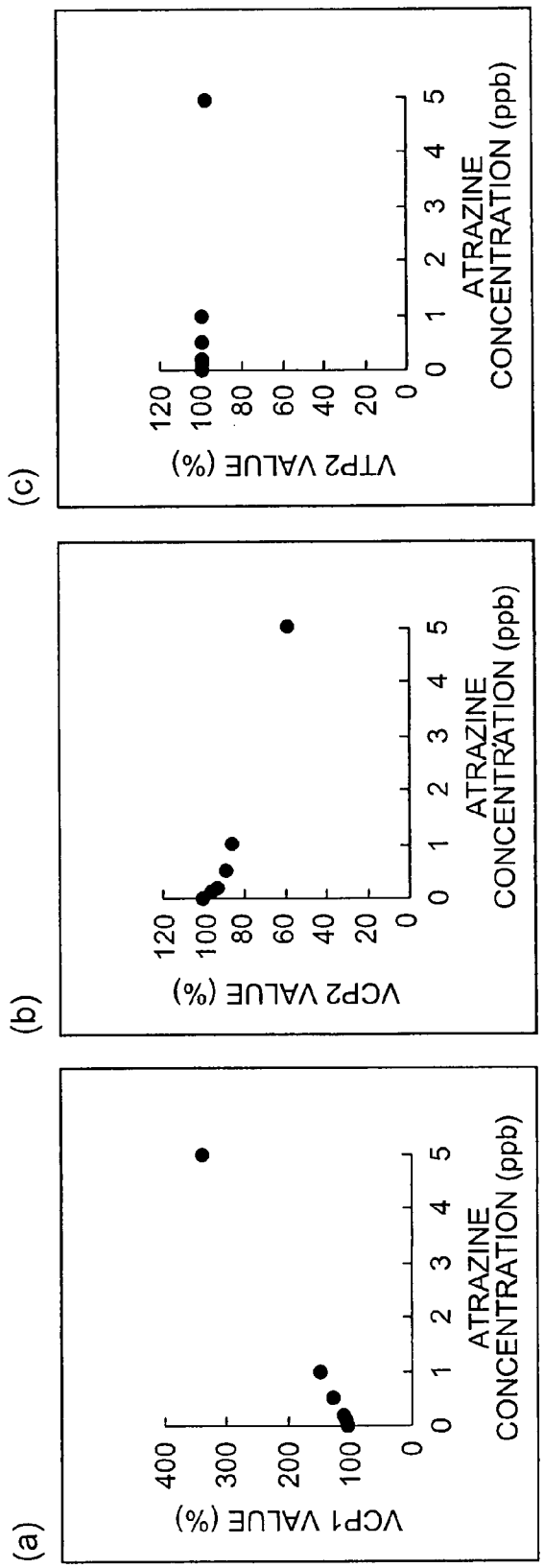
FIG. 10 shows (a) a graph of a variation of comparison value VCP1 with respect to atrazine concentration, (b) a graph of a variation of comparison value VCP2 with respect to atrazine concentration, and (c) a graph of a variation of comparison value VTP2 with respect to atrazine concentration.
Figure 11:
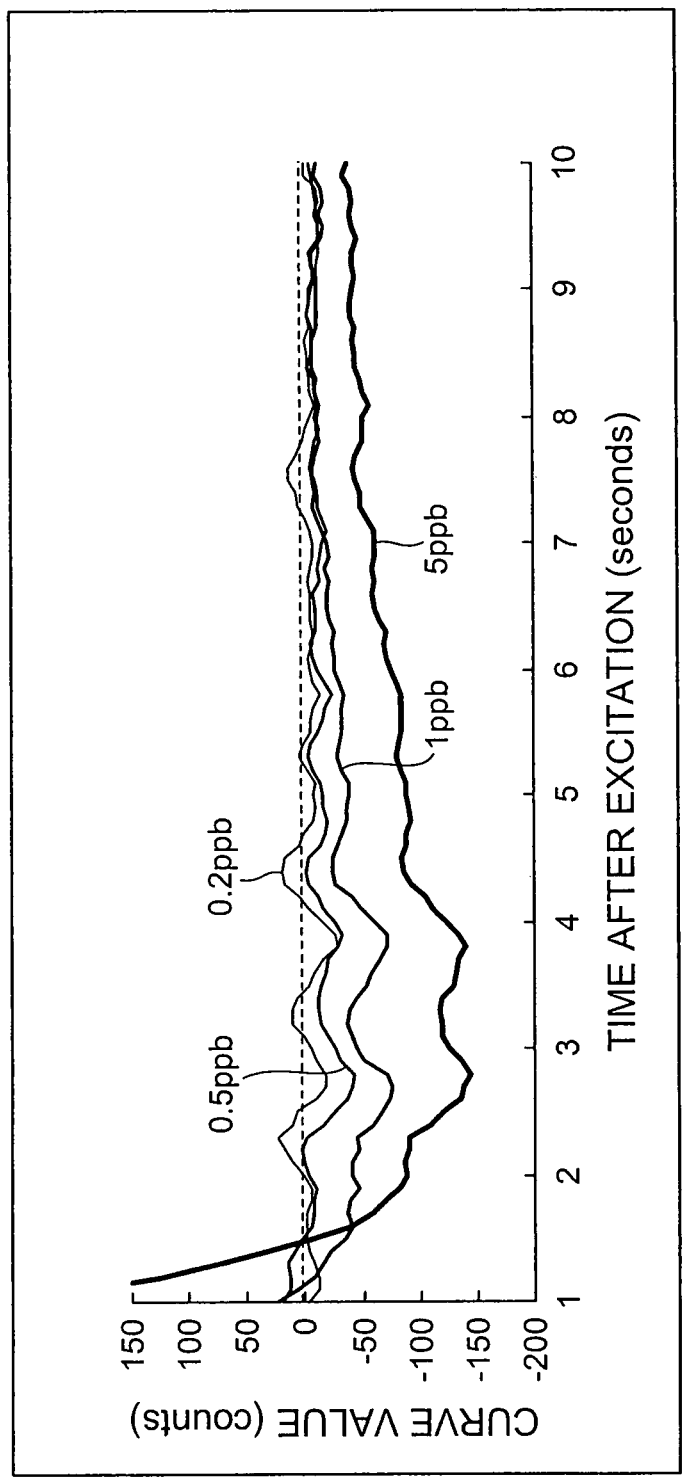
FIG. 11 is a graph of Curve values for various atrazine concentrations.

FIGS. 10 and 11 show graphs of comparison values computed for aqueous solution samples containing atrazine at various concentrations. In FIG. 10, graph (a) is a graph of a variation of the VCP1 value with respect to atrazine concentration, graph (b) is a graph of a variation of the VCP2 value with respect to atrazine concentration, and graph (c) is a graph of a variation of the VTP2 value with respect to atrazine concentration. FIG. 11 is a graph of Curve values for various atrazine concentrations. Though atrazine has been used as a hydrophobic herbicide that inhibits photosynthesis, this chemical substance has become subject to restrictions because it was found to exhibit endocrine disrupting actions and indicate teratogenic actions in frogs, etc., at a low concentration of approximately 20 μg/l. The atrazine concentrations indicated in the figures are concentrations in test measurement solutions, each adjusted to a final total volume of 3 ml.

As shown in FIG. 10, with an increase in the atrazine concentration, whereas the VCP1 value increases, the VCP2 value decreases. Also, as the atrazine concentration increases, the VTP2 value decreases slightly. Furthermore, FIG. 11 shows that the Curve value varies in the positive direction at around 1 second after excitation and then varies in the negative direction at around 3 to 4 seconds after excitation as the concentration becomes higher.

Figure 12:
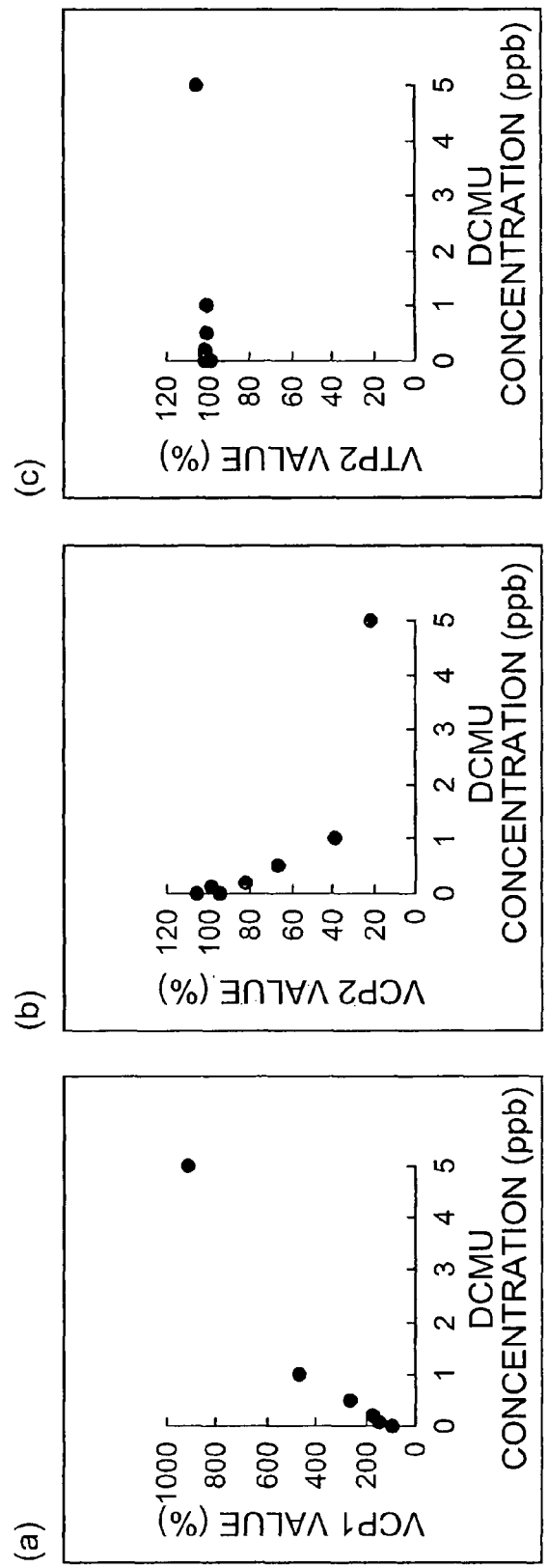
FIG. 12 shows (a) a graph of a variation of comparison value VCP1 with respect to DCMU concentration, (b) a graph of a variation of comparison value VCP2 with respect to DCMU concentration, and (c) a graph of a variation of comparison value VTP2 with respect to DCMU concentration.
Figure 13:
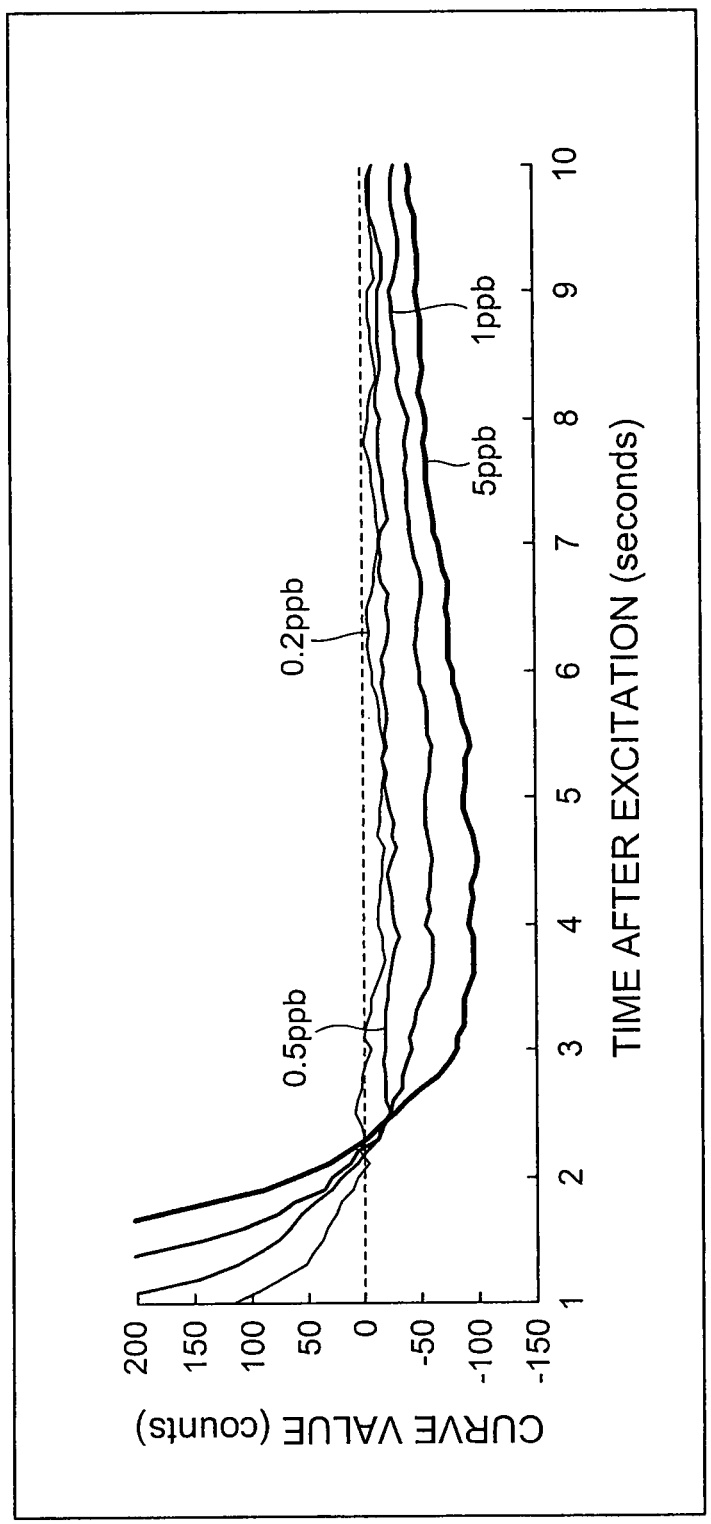
FIG. 13 is a graph of Curve values for various DCMU concentrations.

FIGS. 12 and 13 show graphs of comparison values computed for aqueous solution samples containing DCMU (diuron) at various concentrations. In FIG. 12, graph (a) is a graph of a variation of the VCP1 value with respect to DCMU concentration, graph (b) is a graph of a variation of the VCP2 value with respect to DCMU concentration, and graph (c) is a graph of a variation of the VTP2 value with respect to DCMU concentration. FIG. 13 is a graph of Curve values for various DCMU concentrations. As with atrazine, though DCMU (diuron) was used widely as a herbicide that inhibits photosynthesis, ill effects on living organisms have been indicated and the substance has become subject to restrictions. The DCMU concentrations indicated in the figures are concentrations in test measurement solutions, each adjusted to a final total volume of 3 ml.

As shown in FIG. 12, with an increase in the DCMU concentration, whereas the VCP1 value increases, the VCP2 value decreases. The VTP2 value hardly changes with an increase in the DCMU concentration. Furthermore, FIG. 13 shows that the Curve value varies in positive direction at around 1 second after excitation and then varies in the negative direction at around 3 to 5 seconds after excitation as the concentration becomes higher.

Figure 14:
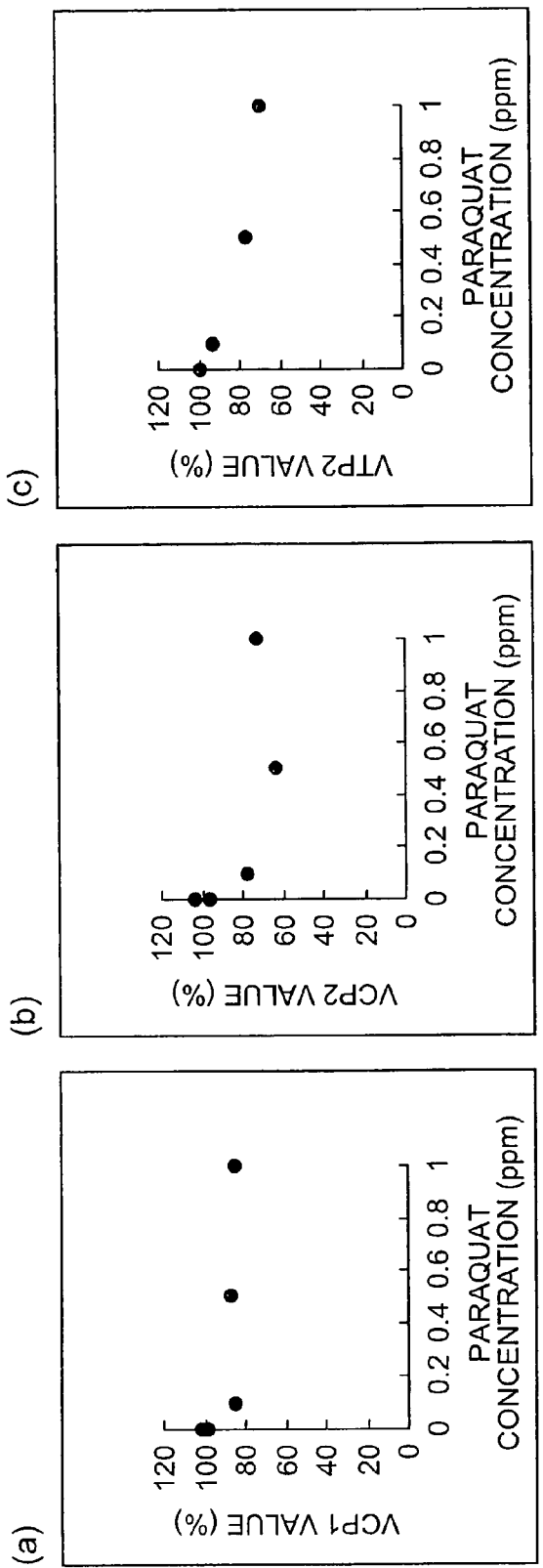
FIG. 14 shows (a) a graph of a variation of comparison value VCP1 with respect to paraquat concentration, (b) a graph of a variation of comparison value VCP2 with respect to paraquat concentration, and (c) a graph of a variation of comparison value VTP2 with respect to paraquat concentration.
Figure 15:
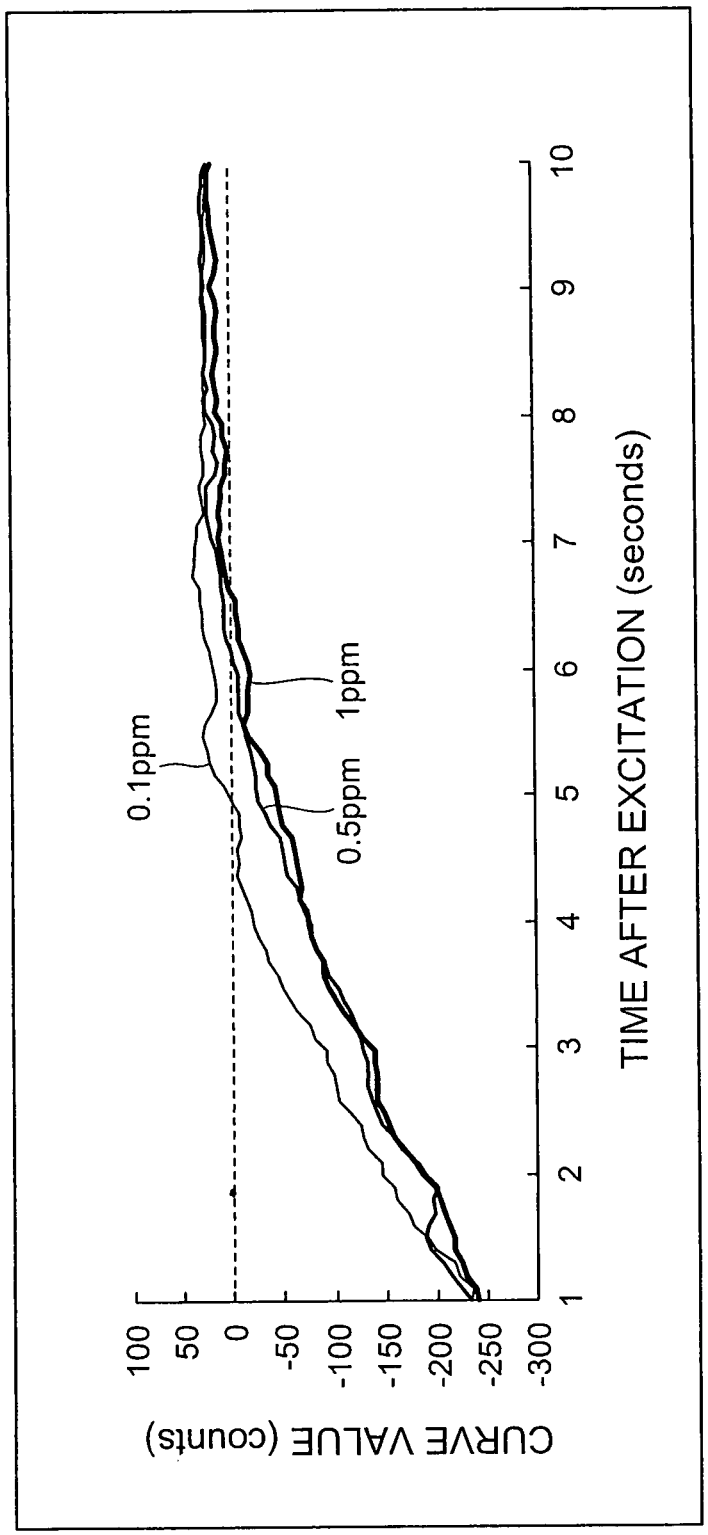
FIG. 15 is a graph of Curve values for various paraquat concentrations.

FIGS. 14 and 15 show graphs of comparison values computed for aqueous solution samples containing paraquat at various concentrations. In FIG. 14, graph (a) is a graph of a variation of the VCP1 value with respect to paraquat concentration, graph (b) is a graph of a variation of the VCP2 value with respect to paraquat concentration, and graph (c) is a graph of a variation of the VTP2 value with respect to paraquat concentration. FIG. 15 is a graph of Curve values for various paraquat concentrations. Paraquat is used as a herbicide and disrupts electron transfer in biological reaction upon being taken into cells and damages cells by generating reactive oxygen. The paraquat concentrations indicated in the figures are concentrations in test measurement solutions, each adjusted to a final total volume of 3 ml.

As shown in FIG. 14, with an increase in the paraquat concentration, the VCP2 value and the VTP2 value decrease. However, such a decrease becomes imperceptive at high paraquat concentrations. Also, at low paraquat concentration, the VCP1 value decreases slightly as the paraquat concentration increases. Furthermore, FIG. 15 shows that the Curve value varies in the negative direction at around 1 to 4 seconds after excitation as the concentration becomes higher.

Figure 16:
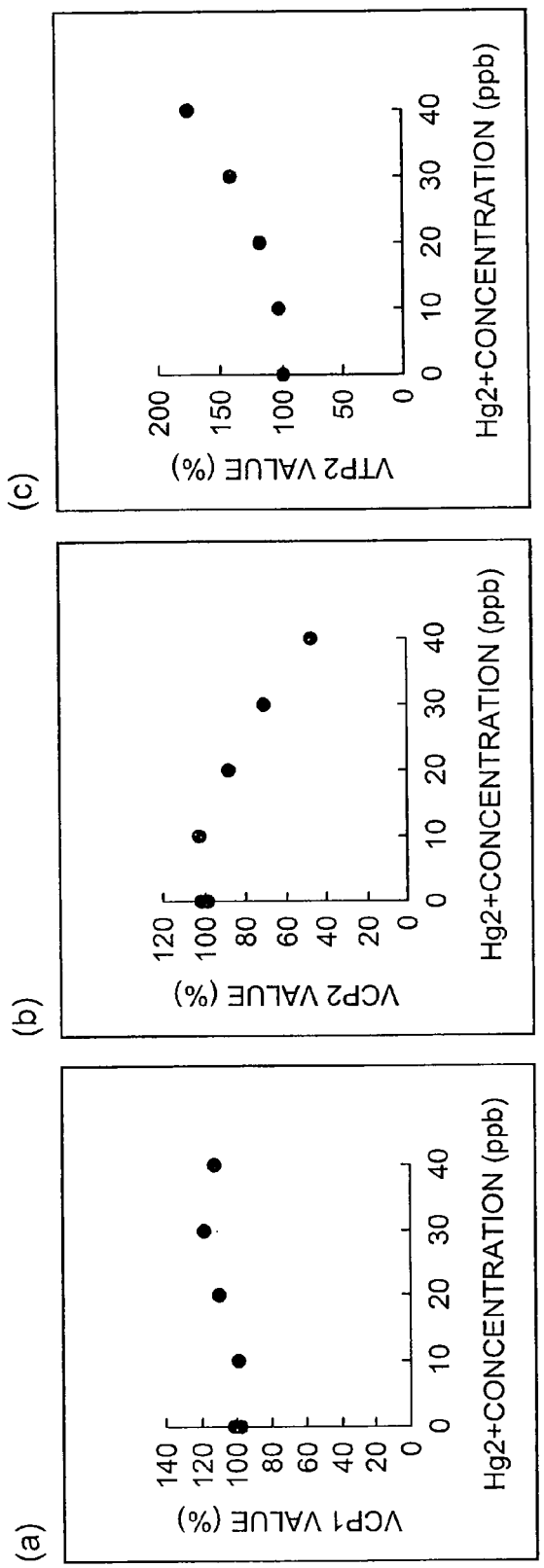
FIG. 16 shows (a) a graph of a variation of comparison value VCP1 with respect to inorganic mercury concentration, (b) a graph of a variation of comparison value VCP2 with respect to inorganic mercury concentration, and (c) a graph of a variation of comparison value VTP2 with respect to inorganic mercury concentration.
Figure 17:
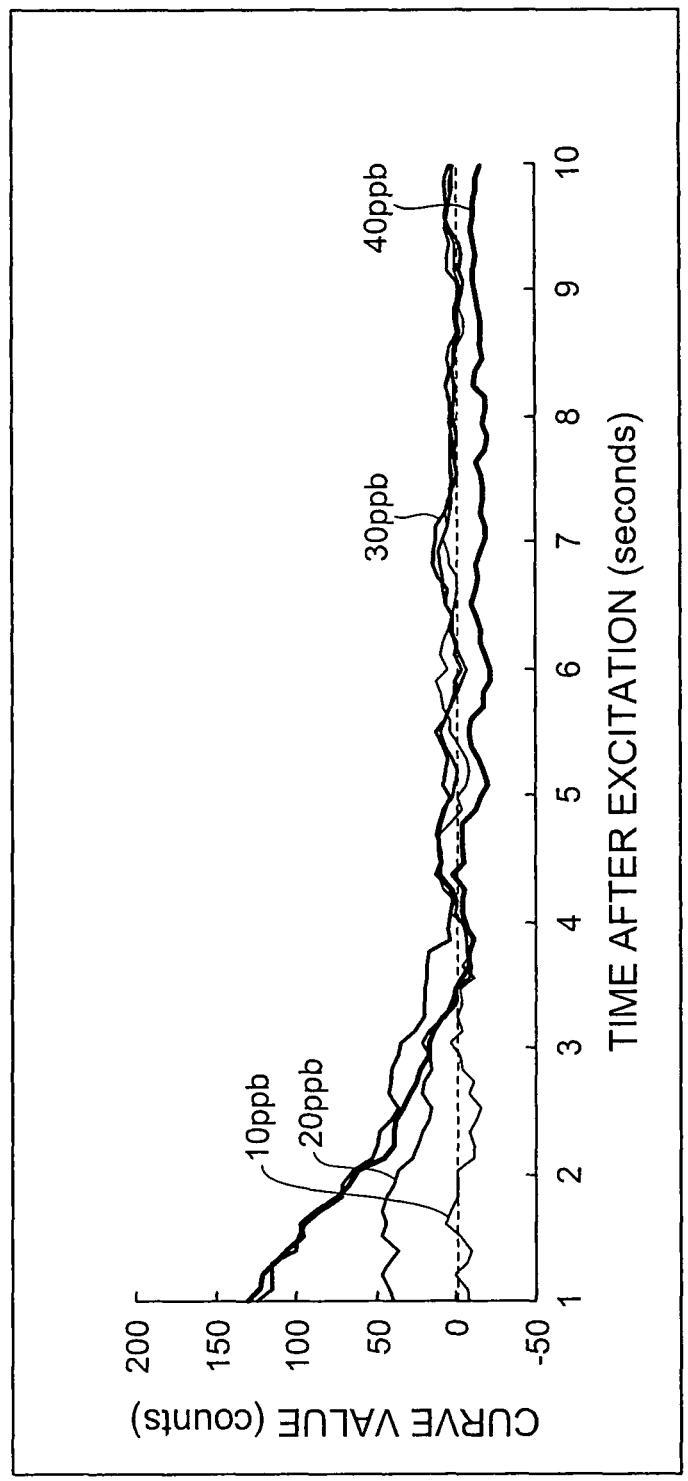
FIG. 17 is a graph of Curve values for various inorganic mercury concentrations.

FIGS. 16 and 17 show graphs of comparison values computed for aqueous solution samples containing inorganic mercury at various concentrations. In FIG. 16, graph (a) is a graph of a variation of the VCP1 value with respect to inorganic mercury concentration, graph (b) is a graph of a variation of the VCP2 value with respect to inorganic mercury concentration, and graph (c) is a graph of a variation of the VTP2 value with respect to inorganic mercury concentration. FIG. 17 is a graph of Curve values for various inorganic mercury concentrations. Inorganic mercury is a substance that exhibits toxicity not only to photosynthetic samples but to cells in general. The inorganic mercury concentrations indicated in the figures are mercury ion concentrations in test measurement solutions, each prepared as a mercury chloride solution and adjusted to a final total volume of 3 ml.

As shown in FIG. 16, with an increase in the inorganic mercury concentration, whereas the VTP2 value increases, the VCP2 value decreases. Also, though the VCP1 value does not change much with an increase in the inorganic mercury concentration at low inorganic mercury concentration, at high inorganic mercury concentration, the VCP1 value increases with an increase in the inorganic mercury concentration. Furthermore, FIG. 17 shows that the Curve value varies in the positive direction at around 1 to 2 seconds after excitation as the concentration becomes higher.

Figure 18:
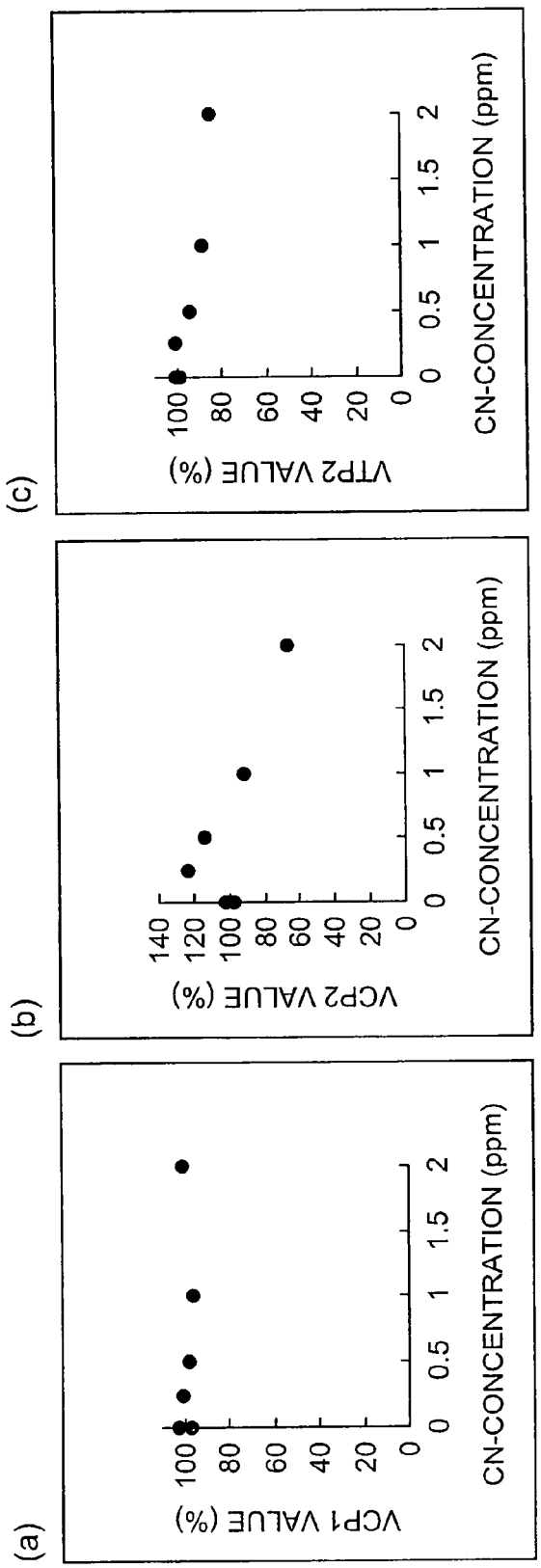
FIG. 18 shows (a) a graph of a variation of comparison value VCP1 with respect to free cyanide concentration, (b) a graph of a variation of comparison value VCP2 with respect to free cyanide concentration, and (c) a graph of a variation of comparison value VTP2 with respect to free cyanide concentration.
Figure 19:
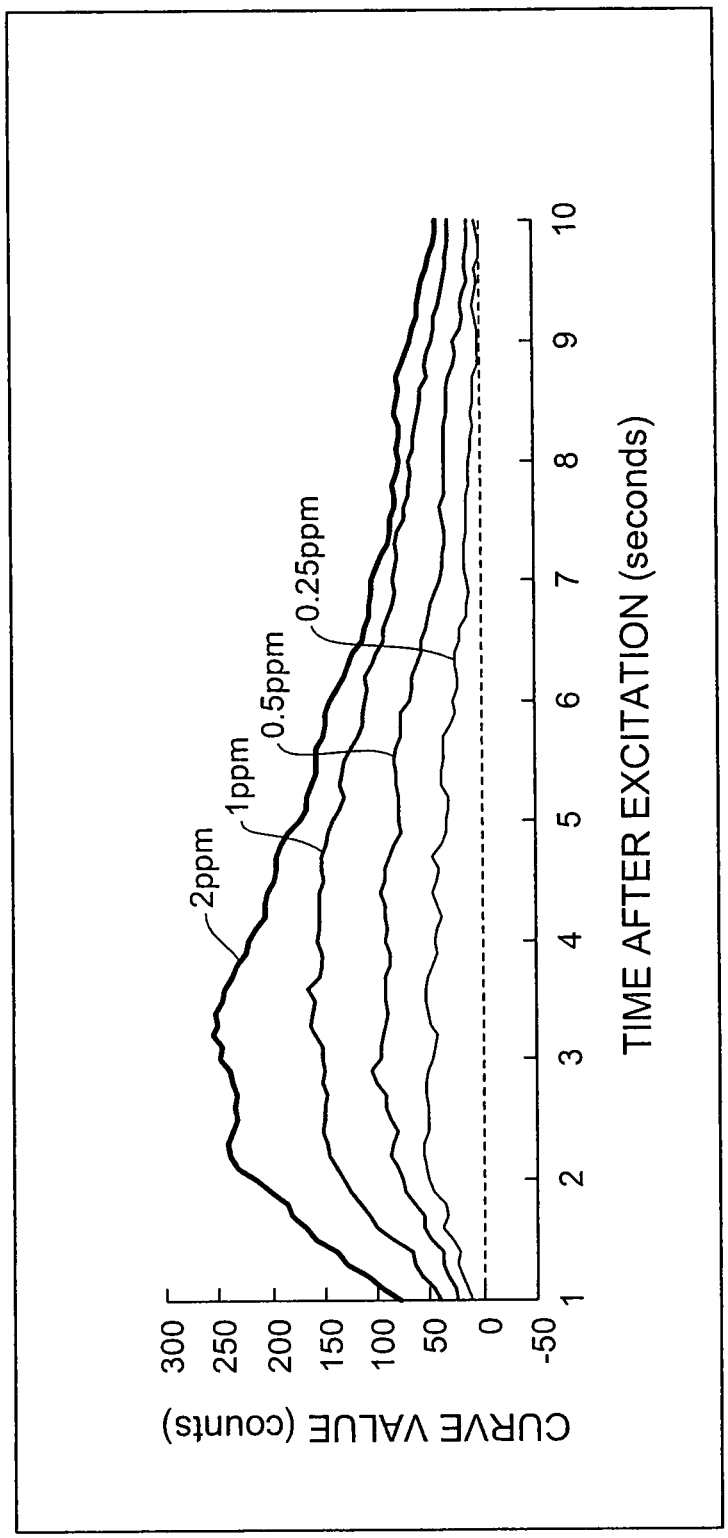
FIG. 19 is a graph of Curve values for various free cyanide concentrations.

FIGS. 18 and 19 show graphs of comparison values computed for aqueous solution samples containing free cyanide at various concentrations. In FIG. 18, graph (a) is a graph of a variation of the VCP1 value with respect to free cyanide concentration, graph (b) is a graph of a variation of the VCP2 value with respect to free cyanide concentration, and graph (c) is a graph of a variation of the VTP2 value with respect to free cyanide concentration. FIG. 19 is a graph of Curve values for various free cyanide concentrations. Free cyanide is a substance that exhibits toxicity not only to photosynthetic samples but to cells in general. The free cyanide concentrations indicated in the figures are cyanide ion concentrations in test measurement solutions, each prepared as a potassium cyanide solution and adjusted to a final total volume of 3 ml.

As shown in FIG. 18, though the VTP2 value and the VCP2 value hardly change as the free cyanide concentration increases at low free cyanide concentration, these values decrease as the free cyanide concentration increases at high free cyanide concentration. Also, the VCP1 value hardly changes with an increase in the free cyanide concentration. Furthermore, FIG. 19 shows that the Curve value varies in the positive direction as the concentration becomes higher, and this variation is concentrated at around 2 to 4 seconds after excitation.

Figure 20:
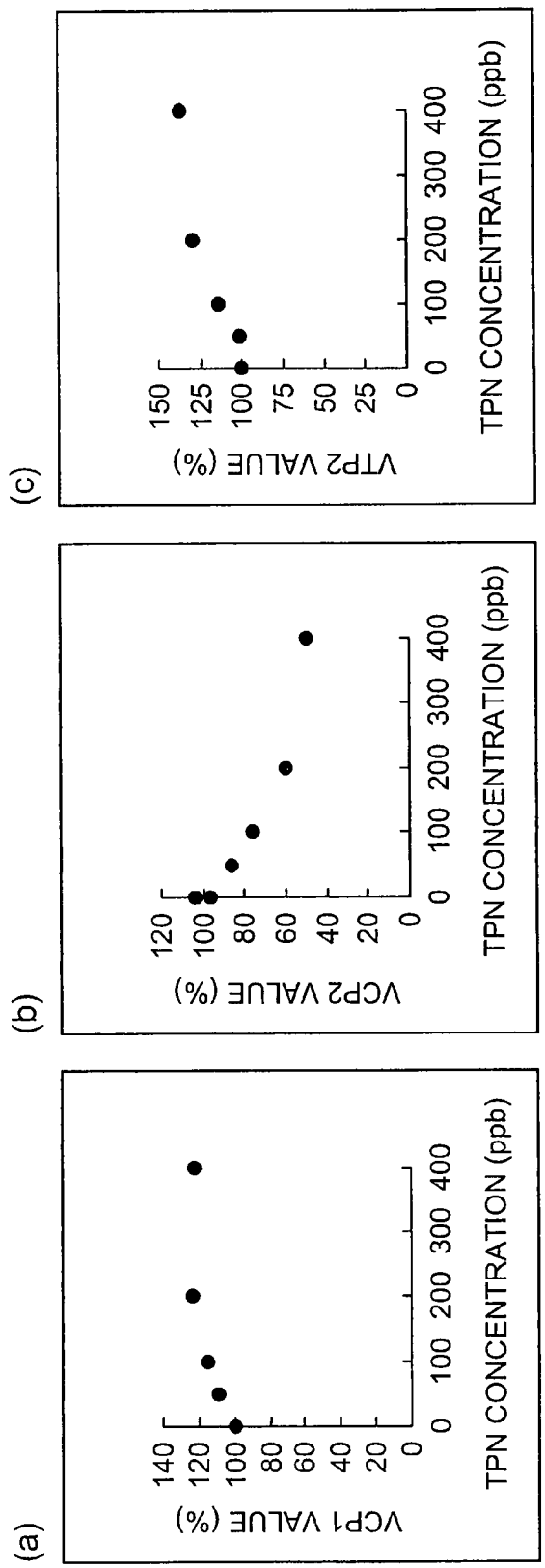
FIG. 20 shows (a) a graph of a variation of comparison value VCP1 with respect to TPN concentration, (b) a graph of a variation of comparison value VCP2 with respect to TPN concentration, and (c) a graph of a variation of comparison value VTP2 with respect to TPN concentration.
Figure 21:
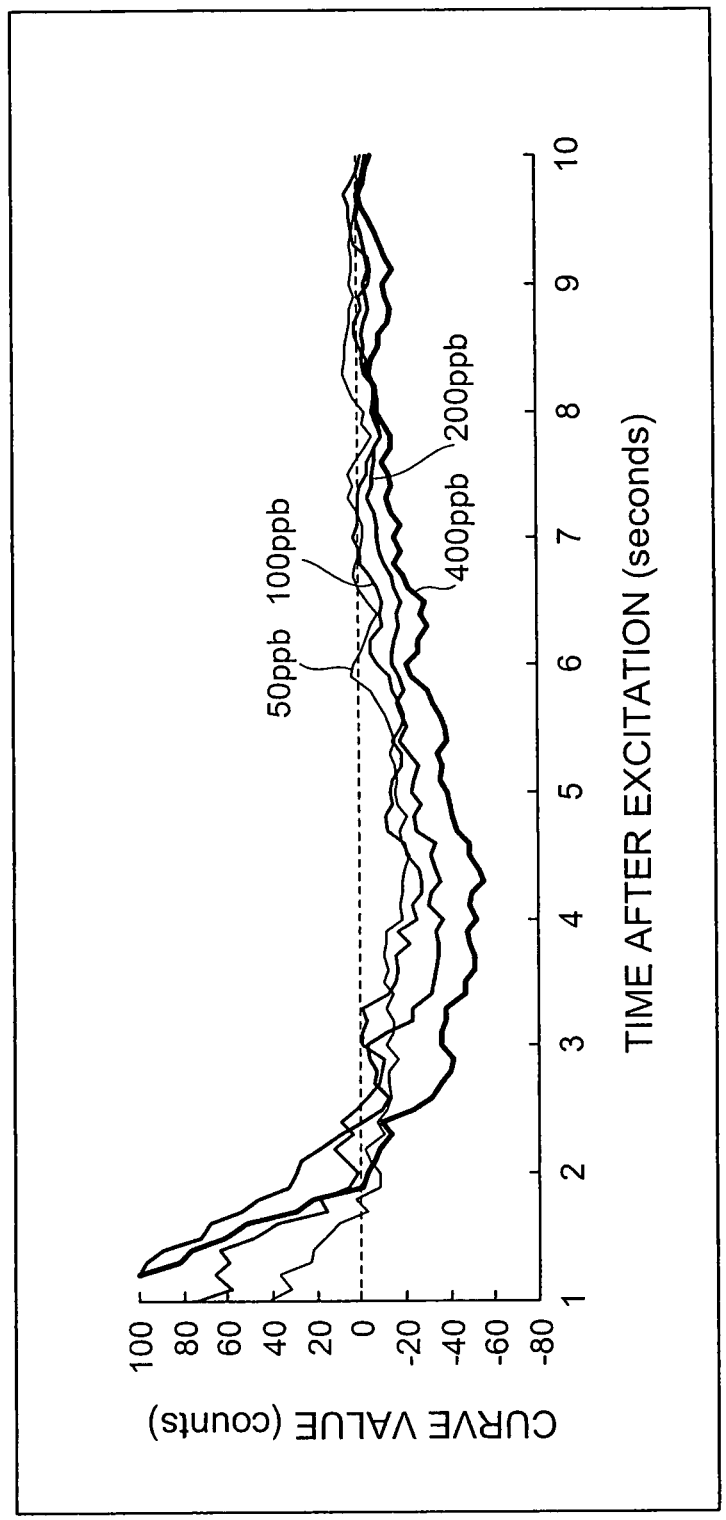
FIG. 21 is a graph of Curve values for various TPN concentrations.

FIGS. 20 and 21 show graphs of comparison values computed for aqueous solution samples containing TPN at various concentrations. In FIG. 20, graph (a) is a graph of a variation of the VCP1 value with respect to TPN concentration, graph (b) is a graph of a variation of the VCP2 value with respect to TPN concentration, and graph (c) is a graph of a variation of the VTP2 value with respect to TPN concentration. FIG. 21 is a graph of Curve values for various TPN concentrations. TPN is a component that is contained in agricultural chemicals, etc., that exhibit an antiseptic action and is a chemical substance that acts not on photosynthesis but on respiratory metabolism by deactivating an enzyme involved in the production of ATP, which is an energy source for cells. The TPN concentrations indicated in the figures are TPN concentrations in test measurement solutions, each prepared by diluting an antiseptic, having TPN as the sole main agent, and adjusting to a final total volume of 3 ml.

As shown in FIG. 20, with an increase in the TPN concentration, whereas the VCP1 value and the VTP2 value increase, the VCP2 value decreases. Also, FIG. 21 shows that the Curve value varies in the positive direction at around 1 second after excitation and then varies in the negative direction at around 3 to 5 seconds after excitation as the concentration becomes higher.

TPN is a major antiseptic that is subject to restrictions of residual agricultural chemicals on vegetables, and a legal regulation concentration is 1 ppm. The application concentration in a major commercially-available antiseptic having TPN as the main agent is 400 ppm. The detection sensitivity of the present method is such as to enable detection at a concentration of approximately $1/10000$ of the application concentration. TPN of no more than the regulation standard amount can thus be detected adequately by obtaining an aqueous solution sample from a surface of a vegetable.

(Analysis and Assay of Biological Growth Inhibition Factors)

In measuring an actual aqueous solution sample, a plurality of biological growth inhibition factors may be present at the same time in the sample. With the delayed fluorescence decay curve obtained by the biological growth inhibition factor assay method, the effects due to the various growth inhibition factors are separated in time and are exhibited in an additive manner in correspondence to the biological growth inhibition factors. Thus, when a plurality of biological growth inhibition factors are present, each factor can be estimated separately and the variations can be evaluated in an integrated form as well. Qualitative assay and quantitative assay of the biological growth inhibition factors are thus carried at the same time.

When biological growth inhibition factors that differ in type are present in an aqueous solution sample, for example, when DCMU and inorganic mercury are present, the comparison values, which, among the comparison values used in the present embodiment, exhibit major variations, are the VCP1 value in the case of DCMU and the VCP2 and VTP2 values in the case of inorganic mercury. When biological growth inhibition factors, which differ in the comparison values that exhibit variations in the delayed fluorescence decay curve, are contained at the same time, the overall variations of comparison values are exhibited in an additive manner.

FIG. 22 shows comparison values, VCP1, VCP2, and VTP2, obtained from a test measurement solution "DCMU," containing DCMU as the biological growth inhibition factor at a concentration of 0.1 ppb, a test measurement solution "Hg2+," containing mercury ion as the biological growth inhibition factor at a concentration of 20 ppb, and a test measurement solution "DCMU+Hg," containing DCMU at a concentration of 0.1 ppb and mercury ion at a concentration of 20 ppb. In FIG. 22, graph (a) is a graph of the VCP1 values of the respective test measurement solutions, graph (b) is a graph of the VCP2 values of the respective test measurement solutions, and graph (c) is a graph of the VTP2 values of the respective test measurement solutions.

As shown in the graph (a) of FIG. 22, the VCP1 value is 116.0 for "DCMU," for which the VCP1 value is the assay value that exhibits a major variation, 129.6 for "DCMU+ Hg," which contains DCMU and mercury ion, and 104.1 for "Hg2+," which contains only mercury ion, and it can thus be understood that the variation of the VCP1 value is large when DCMU is contained. Also, as shown in the graph (b) of FIG. 22, the VCP2 value is 59.9 for "Hg2+," for which the VCP2 value is the comparison value that exhibits a major variation, 44.9 for "DCMU+Hg," which contains DCMU and mercury ion, and 88.0 for "DCMU," which contains only DCMU, and it can thus be understood that the variation of the CP2 value is large when mercury ion is contained. Furthermore, as shown in the graph (c) of FIG. 22, the VTP2 value is 144.9 for "Hg2+," for which the VTP2 value is the comparison value that exhibits a major variation, 149.9 for "DCMU+Hg," which contains DCMU and mercury ion, and 100.0 for "DCMU," which contains only DCMU, and it can thus be understood that the variation of the TP2 value is large when mercury ion is contained.

The above results show that with "DCMU+Hg," which contains DCMU and mercury ion, variations appear in the VCP1 value, which exhibits a major variation with DCMU, and in the comparison values, VCP2 and VTP2, which exhibit major variations with mercury ion, and that DCMU and mercury ion are contained simultaneously can be measured at the same time.

Meanwhile, when biological growth inhibition factors of the same type are present in an aqueous solution sample, for example, when atrazine and DCMU are present, the comparison value, which, among the comparison values used in the present embodiment, exhibits a major variation, is the VCP1 value. When biological growth inhibition factors, for which the comparison value that exhibits a variation in the delayed fluorescence decay curve is the same, are contained at the same time, the overall variations of comparison values are exhibited in an additive manner.

FIG. 23 shows comparison values, VCP1, VCP2, and VTP2, obtained from a test measurement solution "atrazine," containing atrazine as the biological growth inhibition factor at a concentration of 0.2 ppb, a test measurement solution "DCMU," containing DCMU as the biological growth inhibition factor at a concentration of 0.1 ppb, and a test measurement solution "atrazine+DCMU," containing DCMU at a concentration of 0.1 ppb and atrazine at a concentration of 0.2 ppb. In FIG. 23, graph (a) is a graph of the VCP1 values of the respective test measurement solutions, graph (b) is a graph of the VCP2 values of the respective test measurement solutions, and graph (c) is a graph of the VTP2 values of the respective test measurement solutions.

As shown in the graph (a) of FIG. 23, the VCP1 value is 106.4 for atrazine, 125.6 for "DCMU," and 132.2 for "atrazine+DCMU," and it can thus be understood that VCP1 increases additively when atrazine and DCMU are contained at the same time. Also, as shown in the graph (b) of FIG. 23, the VCP2 value is 90.0 for "atrazine," 84.6 for "DCMU," and 86.0 for "atrazine+DCMU," and it can thus be understood that a large variation is not seen. Furthermore, as shown in the graph (c) of FIG. 23, the VTP2 value is 100.0 for "atrazine," 101.5 for "DCMU," and 100.0 for "atrazine+DCMU," and it can thus be understood that a large variation is not seen.

The above results show that with "atrazine+DCMU," which contains atrazine and DCMU, the VCP1 value, which is the comparison value that exhibits a major variation with respect to both substances, increases in an additive manner. Since biological growth inhibition factors of the same type thus influence the delayed fluorescence measurement results in an additive manner, comprehensive biological growth inhibition factor assay results are obtained for chemical substances that are biological growth inhibition factors of the same type.

(Biological Growth Inhibition Factor Assay Kit)

A biological growth inhibition factor assay kit according to this invention shall now be described in detail. The biological growth inhibition factor assay kit can be used to put the above-described biological growth inhibition factor assay method into practice in a simple manner. The biological growth inhibition factor assay kit includes a concentrated photosynthetic sample, which is mixed with an aqueous solution sample or a standard sample, an adjusting solution, containing a concentrated salt mixture and nutrient salts for adjusting the salt concentration and the pH of the aqueous solution sample or standard sample into which the photosynthetic sample has been mixed, and a mixing means that mixes the aqueous solution sample with the photosynthetic sample and with the adjusting solution in a separated manner.

Here, preferably, one of either or both of the abovementioned concentrated photosynthetic sample and the adjusting solution contains a stabilizer that is necessary for spatial stabilization of the photosynthetic sample. In a case where the concentrated photosynthetic sample contains a stabilizer, a stabilizer that will not have an ill effect on the photosynthetic sample in the concentrated state is used. Also, a stabilizer that does not inhibit the actions, on the photosynthetic sample, of the biological growth inhibition factors in the aqueous solution sample by adsorption, decomposition, etc., is preferably used. Agarose and other polysaccharides and macromolecular polymers can be cited as examples of stabilizers.

As the mixing means, a liquid sampling container of an arbitrary shape may be used as long as the photosynthetic sample and the adjusting solution can be mixed separately with the aqueous solution sample in the liquid sampling container.

Figure 24:
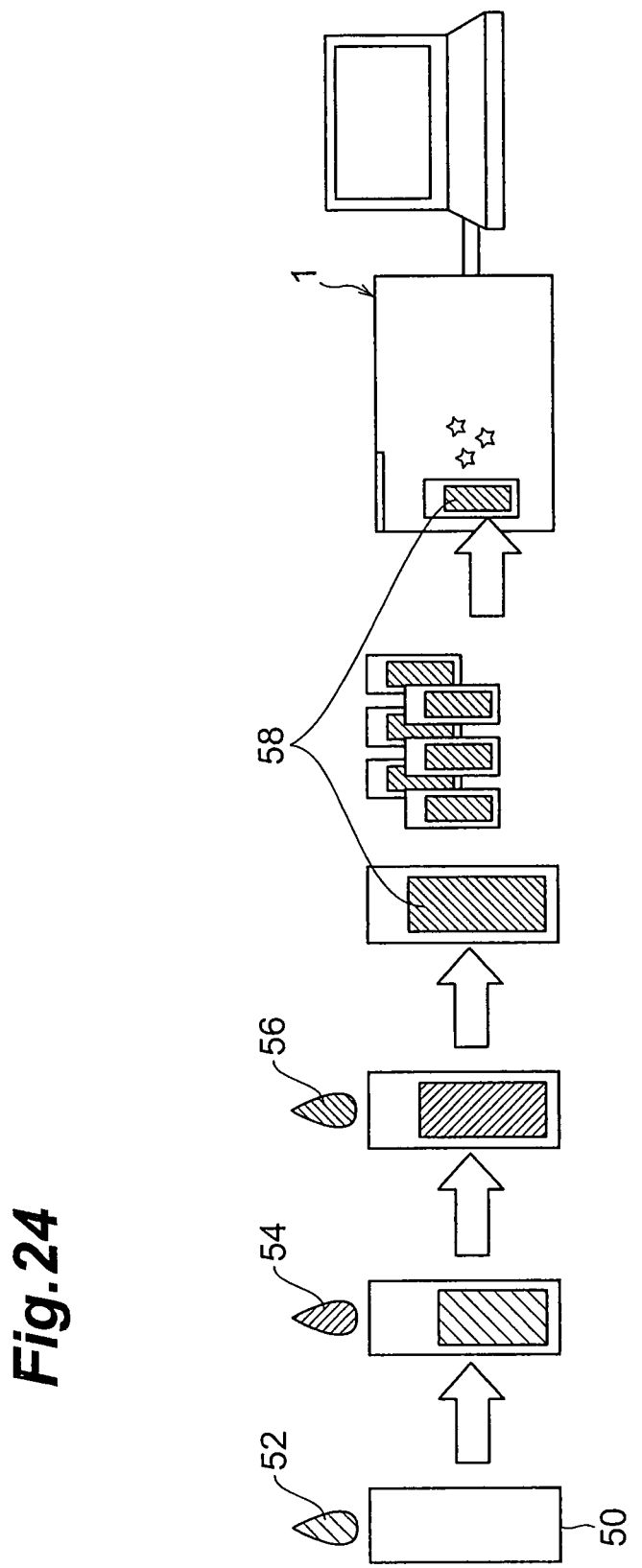
FIG. 24 is a diagram of procedures performed to measure delayed fluorescence using a biological growth inhibition factor assay kit according to an embodiment of this invention.

FIG. 24 is a diagram of procedures performed to measure delayed fluorescence using such a biological growth inhibition factor assay kit. As shown in this figure, a predetermined amount of an aqueous solution sample 52 is sampled in a predetermined liquid sampling container 50, and thereafter, an adjusting solution 54 is mixed so that the salt concentration and the pH are within predetermined ranges. A concentrated photosynthetic sample 56 is then mixed into liquid sampling container 50. Then, after letting test measurement solution 58, which has thus been prepared inside liquid sampling container 50, stand, liquid sampling container 50 is housed in delayed fluorescence measuring device 1 to perform measurement of the light amount of delayed fluorescence.

As the liquid sampling container, a syringe, dropper, or other container that enables a predetermined amount of an aqueous solution sample to be sampled by suction, etc., is preferably used. Also, preferably, the adjusting solution and the concentrated photosynthetic sample, either or both containing a stabilizer, are housed in separated states in the liquid sampling container. In this case, because the adjusting solution, the photosynthetic sample, and the stabilizer can be mixed in a single action in the process of sampling the aqueous solution sample, the measurement can be performed in a simpler manner.

Also, preferably, the adjusting solution and the concentrated photosynthetic sample are held at positions such that when the aqueous solution sample is sucked in it is first mixed with the adjusting solution and then with the concentrated photosynthetic sample. With such an arrangement, even if the salt concentration and the pH of the aqueous solution sample are within ranges that may affect the photosynthetic sample, the effect on the photosynthetic sample can be reduced by mixing the photosynthetic sample after adjustment with the adjusting solution.

Figure 25:
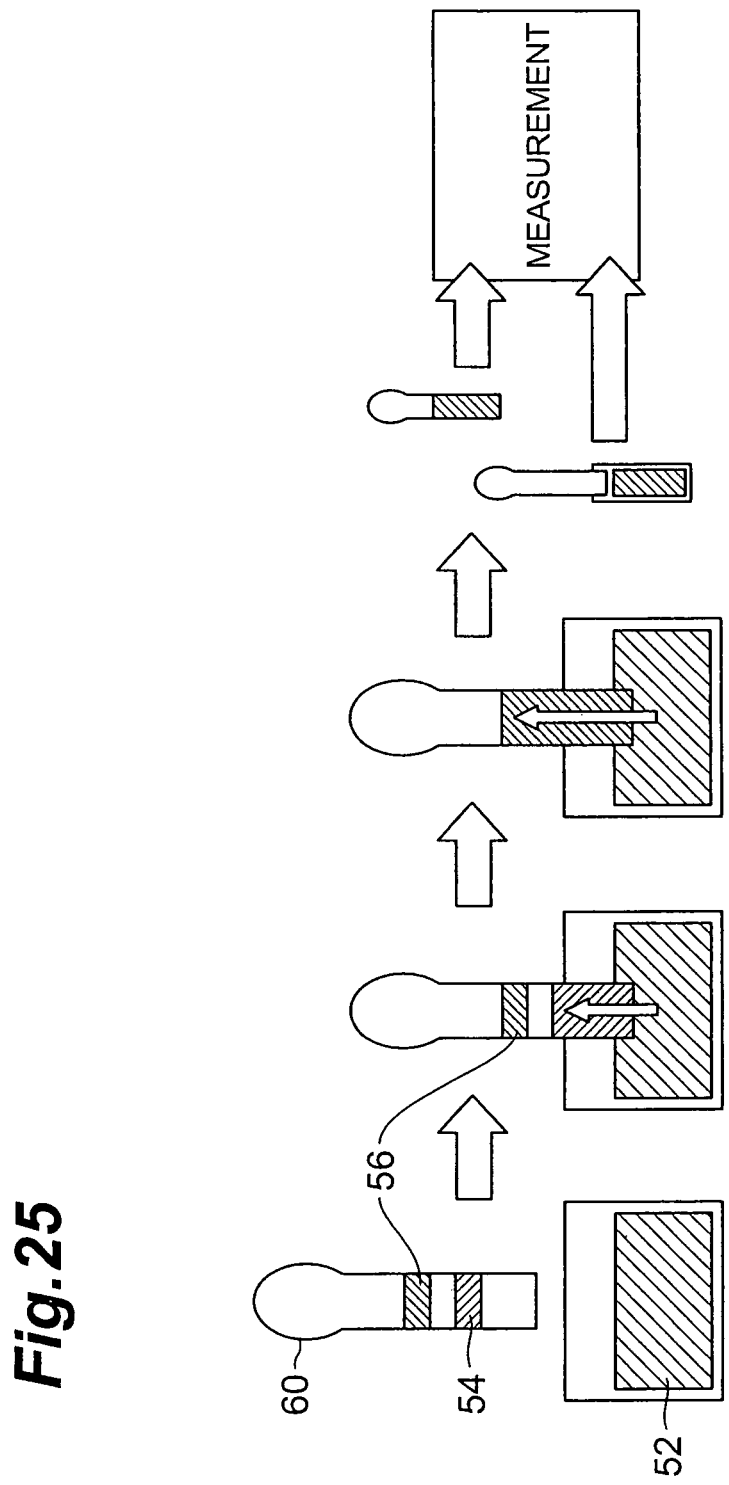
FIG. 25 is a diagram of procedures performed to measure delayed fluorescence using a biological growth inhibition factor assay kit according to another embodiment of this invention.

FIG. 25 is a diagram of procedures performed to measure delayed fluorescence using a dropper-type biological growth inhibition factor assay kit. As shown in this figure, an adjusting solution 54 and a concentrated photosynthetic sample 56 are contained in a vertically separated manner inside a dropper-type liquid sampling container 60. To hold the adjusting solution and the concentrated photosynthetic sample in a separated manner inside liquid sampling container 60, liquid sampling container 60 itself may be provided with walls, solution pockets or other separating means. From the standpoint of simplifying the structure and reducing the cost of liquid sampling container 60, one of either or both of the adjusting solution and the concentrated photosynthetic sample may be made to have a high viscosity by the containing of a concentrated gelling agent or other stabilizer.

With this liquid sampling container 60, an aqueous solution sample 52 is sampled by suction to the position at which adjusting solution 54 is contained and the aqueous solution sample is mixed once with adjusting solution 54. Aqueous solution sample 52 is then sampled by suction into liquid sampling container 60 until a predetermined amount is reached and mixed with concentrated photosynthetic sample 56. The test measurement solution that is thus prepared inside liquid sampling container 60 is then left to stand, and liquid sampling container 60 is then housed in delayed fluorescence measuring device 1 to perform measurement of the light amount of delayed fluorescence.

Because by using the above-described biological growth inhibition factor assay kit, the adjusting solution, which contains salts at high concentrations, and the photosynthetic sample are mixed separately with the aqueous solution sample, the effects of the salts on the photosynthetic sample can be minimized to prevent death and destruction of the photosynthetic sample due to osmotic pressure differences, etc.

Actions and effects of the biological growth inhibition factor assay method according to the embodiment of this invention shall now be described.

With the biological growth inhibition factor assay method, the decay curve of the delayed fluorescence emitted from the photosynthetic sample that is mixed with the aqueous solution sample to be assayed and the decay curve of the delayed fluorescence emitted from the photosynthetic sample in the solution in which biological growth inhibition factors are not present are measured. By then evaluating peaks, inflection points, and other characteristic points from the respective decay curves and comparing the two curves, the effect of the biological growth inhibition factors on the photosynthetic sample are assayed. By performing such assay, a plurality of chemical substances can be analyzed qualitatively and quantitatively simultaneously and at high precision. Also, by assaying by measuring the light amount of delayed fluorescence, the measurement time can be shortened as a whole.

This invention is not restricted to the above-described embodiment and, for example, though in the biological growth inhibition factor assay method according to the embodiment, the light conditions during standing of the measurement solution were controlled at predetermined conditions, the comparison values may instead be evaluated upon changing the light conditions variously each time the measurement solution is measured.

Figure 26:
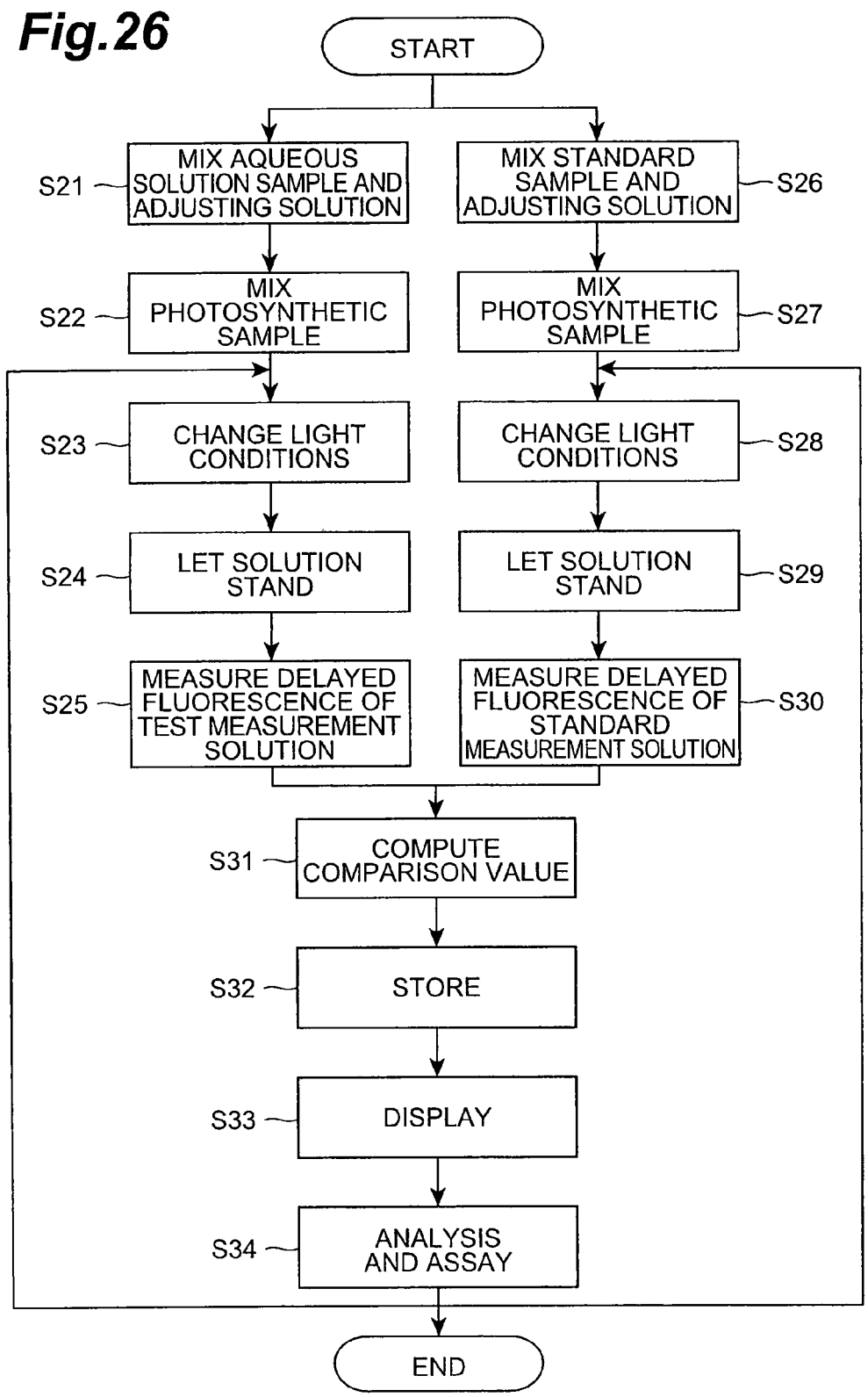
FIG. 26 is a flowchart of procedures of a biological growth inhibition factor assay method according to another embodiment of this invention.

FIG. 26 is a flowchart of procedures of a biological growth inhibition factor assay method of such a case. To mainly describe the points of difference with respect to the procedures of FIG. 3, first, the test measurement solution and the standard measurement solution are prepared in the same manner as in step S01, step S02, step S05, and step S06 (step S21 to step S22 and step S26 to step S27). The light conditions of the initial standing are then set (step S23 and step S28). Thereafter, the test measurement solution and the standard measurement solution are left standing for a predetermined standing time under the set light conditions (step S24 and step S29). Comparison values are then computed from the light amounts of delayed fluorescence measured and the comparison values are evaluated in the same manner as in step S04 and steps S08 to S12 in FIG. 3 (step S25 and steps S30 to S34). After evaluation, step S23 and step S28 are returned to, and after changing the previously set light conditions, the comparison values are computed again, and the changes of the comparison values according to the light conditions are evaluated repeatedly. The measurement solutions may be prepared anew for each set of light conditions.

As the light conditions during standing, monochromatic light in the visible range or combinations of such monochromatic light, or infrared light, ultraviolet light, or other light may be used monochromatically or in combination to measure changes of biological growth inhibition factors more finely.

FIG. 27 shows graphs of examples of comparison values computed for various light conditions during standing. In FIG. 27, graph (a) is a graph of comparison values concerning TPN for various light conditions, and graph (b) is a graph of comparison values concerning inorganic mercury for various light conditions. Here, as the light conditions during standing, the light illuminated onto the measurement solution was changed among the three types of white fluorescent lamp, green monochromatic light (wavelength: 530 nm), and red monochromatic light (wavelength: 665 nm). The light amount of each type of illumination light was set to 1.5 $\mu mol/m^2/s$. As the comparison values, the VCP1 value, the VCP2 value, and the VTP2 value were computed.

As shown in the graph (a) of FIG. 27, in the case of TPN, the VTP2 value is 122 in the case of the light condition during standing of "white light," 89 in the case of "green light," and 118 in the case of "red light." The VCP2 value is 47 in the case of the light condition during standing of "white light," 78 in the case of "green light," and 44 in the case of "red light." The VCP1 value is 144 in the case of the light condition during standing of "white light," 112 in the case of "green light," and 171 in the case of "red light." These results show that for TPN, the variation rates of all assay values of VCP1, VCP2, and VTP2 drop and the biological growth inhibition factor detection sensitivity is lowered when the light condition during standing is set to "green light."

As shown in the graph (b) of FIG. 27, in the case of inorganic mercury, the VTP2 value is 117 in the case of the light condition during standing of "white light," 113 in the case of "green light," and 114 in the case of "red light." The VCP2 value is 77 in the case of the light condition during standing of "white light," 78 in the case of "green light," and 77 in the case of "red light." The VCP1 value is 103 in the case of the light condition during standing of "white light," 96 in the case of "green light," and 98 in the case of "red light." Thus, for inorganic mercury, it can be seen that there are no large differences in the variation rates of the assay values of CP1, CP2, and TP2 according to the light conditions during standing.

From the above results, it can be understood that the actions of the biological growth inhibition factors in an aqueous solution sample vary according to the light conditions among the standing conditions, and these variations differ according to each biological growth inhibition factor, while there are biological growth inhibition factors that increase in influence under specific optical wavelength conditions as well as inhibition factors that are not influenced by light conditions.

Thus, by evaluating comparison values upon changing the light conditions variously and placing test measurement solutions, obtained from the same aqueous solution sample, under different light conditions and comparing the measurement results, qualitative information concerning the biological growth inhibition factors can be obtained. For example, as shown in FIG. 27(a), in the case of TPN, the variations of VCP1, VCP2, and VTP2 are lessened under green light as compared under white light or red light. This can be made note of to enable distinction from other biological growth inhibition factors.

Though preferred examples of this invention shall now be described in further detail, this invention is not restricted to these examples.

EXAMPLE 1

Figure 28:
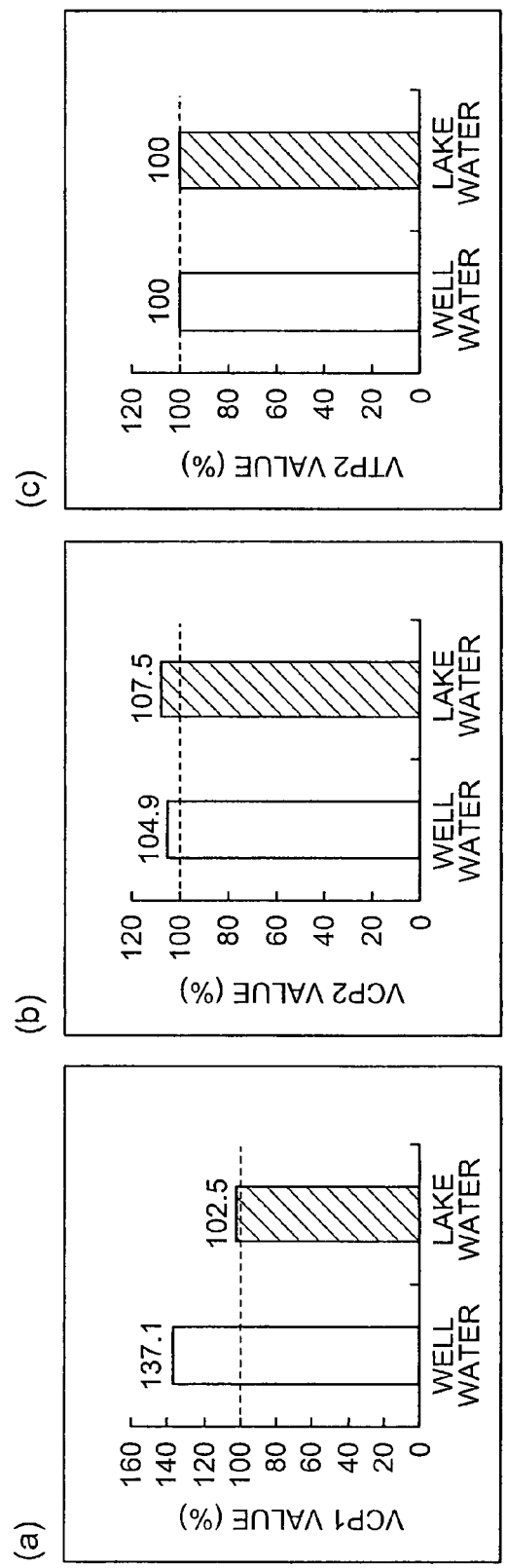
FIG. 28 shows (a) a graph of comparison values VCP1 computed in Example 1, (b) a graph of comparison values VCP2 computed in Example 1, and (c) a graph of comparison values VTP2 computed in Example 1.

Using aqueous solutions obtained from well water and lake water as aqueous solution samples to be assayed and using distilled water as a standard sample, comparison values were computed for the standard measurement conditions described above. The computation results of the comparison values in this Example are shown in FIG. 28. In FIG. 28, graph (a) is a graph of the VCP1 values computed for the well water and the lake water, graph (b) is a graph of the VCP2 values computed similarly, and graph (c) is a graph of the VTP2 values computed similarly.

As shown in FIG. 28, whereas the VCP1 value increased to 137.1% with the "well water," a significant variation was not seen with the "lake water." Significant variations were not seen in the VCP2 values and the VTP2 values. Furthermore, as a result of sampling the well water 4 times within 12 days at the same location, VCP1 values of approximately 120 to 140% were obtained in substantially the same manner.

In regard to the results of the present Example, a hydrophobic herbicide, such as DCMU or atrazine, of an ultralow concentration level of no more than 0.5 ppb can be cited as a known chemical substance that can be considered to be the biological growth inhibition factor for which just the VCP1 value becomes approximately 120 to 140%. The well water used in the test was thus presumed to contain a hydrophobic chemical substance based agricultural chemical similar to DCMU or atrazine.

EXAMPLE 2

Aqueous solutions, respectively containing the well water and the distilled water of Example 1, and an aqueous solution, containing DCMU at a concentration of 0.1 ppb, were used as aqueous solution samples to be assayed, and comparison values were computed in the same manner as in Example 1 for the standard measurement conditions. DCMU is a known hydrophobic, organic-based herbicide and is similar to the well water of Example 1 in terms of the characteristics of the assay value variations.

The respective aqueous solutions of well water, distilled water, and DCMU were also subject to adsorption treatment, and VCP1 values were computed for the adsorbed aqueous solutions. For adsorption, activated carbon, which was dried after washing with water filtered through a high-density filter (water filtered through mili-Q, made by Millipore Corp.), was used. After adding 0.8 g of the activated carbon to 5 ml of each of the aqueous solutions of distilled water, well water, and 0.1 ppb concentration DCMU, each aqueous solution was infiltrated slowly for 1 hour. The filtrates obtained after respectively filtering the three solutions through a 0.45 μm filter were then subject to measurement of the delayed fluorescence amount.

Figure 29:
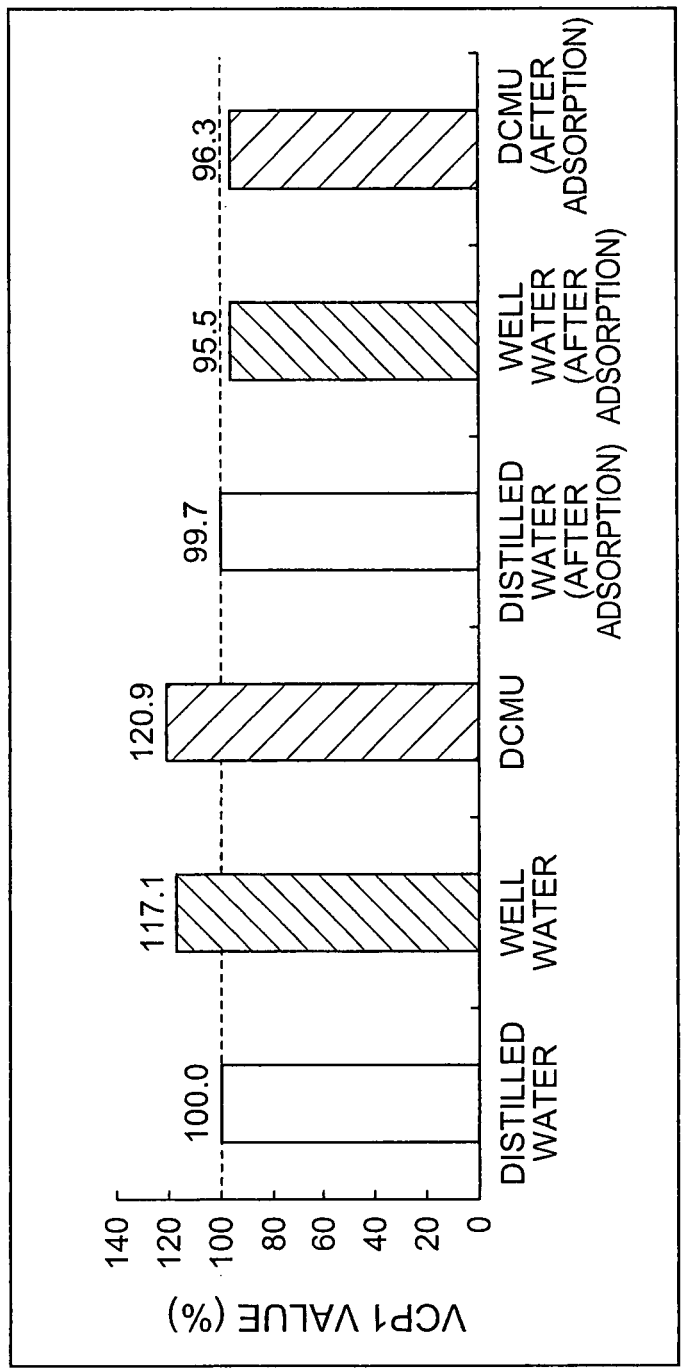
FIG. 29 is a graph of comparison values VCP1 computed in Example 2.

FIG. 29 shows the VCP1 value computation results of this Example. The VCP1 values computed for each of the aqueous solution samples of distilled water, well water, and DCMU and the VCP1 values computed for the respective aqueous solution samples subject to the adsorption treatment are shown in FIG. 29. As shown in FIG. 29, with respect to the result obtained from the distilled water, the VCP1 value was 117.1 with the "well water," and 120.9 with the "DCMU," thus indicating that the variation of CP1 obtained from well water is substantially equivalent to the variation obtained from 0.1 ppb concentration DCMU.

Also, with respect to the VCP1 value of 100 of the distilled water before adsorption ("distilled water"), the VCP1 value of the distilled water after the activated carbon adsorption treatment ("distilled water (after adsorption)") was 99.7 and it was thus assayed that the activated carbon adsorption treatment hardly affected the variation of VCP1. For "well water" and "DCMU," which have increased VCP1 values before the activated carbon adsorption treatment, the VCP1 values after the activated carbon adsorption treatment were 95.5 for "well water (after adsorption)" and 96.3 for "DCMU (after adsorption) and were thus equivalent to those of "distilled water" and "distilled water (after adsorption)." From these results, it was assayed that a substance similar to DCMU or other hydrophobic organic substance is contained in the well water.

The toxic substance assay method and the toxic substance assay kit according to this invention are not restricted to the above-described embodiments and examples, and various modifications are possible. For example, in regard to the photosynthetic sample that is mixed with the aqueous solution sample, a photosynthetic sample that has a photosynthesis function and can emit delayed fluorescence can be used in general as described above.

As such a photosynthetic sample, at least one type of photosynthetic sample, selected from the group consisting of halotolerant algae, alkali-tolerant algae, and acid-tolerant algae, is preferably used. Here, halotolerant algae refers to algae that can grow under a high salinity environment, such as salt water, seawater, etc. Alkali-tolerant algae and acid-tolerant algae refer to algae that can grow under extreme pH environments. *Spirulina* can be cited as an example of such a photosynthetic sample.

That is, when *Spirulina* or *Dunaliella*, which are known as halotolerant algae, *Spirulina* with alkali resistance, *Euglena* with acid resistance, or other algae growing in the ocean or a saltwater lake or algae that can tolerate a high salinity environment or an alkaline (high pH) or acidic (low pH) environment is used as the photosynthetic sample, the following merits arise in comparison to cases where freshwater algae, etc., are used to measure a freshwater sample of lower salt concentration than that of an environment suited for the algae.

As an example, a case of using *Spirulina*, which is an algae that can tolerate highly saline or alkaline environments, shall be described. *Spirulina* is a blue-green algae that grows in both saltwater lakes, which are environments of high salinity, and in freshwater lakes, which are environments of low salinity. Thus, by using *Spirulina*, delayed fluorescence can be measured in environments of both a high salinity medium (SOT medium), corresponding to a saltwater lake environment, and a low salinity medium (MA medium), corresponding to a freshwater lake environment.

Generally, aqueous solution samples that are to be samples are sampled from various environments, such as river or lake water, groundwater, soil-extracted water, etc. The salt concentrations of the samples are thus not uniform and, as a result, may not be uniform in pH and other elements that are important in terms of the growing environment of algae. For this, the method of mixing an adjusting solution with the aqueous solution sample to be tested to adjust the salt concentration and the pH and thereafter mixing with the photosynthetic sample can be used. In this case, by adjusting the aqueous solution sample to be a high salinity medium, the pH, etc., can be adjusted far more readily in comparison to a low salinity medium.

FIG. 30 is a table of adjustment examples of adjusting aqueous solution samples using a high salinity medium and a low salinity medium. Here, lake water, well water, tap water, and distilled water are used as the aqueous solution samples. In these adjustment examples, the pHs of the raw waters are 7.44 for the lake water, 6.03 for the well water, 7.07 for the tap water, and 5.46 for the distilled water, and the standard deviation among samples was 0.91.

Meanwhile, upon adjustment with a high salinity medium of 5 times concentration as the adjusting solution, the pHs became 9.68 for the lake water, 9.71 for the well water, 9.72 for the tap water, and 9.69 for the distilled water. The standard deviation in this case was 0.02 and the pH differences due to differences of the aqueous solution samples were thus improved in comparison to the raw waters. Meanwhile, upon adjustment with a low salinity medium of 5 times concentration as the adjusting solution, the pHs became 8.13 for the lake water, 7.77 for the well water, 8.14 for the tap water, and 8.29 for the distilled water. The standard deviation in this case was 0.22 and though an improvement was made with respect to the raw waters, the results were poor in comparison to the case of using the high salinity medium.

Even for general salt concentrations, fluctuation of the salt concentration in raw water can be improved more readily with a high salinity medium, which adjusts at a high salt concentration with respect to a freshwater environment, than with a low salinity medium. The use of an algae, which inhabits the ocean or saltwater lake, or other algae, which can tolerate a high salt concentration or an alkaline or acidic environment, as the photosynthetic sample thus provides a merit, in comparison to the use of freshwater algae, in terms of improving fluctuations of the pH, salt concentration, etc., of raw water in measuring a freshwater sample, etc., of lower salt concentration than that of an environment suited to such algae.

The solution to be subject to measurement of the delayed fluorescence is preferably homogenized before measurement of the light amount of the delayed fluorescence. If the photosynthetic sample in a measurement solution settles or floats with the elapse of time, the density of the photosynthetic sample within the view field of the photodetector changes and the measured value of the emitted light amount changes. The measurement precision may thus decrease with the elapse of time during the standing period of predetermined time or during measurement. Meanwhile, by homogenizing the solution, toxic substance assay of low error is enabled. For such solution homogenization, the use of a stabilizer for homogenizing the distribution density of the photosynthetic sample is preferable. The assay kit used for toxic substance assay is preferably equipped with a stabilizer for homogenizing the distribution density of the photosynthetic sample. As such a stabilizer, for example, a specific gravity adjusting agent or a thickening agent (gelling agent, etc.) may be used as described above.

Figure 31:
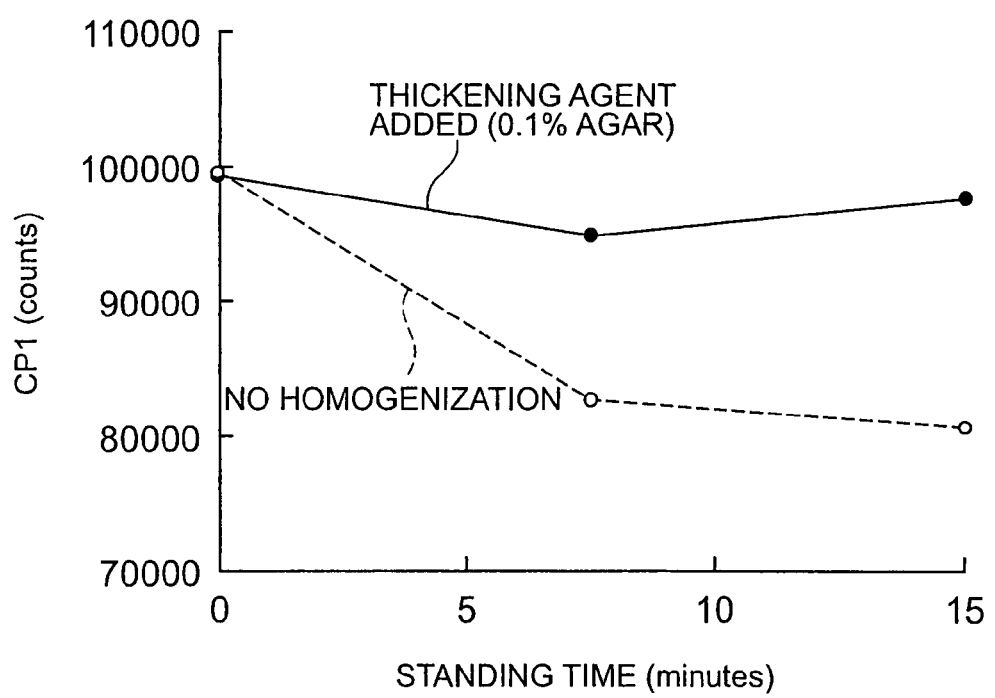
FIG. 31 is a graph of variations of delayed fluorescence amount with respect to standing time under a condition of no homogenization of solution and under addition of a thickening agent.

FIG. 31 is a graph of variations of delayed fluorescence amount with respect to standing time under a condition of no homogenization of solution and under addition of a thickening agent. Here, the blue-green algae, *Spirulina* (*Spirulina platensis*), is used as the photosynthetic sample, and the light amounts of delayed fluorescence were measured for different standing times under the same conditions as the standard measurement conditions described in relation to FIG. 5.

In regard to the addition of a thickening agent, "No homogenization" indicates the measurement results of using a measurement solution adjusted without the addition of agar as a gelling agent that corresponds to being a thickening agent, and "Thickening agent added" indicates the measurement results of using a measurement solution, with which agar was added as the thickening agent to an amount of 0.1 weight % with respect to the entirety. Measurements were made in accordance with the elapse of standing times from immediately after (0 minutes from) solution preparation to 15 minutes after solution preparation, and as the delayed fluorescence amount, CP1, which is the integrated delayed fluorescence amount from 0.1 seconds to 0.5 seconds after the end of light illumination, was determined.

As shown in FIG. 31, with the "No homogenization" graph, for the case of not adding a thickening agent, CP1 decreases with the elapse of the standing time. This is due to the settling or floating of the photosynthetic sample with the elapse of time. On the other hand, with the "Thickening agent added" graph, a large change is not seen in the measured value of CP1 even after the elapse of time. It can thus be understood that use of the measurement solution in measurement upon taking measures to homogenize the photosynthetic sample is effective for improving the measurement precision.

Such a thickening agent is preferably added in a condition that does not inhibit or disturb the measurement of light emission from the photosynthetic sample and enables measurement of weak light emission. Specifically, the use of a thickening agent that does not emit fluorescence or phosphorescence at the concentration enabling homogenization of the photosynthetic sample, is transparent, and does not absorb the light emitted from the photosynthetic sample is preferable. As examples of such a thickening agent, agar or agarose at low concentrations, or methyl cellulose solution may be used. Also, as a means of homogenizing the photosynthetic sample before measurement, the settling or floating of the photosynthetic sample may be restrained in the measurement solution by a microscopic network or lattice structure, or the homogeneity may be maintained by stirring from the exterior, in addition to the method of adding the thickening agent.

Also, the light amount of delayed fluorescence etc. is preferably corrected, etc., as necessary for measurement errors that arise due to concentration differences of the photosynthetic sample in the measurement solution. That is, due to the use of living cells, intracellular organelles, membrane protein complexes, etc., as the photosynthetic sample to be used in measurements, quantitative changes may arise due to increase by cellular growth or cell division or decrease by death or decomposition during manipulation or storage of the sample. Also, even if there are no quantitative changes, qualitative changes, such as change of the delayed fluorescence emission ability, change of characteristics of the temporal variation of the light amount, etc., may occur.

Because such changes become errors in the measurement evaluation, it is effective to employ an evaluation method of evaluating whether or not changes are occurring in the photosynthetic sample used, before measurement. By detecting quantitative changes and qualitative changes of the photosynthetic sample, the precision of the measurement results is controlled. When an abnormality of the photosynthetic sample is detected by such an evaluation method, it can be judged whether the abnormality is within a tolerable range and methods, such as issuing an alarm to a measurer as necessary, can be employed.

Examples of the above-described photosynthetic sample evaluation method include the following methods (1) to (3). (1) Whether the density of the photosynthetic sample is within a range of densities in a proportional relationship with the light amount of delayed fluorescence is evaluated. Such an evaluation can be made using, for example, a calibration curve prepared from densities of the photosynthetic sample and light amounts of delayed fluorescence. (2) Whether or not the light amount of delayed fluorescence with respect to the density of the photosynthetic sample has changed in comparison to exemplary data that serve as an evaluation standard is judged. This evaluation is made, for example, by judging whether or not correlation within a certain error range is obtained with respect to a relational expression of the amount of light emitted per density of photosynthetic sample indicated by a calibration curve prepared from densities of the photosynthetic sample and light amounts of delayed fluorescence. (3) Whether or not the temporal variation of the light amount of delayed fluorescence has changed in comparison to exemplary data that serve as an evaluation standard is judged. For example, differences with respect to the temporal variation of light amount of the exemplary data, the light amount of a characteristic point or the point in time at which a characteristic point appears in the temporal variation of the light amount of delayed fluorescence, the slope of light amount variation between two characteristic points, the slope of light amount variation within a specific time range, etc., can be used for the evaluation.

In the above-described evaluation of the photosynthetic sample, data on the photosynthetic sample, such as the absorbance, light scattering amount, delayed fluorescence light amount, temporal variations of such data, are used as the exemplary data. As such exemplary data and data indicating tolerance ranges, data stored in advance in a measuring device or analyzing device, data recorded during preparation of the photosynthetic sample, etc., may be used. Measurement results of a standard measurement solution, etc., can be estimated from the results of performing the same evaluation on the photosynthetic sample before mixing with the aqueous solution sample. The same data mentioned above may be used in such cases as well.

Preferably, when a change of the photosynthetic sample is detected by the evaluation of the photosynthetic sample, correction of measurement is made as necessary. As an example of such a correction method, if the change that is occurring in the photosynthetic sample is a quantitative change and the density of the photosynthetic sample is judged to be within the range of densities that are in a proportional relationship with the light amount of delayed fluorescence by the evaluation method of (1) described above, measurement results using photosynthetic samples that differ in density can be compared by normalizing the light amount of delayed fluorescence by the density of the photosynthetic sample in each measurement result. As a normalization method to be employed in such a case, there is, for example, the method of dividing the light amount of delayed fluorescence by the density of the photosynthetic sample.

The toxic substance assay method according to this invention shall now be described further.

The above-described embodiment is used to describe a toxic substance assay method that mainly includes: (1) a first step of mixing a photosynthetic sample with an aqueous solution sample to prepare a test measurement solution, letting the test measurement solution stand for a predetermined standing time, and then after illuminating light onto the test measurement solution for a predetermined illumination time, measuring the light amount of the delayed fluorescence that is emitted; (2) a second step of mixing the photosynthetic sample with a standard sample, in which a toxic substance is not present, to prepare a standard measurement solution, letting the standard measurement solution stand for the predetermined standing time, and then after illuminating light onto the standard measurement solution for the predetermined illumination time, measuring the light amount of the delayed fluorescence that is emitted; and (3) a third step of computing assay values based on the light amounts of delayed fluorescence, respectively obtained in the first step and the second step, and determining a comparison value of the assay values to assay the toxic substance present in the aqueous solution sample.

Generally, such a toxic substance assay method can be arranged from: (1) a first step of mixing a photosynthetic sample with an aqueous solution sample to prepare a test measurement solution, letting the test measurement solution stand for a predetermined standing time, and then after illuminating light, onto the test measurement solution for a predetermined illumination time, measuring the light amount of the delayed fluorescence that is emitted; (2) a second step of letting a comparison measurement solution, prepared by mixing the photosynthetic sample with a comparison sample, stand for the predetermined standing time, and then after illuminating light onto the comparison measurement solution for the predetermined illumination time, measuring the light amount of the delayed fluorescence that is emitted to thereby prepare a comparison measurement result; and (3) a third step of computing assay values based on the light amounts of delayed fluorescence, respectively obtained in the first step and the second step, and determining a comparison value of the assay values to assay the toxic substance present in the aqueous solution sample.

Also, as described above, in such an assay method, the assay values are preferably elapsed times of characteristic points in temporal variations of the light amounts of delayed fluorescence acquired in the first step and the second step. Or, the assay values are preferably the temporal variations of the delayed fluorescence light amounts acquired in the first step and the second step, and the comparison value is a value obtained by determining a difference of the temporal variations.

Here, in regard to the comparison sample and comparison measurement result used in the second step, any of various comparison samples and comparison measurement results may be used. For example, a method may be employed in which, in the second step, a standard sample to be compared is used as the comparison sample, a standard measurement solution that is the comparison measurement solution is prepared by mixing the photosynthetic sample with the standard sample, the standard measurement solution is left to stand for the predetermined standing time, and then after illuminating light onto the standard measurement solution for the predetermined illumination time, the light amount of the delayed fluorescence that is emitted is measured to acquire the comparison measurement result. In this case, a sample in which a toxic substance is practically not present is preferably used as the standard sample as was described above in relation to FIG. 3.

Or, in the second step, a method may be employed in which another aqueous solution sample is used as the comparison sample and a measurement result, acquired on another test measurement solution that is a comparison measurement solution prepared by mixing the aqueous solution sample with the photosynthetic sample, is prepared as the comparison measurement result. In this case, a previous measurement result may be used as the comparison measurement result.

Also, in regard to the acquisition of the comparison measurement result in the second step, a method may be employed wherein the comparison measurement result is prepared by performing measurement of the light amount of delayed fluorescence on the comparison measurement solution in the same manner as in the first step. Or, a method may be employed wherein, in the second step, a measurement result that is acquired in advance for the comparison measurement solution is used as the comparison measurement result. In this case, the comparison measurement result that is acquired in advance is preferably stored in a memory, etc., and used upon being read out as data as necessary. Various modifications are thus possible regarding to the comparison sample, comparison measurement solution, method of acquiring the comparison measurement result, etc., used in the second step.

(Continuous Toxic Substance Assay Method)

A continuous toxic substance assay method (monitoring method) using the method according to this invention shall now be described. By using such an assay method, aqueous solution samples taken from a river, groundwater, etc., can be measured in a continuous manner and changes of toxicity can be monitored.

Figure 32:
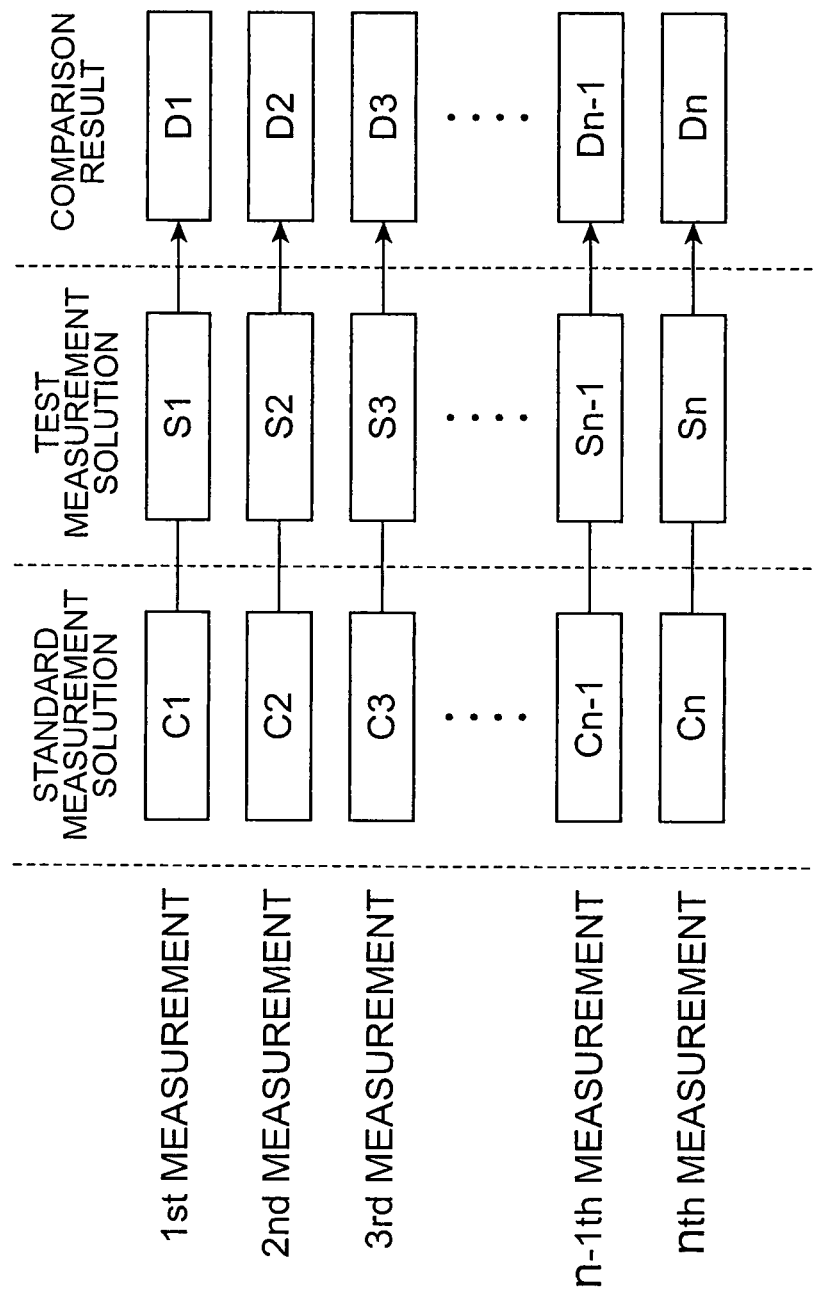
FIG. 32 is a schematic view of an example of a continuous toxic substance assay method.

FIG. 32 is a schematic view of an example of a continuous toxic substance assay method. In this assay method, firstly as first measurements, measurement of a standard measurement solution and measurement of a test measurement solution of an aqueous solution sample of water sampled from a river, etc., are made in accordance with the ordinary procedures. Then, these measurement results are compared to assay toxic substances contained in the river water. In this process, a measurement result C1 of the standard measurement solution, a measurement result S1 of the test measurement solution, and an aqueous solution sample toxicity assay result D1 corresponding to the comparison result of the measurement results are recorded.

Then, after the elapse of a predetermined time set as a measurement time interval, measurement of the standard measurement solution and measurement of a test measurement solution of an aqueous solution sample of newly sampled river water are made as second measurements, these results are compared, and a measurement result C2 of the standard measurement solution, a measurement result S2 of the test measurement solution, and a toxicity assay result D2 are recorded.

Measurements are thereafter made in the same manner at each elapse of the predetermined time, and, for example, in an n-th measurement, a measurement result Cn of the standard measurement solution, a measurement result Sn of the test measurement solution, and a toxicity assay result Dn are recorded. By comparing these recorded aqueous solution sample toxic assay results D1, D2, . . . , Dn in a continuous manner, changes in contamination by toxic substances in a river, etc., can be monitored.

Figure 33:
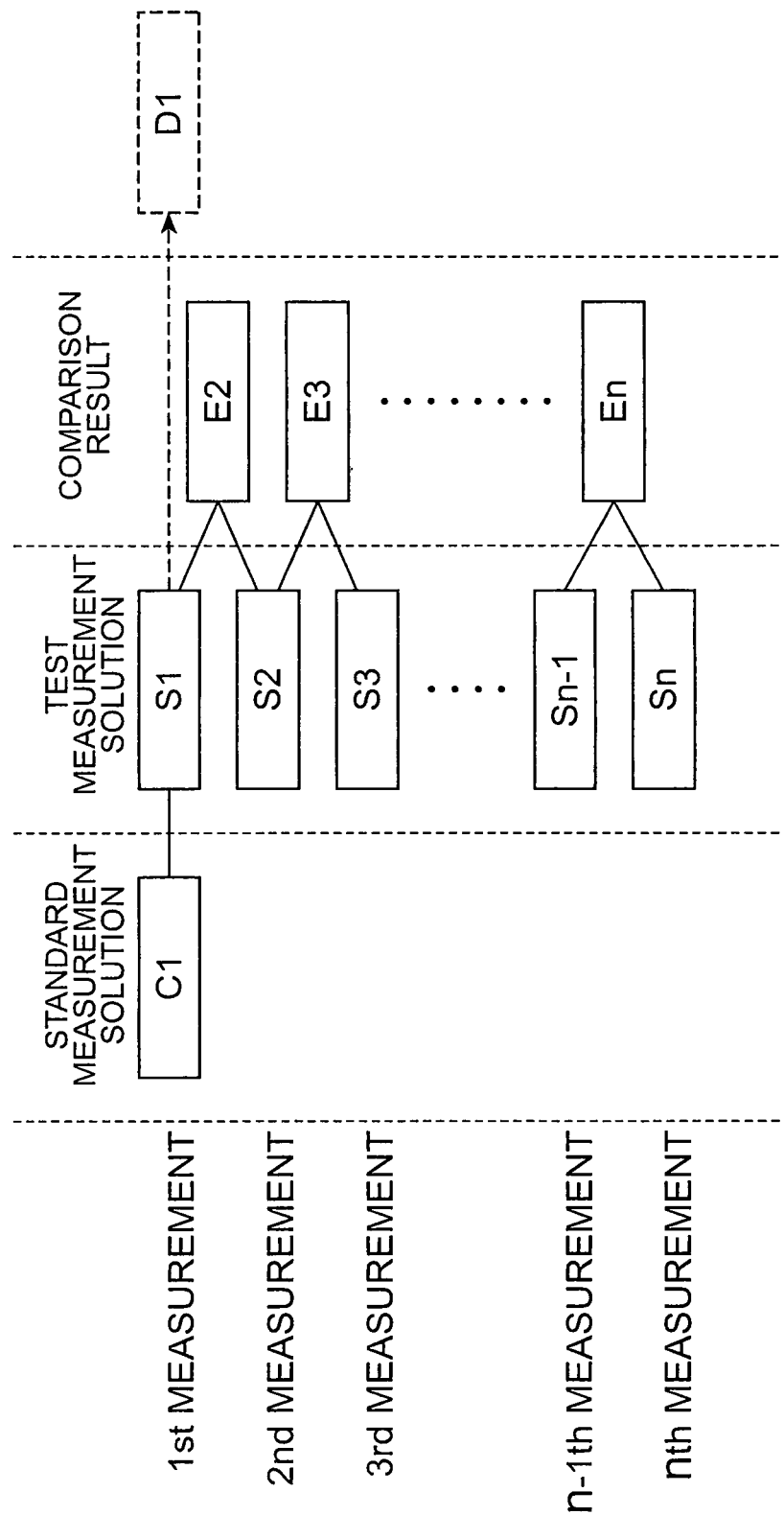
FIG. 33 is a schematic view of another example of a continuous toxic substance assay method.

FIG. 33 is a schematic view of another example of a continuous toxic substance assay method. In this assay method, the first measurements are made in the same manner as described above, and measurement result C1 of the standard measurement solution and measurement result S1 of the test measurement solution are recorded. Aqueous solution sample toxicity assay result D1 corresponding to the comparison result of the measurement results is also recorded as necessary.

Then, after the elapse of the predetermined time, just a measurement of a test measurement solution of an aqueous solution sample of newly sampled river water is made as the second measurement, and measurement result S2 is recorded. Here, the measurement result S2 of the test measurement solution of the second measurement is compared with the measurement result S1 of the test measurement solution of the first measurement, and a toxicity assay result E2 for the aqueous solution sample, corresponding to the comparison result of the measurement results, are recorded. This assay result E2 indicates, in a simple manner, how much the toxicity of the river water, etc., that is to be the aqueous solution sample, has changed between the first measurement and the second measurement.

Measurements are thereafter made in the same manner at each elapse of the predetermined time, and, for example, in an n-th measurement, a measurement result Sn of the test measurement solution and a toxicity assay result En, corresponding to the comparison result of measurement result Sn with measurement result Sn−1 of the (n−1)-th measurement, are recorded. By comparing these recorded aqueous solution sample toxic assay results E2, E3, . . . , En in a continuous manner, changes in contamination by toxic substances in a river, etc., can be monitored in a simplified manner.

In a case where toxic substance assay is performed in a continuous manner by changing the time at which measurement is made as in the assay methods shown in FIGS. 32 and 33, changes may occur in the photosynthetic sample due to the elapse of time between the first measurement and the second measurement onward. Such changes of the photosynthetic sample include quantitative changes, such as a change of density of the photosynthetic sample due to degradation, decomposition, death, proliferation, etc., of the photosynthetic sample, and qualitative changes, such as a change in the elapsed time of a characteristic point in the temporal variation of the light amount of delayed fluorescence or a change in the light amount of the delayed fluorescence. For such changes of the photosynthetic sample, the following corrections can be made after measuring the light amount of delayed fluorescence and measuring the cell density of the photosynthetic sample.

First, if a quantitative change in the density of the photosynthetic sample occurs and it has been determined in advance that, for the photosynthetic sample used in the measurements, the cell density and the light amount of delayed fluorescence are in a range in which these are in a proportional relationship, a correction can be made based on the cell density of the photosynthetic sample measured by absorbance or light scattering amount, etc.

As a specific correction method, for example, in the first measurement, the cell density of the sample is measured along with the light amount of delayed fluorescence from the measurement solution. The cell density of the sample is measured along with the light amount of delayed fluorescence from the measurement solution in the second measurement as well. Here, by performing a correction of dividing the light amount of delayed fluorescence by the cell density in each of the measurement results of the first measurement and second measurement, even if the cell density of the photosynthetic sample changes between the first measurement and the second measurement, the results of the two measurements can be compared.

If a qualitative change in the elapsed time of a characteristic point in the temporal variation of the light amount of delayed fluorescence or in the light amount of delayed fluorescence occurs and it has been determined in advance that, for the photosynthetic sample used in the measurements, the temporal variation of the light amount of delayed fluorescence is within a tolerable range in comparison to exemplary data, a correction can be made based on a positional relationship of the characteristic points, etc.

Figure 34:
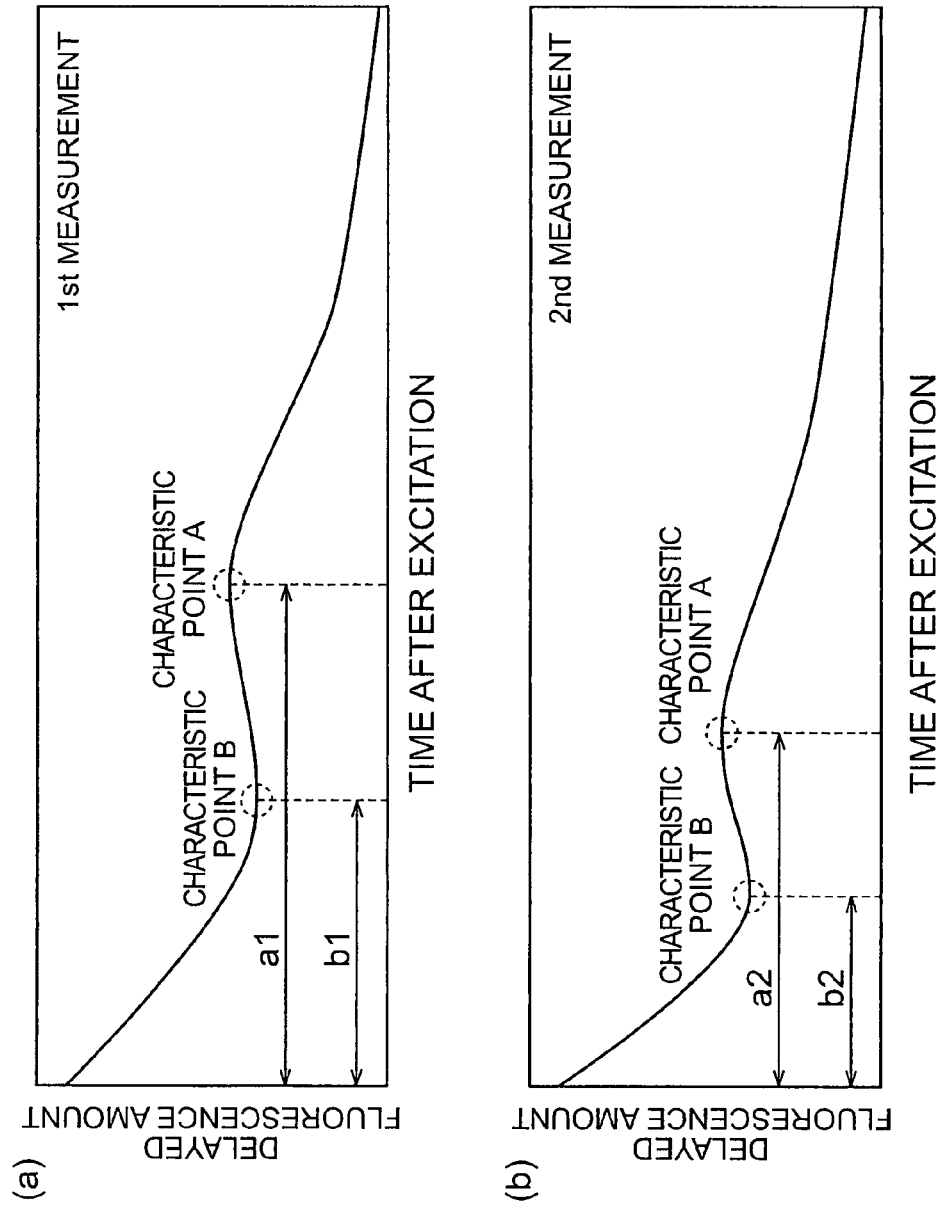
FIG. 34 shows diagrams of examples of temporal variations of light amounts of delayed fluorescence.

A specific example of a correction method shall now be described with reference to FIG. 34. FIG. 34 shows diagrams of examples of temporal variations of light amounts of delayed fluorescence, with graph (a) being a graph indicating the temporal variation of the delayed fluorescence amount acquired in a first measurement, and graph (b) being a graph indicating the temporal variation of the delayed fluorescence amount acquired in a second measurement.

For these temporal variations of delayed fluorescence amount, for example, elapsed times a1 and b1 are determined for characteristic points A and B of the first measurement shown in the graph (a). Likewise, elapsed times a2 and b2 are determined for characteristic points A and B of the second measurement shown in the graph (b). For these measurement results, the ratio of elapsed time b1 with respect to a1, (b1/a1), is determined from the results of the first measurement. Likewise, the ratio of elapsed time b2 with respect to a2, (b2/a2), is determined from the results of the second measurement. By then comparing these ratios, (b1/a1) and (b2/a2), a correction based on the positional relationship of the characteristic points can be made.

(Curve Value Analysis Method)

In regard to the assay values and the comparison values used in toxic substance assay, for example, the temporal variations of the light amounts of delayed fluorescence acquired in the first step and the second step may be used as assay values, and the value obtained by determining a difference of the temporal variations may be used as a comparison value as described above. In the embodiment described above, the Curve values, obtained by determining differences of the respective temporal variations of the light amounts of delayed fluorescence obtained from the test measurement solution and the standard measurement solution, are cited as such comparison values. In regard to methods of analyzing the Curve values, various analysis methods may be used according to the specific measurement results acquired for the test measurement solution and the standard measurement solution.

In regard to the Curve values, corresponding to the differences of the temporal variations of the light amounts of delayed fluorescence, considerations can be made separately for cases where characteristic points are present in the temporal variations of the light amounts of delayed fluorescence that are the measurement results and cases where characteristic points are not present.

In a case where characteristic points are present in the delayed fluorescence decay curve (see FIG. 5) that indicates the temporal variation of the light amount of delayed fluorescence, an evaluation can be made by noting the amounts of emitted light, the elapsed times, etc., at the characteristic points as described above. If the Curve values are to be used, preferably the Curve values, determined by making note of the interval between two characteristic points or the interval between the measurement starting point and a characteristic point, are used as comparison values for carrying out the assay. Or, the Curve values may be determined for the entirety or a predetermined range without consideration of characteristic points.

Meanwhile, if characteristic points are not present in a delayed fluorescence decay curve, the Curve values, determined for the entirety or a predetermined range of the decay curve, may be used as comparison values for carrying out the assay. Here, the Curve value at each measurement point n in a temporal variation of the light amount of delayed fluorescence is determined by: (amount of light emitted from the test measurement solution at measurement point n)−(amount of light emitted from the standard measurement solution at measurement point n).

Generally, as was shown for example in FIG. 5, with the delayed fluorescence emitted from a photosynthetic sample, the amount of emitted light is high in a time range of early post-excitation time and the amount of emitted light decreases by decay in later time ranges. Thus, if the time ranges in which the Curve values are computed differ, the magnitudes of the differences of emitted light amounts differ, and there may be cases where it is difficult to evaluate variations in different time ranges.

In such a case, it is effective to use VCurve values, each being standardized by being determined as a ratio of a Curve value, which is a value obtained by determining a difference of the temporal variations of the light amount of delayed fluorescence acquired for the test measurement solution and the standard measurement solution, with respect to a light amount of delayed fluorescence acquired for the test measurement solution or the standard measurement solution (preferably, a light amount of delayed fluorescence acquired for the standard measurement solution), as the comparison values. The evaluation of variations within different time ranges is thereby facilitated. Here, in a temporal variation of the light amount of delayed fluorescence, the VCurve value at each measurement point n is determined as (Curve value at measurement point n)/(amount of light emitted from the standard measurement solution at measurement point n)×100.

In a case of applying the above-described VCurve values to a delayed fluorescence decay curve in which characteristic points exist, the VCurve values may be determined by making note of the interval between characteristic points or the interval between the measurement starting point and a characteristic point, or the VCurve values may be determined for the entirety or a predetermined range of the decay curve without consideration of characteristic points.

In regard to the presence or non-presence of characteristic points in a delayed fluorescence decay curve, generally, the temporal variation of the light amount of delayed fluorescence acquired in the first step or the second step has characteristic points, and a method may be employed, in which in the third step, the values of the differences of the temporal variations of the light amount of delayed fluorescence, within a predetermined range between one characteristic point and the measurement starting point or another characteristic point, are used as comparison values to assay toxic substances. In a case where there are no characteristic points in temporal variations of the light amount of delayed fluorescence, the values of the differences of the temporal variations of the light amount of delayed fluorescence over the entirety or a predetermined range of the temporal variations may be used as comparison values.

FIG. 35 shows diagrams of examples of methods of computing the Curve values when characteristic points exist in the delayed fluorescence decay curves. In comparing the delayed fluorescence decay curve of a standard measurement solution and the delayed fluorescence decay curve of a test measurement solution, the positions of characteristic points in the decay curves may differ. In such a case, a time range that does not contain the characteristic points is preferably set as the range for computing the Curve values to assay toxic substances while eliminating the effects of the characteristic points.

The graphs (a) to (c) of FIG. 35 show cases of setting the time range for computing Curve values when the delayed fluorescence decay curves of the standard measurement solution and the test measurement solution differ in the positions of characteristic points, with the maxima at 0 seconds after excitation (measurement starting point) and a minima that appears immediately thereafter being the two characteristic points to be noted. The graph (a) of FIG. 35 shows a case where, of the delayed fluorescence decay curves of the standard measurement solution and the test measurement solution, the characteristic point is present only in the decay curve of the standard measurement solution. In this case, the time range, "a," from the measurement starting point to the point of appearance of the minima of the standard measurement solution, is preferably selected as the range for computing the Curve values.

The graph (b) of FIG. 35 shows a case where the minima in the delayed fluorescence decay curve of the test measurement solution appears at an earlier point in time than the minima of the standard measurement solution. In this case, preferably, the time range, "b," from the measurement starting point to the point of appearance of the minima of the standard measurement solution, and time range, "c," from the measurement starting point to the point of appearance of the minima of the test measurement solution, are compared, and the time range "c," which is a time range in common to both curves is selected as the range for computing the Curve values.

The graph (c) of FIG. 35 shows a case where the minima in the delayed fluorescence decay curve of the test measurement solution appears at a later point in time than the minima of the standard measurement solution. In this case, preferably, the time range, "d," from the measurement starting point to the point of appearance of the minima of the standard measurement solution, and time range, "e," from the measurement starting point to the point of appearance of the minima of the test measurement solution, are compared, and the time range "d," which is a time range in common to both curves is selected as the range for computing the Curve values.

Figure 36:
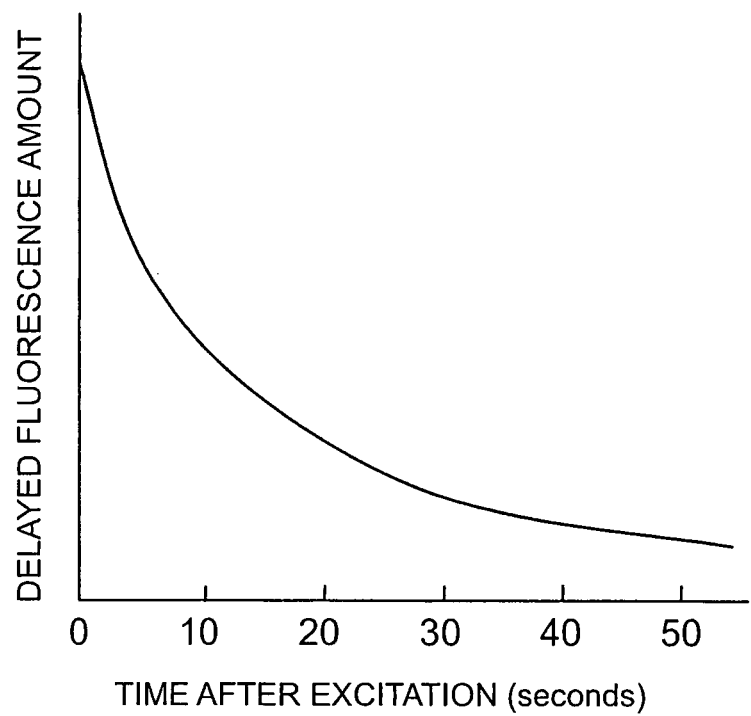
FIG. 36 is a diagram of an example of a method of computing the Curve values when no characteristics points exist in a delayed fluorescence decay curve.

FIG. 36 is a diagram of an example of a method of computing the Curve values when no characteristics points exist in a delayed fluorescence decay curve. Here, a delayed fluorescence decay curve of a standard measurement solution using *Selenastrum capricornutum*, which is a green algae and has been grown by a general method at a light intensity of 50 μmol/m$^2$/s under a white fluorescence lamp, as the photosynthetic sample is shown. Preparation of the sample is carried out in the same manner as in the case of *Spirulina platensis*. Clear characteristic points do not appear in the delayed fluorescence decay curve of the graph of FIG. 36. In such a case, assay using the Curve values is effective because assay that makes note of characteristic points cannot be made.

FIG. 37 shows graphs of the Curve values in cases where (a) the concentration of simazine and (b) the concentration of dichlorophenol are varied. Specifically, graph (a) of FIG. 37 is a graph of the Curve values computed from the measurement results of test measurement solutions exposed to simazine, which is a herbicide, at concentrations of 25, 50, and 100 ppb and the measurement results of the standard measurement solution for a time range of 0.1 seconds to 50 seconds after excitation. Graph (b) is a graph of the Curve values computed from the measurement results of test measurement solutions exposed to dichlorophenol at concentrations of 1, 5, and 10 ppm and the measurement results of the standard measurement solution for a time range of 0.1 seconds to 50 seconds after excitation.

Of these, with the graph (a) that concerns simazine, the Curve values vary according to the simazine exposure concentration and, with an increase in concentration, vary in the positive direction near 0.1 seconds after excitation. Slight variations in the negative direction were also seen from 0.5 seconds after excitation and onward. With the graph (b) concerning dichlorophenol, the Curve values vary according to the dichlorophenol exposure concentration and, with an increase in concentration, vary in the negative direction near 0.2 to 10 seconds after excitation.

The above results show that even when clear characteristic points are not present in the delayed fluorescence decay curve, the effects of toxic substances can be assayed by computing the Curve values. Because the time range in which variations appear and the positive or negative direction of variations differ according to toxic substance, such Curve values are useful for specifying the types, actions, etc., of the detected toxic substances.

FIG. 38 shows graphs of the VCurve values in cases where (a) the concentration of simazine and (b) the concentration of dichlorophenol are varied. Specifically, graph (a) of FIG. 38 is a graph of the VCurve values computed from the measurement results of test measurement solutions exposed to simazine at concentrations of 25, 50, and 100 ppb and the measurement results of the standard measurement solution for a time range of 0.1 seconds to 50 seconds after excitation. Graph (b) is a graph of the VCurve values computed from the measurement results of test measurement solutions exposed to dichlorophenol at concentrations of 1, 5, and 10 ppm and the measurement results of the standard measurement solution for a time range of 0.1 seconds to 50 seconds after excitation. Specifically, in regard to the VCurve values, the examples shown here are those in which the Curve values, corresponding to differences in temporal variations, are standardized as ratios with respect to the emitted light amounts of the standard measurement sample, as described above.

Of these, with the graph (a) that concerns simazine, the VCurve values vary according to the simazine exposure concentration and, with an increase in concentration, vary in the positive direction near 0.1 to 0.3 seconds after excitation. Also, variations in the negative direction were seen over a wide range, from 0.4 seconds to 50 seconds after excitation and centered near 15 seconds. With the graph (b) concerning dichlorophenol, the VCurve values vary according to the dichlorophenol exposure concentration and, with an increase in concentration, vary in the negative direction widely over the entire range (near 0.1 to 50 seconds) of the time after excitation.

The above results show that even when clear characteristic points are not present in the delayed fluorescence decay curve, the effects of toxic substances can be assayed by computing the VCurve values. Because the time range in which variations appear and the positive or negative direction of variations differ according to toxic substance, such VCurve values are useful for specifying the types, actions, etc., of the detected toxic substances. Also, in comparison to Curve values, variations in different time ranges can be compared readily with VCurve values.

(Acclimation Treatment of a Test Measurement Solution)

An acclimation treatment that is performed on a test measurement solution before measurement shall now be described. As mentioned above in relation to the standard measurement conditions of FIG. 5, an acclimation treatment (acclimating step) by preliminary light illumination and standby under total darkness for a predetermined time (dark standby) may be performed to acclimate the photosynthetic sample to the measurement light conditions.

In general, a toxic substance assay method including such an acclimating step is a toxic substance assay method for assaying a toxic substance present in an aqueous solution sample to be tested that preferably includes: (a) a preparing step of mixing the aqueous solution sample with a photosynthetic sample, having a photosynthetic function, to prepare a test measurement solution; (b) a standing step of letting the test measurement solution stand for a predetermined standing time; (c) a measuring step of illuminating light onto the test measurement solution for a predetermined illumination time and thereafter measuring the light amount of delayed fluorescence that is emitted; (d) an assaying step of assaying a toxic substance present in the aqueous solution sample based on the light amount of delayed fluorescence acquired in the measuring step; and (e) an acclimating step, preceding the measuring step and including one of either a dark standby step of subjecting the test measurement solution to a dark standby for a predetermined standby time or a preliminary illuminating step of subjecting the test measurement solution to a preliminary light illumination and to a dark standby for a predetermined standby time.

With such a toxic substance assay method, a plurality of toxic substances can be analyzed qualitatively and quantitatively at high precision at the same time from characteristics obtained from the temporal variation of the light amount of delayed fluorescence emitted from the photosynthetic sample mixed in the aqueous solution sample to be assayed. By performing the assay by measuring the delayed fluorescence light amount, the measurement time can be shortened as a whole. Also, by performing the acclimating step on the test measurement solution before the measuring step, the precision of measurement of the delayed fluorescence and the precision of assay of toxic substances by the measurement result can be improved.

In such a case where the adaptation step is performed before the measuring step, the predetermined standby time in the dark standby step is preferably no less than 30 seconds and no more than 1 hour. Also, preferably in the preliminary illuminating step, the ratio of the preliminary light illumination time to the dark standby time is equal to the ratio of the light illumination time and the dark standby time in the measuring step. Such an acclimating step shall now be described specifically.

The delayed fluorescence that is used to assay toxic substances is a phenomenon in which the light energy absorbed by the photosynthetic sample is re-emitted after being distributed among various chemical reactions. Thus, the history of the photosynthetic sample related to various environmental factors, such as light, temperature, etc., up to the point of measuring the delayed fluorescence (measuring step) may have an important effect on the delayed fluorescence measurement results (see, for example, Non-Patent Document 2). Thus, in order to use the delayed fluorescence measurement results for assay of toxic substances in water quality inspection, etc., the environmental history of the photosynthetic sample is preferably controlled to perform measurement of the delayed fluorescence under conditions of good reproducibility.

Figure 39:
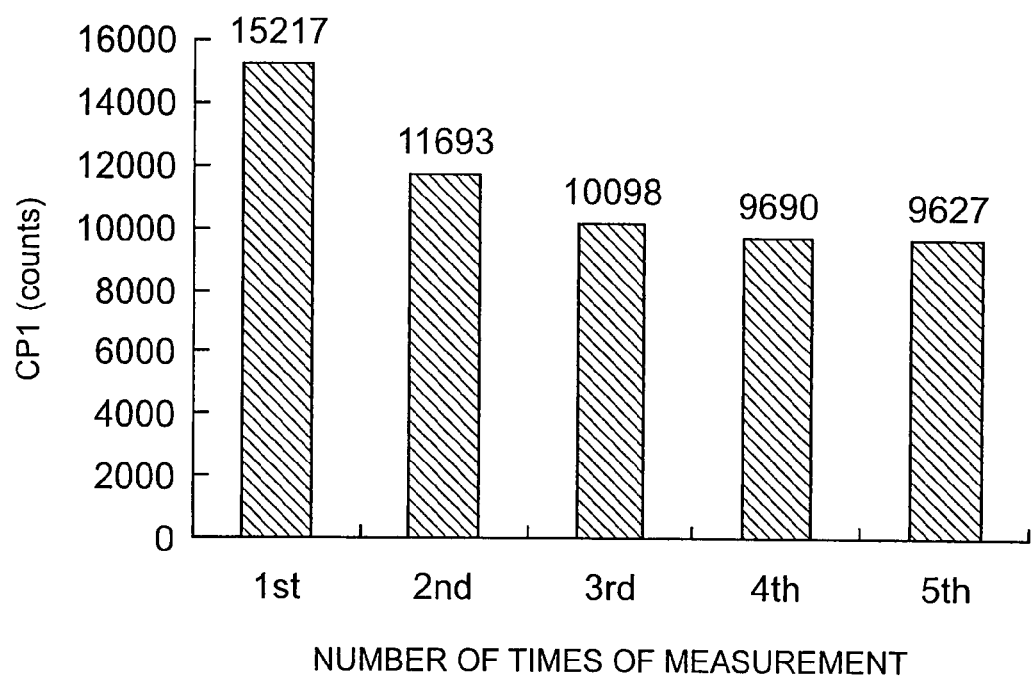
FIG. 39 is a graph of a variation of assay value CP1 with the number of times of measurement of delayed fluorescence.

FIG. 39 is a graph of a variation of CP1 with the number of times of measurement of delayed fluorescence. Here, on a standard measurement solution, which had been left to stand for 15 minutes under a white fluorescent lamp of 5 $\mu mol/m^2/s$ as effective photosynthetic radiation, the light amount of delayed fluorescence was measured under darkness for 60 seconds after 2 seconds of illumination by light of 665 nm and 0.8 $mW/cm^2$ as the measurement conditions. This measurement was repeated 5 times in succession and the CP1 value was determined each time.

As the measurement results, the CP1 value obtained was 15217 in the first measurement, 11693 in the second measurement, 10098 in the third measurement, 9690 in the fourth measurement, and 9627 in the fifth measurement. As indicated by these CP1 values, there is fluctuation of the CP1 value, especially among the results of the first to third measurements. It can also be seen that, by repeating the measurement of delayed fluorescence, the measurements results stabilize at a certain value (for example, the values obtained in the third to fifth measurements) and the reproducibility improves. This indicates that the distribution of light energy inside the photosynthetic sample acclimates from the standing conditions to the measurement conditions.

As can be understood from the above results, when the delayed fluorescence measuring step is performed in continuation to the standing step of letting the measurement solution stand for the predetermined standing time, an adequate reproducibility of delayed fluorescence measurement is not obtained and there is fluctuation of the measurement results. With the example shown in FIG. 39, the measurement results of the first to third measurements do not provide an adequate precision for water quality inspection. Also, it is troublesome to judge from which measurement result an adequate reproducibility is obtained and individual differences among measurers may be reflected in the measurement results as well.

As a result of examining methods of controlling the environmental history of photosynthetic samples in such a case, it was found that by adding an acclimating step of controlling the environmental history of the photosynthetic sample between the standing step and the measuring step, measurement results of good reproducibility are obtained. By carrying out such an adaptation step, for example, the measurement result of the third measurement or later among the measurement results of FIG. 39 can be obtained from the first measurement.

The acclimating step of acclimating the measurement solution to the measurement conditions is achieved by adding, between the standing step and the measuring step, one of either or both of: (1) a dark standby step of subjecting the measurement solution to a dark standby for a predetermined standby time; and (2) a preliminary illuminating step of subjecting the test measurement solution to a preliminary light illumination and to a dark standby for a predetermined standby time.

FIG. 40 is a table of measurement precisions of results of measuring delayed fluorescence three times under various acclimation conditions. Specifically, for each of various acclimation conditions, measurements were made three times in succession and the measurement precision (%) was computed by dividing the standard deviation of the measurements by the average of the three measurements and then multiplying by 100. Each measurement precision shown in FIG. 40 thus expresses how much error a CP1 value obtained in the three measurements contains with respect to the average.

Here, on a standard measurement solution, which had been left to stand for 15 minutes under a white fluorescent lamp of 5 μMol/m$^2$/s as effective photosynthetic radiation, the light amount of delayed fluorescence was measured under darkness for 60 seconds after 2 seconds of illumination by light of 665 nm and 0.8 mW/cm$^2$ as the measurement conditions. This measurement was repeated three times as the main measurements. And before carrying out the main measurements, an acclimation treatment under an acclimation condition (preliminary illumination condition) among the various acclimation conditions is performed, and the measurement precision is determined for the results of the three measurements.

As the acclimating conditions, two seconds of illumination of light of 665 nm and 0.8 mW/cm$^2$, followed by 60 seconds of standby under darkness in the same manner as the procedures of the measurement conditions were performed immediately before the main measurements in the case of "1 time of measurement conditions," and the same procedures were repeated twice in the case of "2 times of measurement conditions." In the case of "1 time of darkness," standby under darkness for the same duration as the measurement conditions was carried out without light illumination, and in the case of "2 times of darkness," this dark standby was repeated twice. In the case of "1 time of illumination," light was illuminated for the same duration as the measurement conditions, in the case of "light 30, darkness 30," illumination of light for 30 seconds was followed by 30 seconds of standby under darkness, in the case of "light 1, darkness 30," illumination of light for 1 second was followed by 30 seconds of standby under darkness, and in the case of "no acclimation," an acclimation treatment was not performed.

As a result, it was found that as acclimation conditions for the measurement solution, the repetition of the same light illumination and dark standby as the measurement conditions once or twice or the repetition of standby under darkness for the same duration as the measurement conditions once or twice without performing light illumination is suitable as the acclimation treatment. With the example shown in FIG. 40, the measurement precisions for "2 times of measurement conditions" and "2 times of darkness," which are the same in the duration of the acclimation conditions, were 3.6 and 4.8, respectively, and the measurement precisions for "1 time of measurement conditions" and "1 time of darkness" were 10.6 and 14.2, respectively. It was found that in comparison to the case of performing acclimation treatment by just standby under darkness, the measurement solution can be acclimated to the measurement environment more effectively by performing the same light illumination and standby under darkness as the measurement conditions.

The above results show that by adding, between the standing step and the measuring step, one of either or both of the above-mentioned dark standby step and preliminary illuminating step, the precision of the delayed fluorescence measurement that is performed subsequently can be improved.

INDUSTRIAL APPLICABILITY

This invention can be used to provide a toxic substance assay method and a toxic substance assay kit that enable a wide range of toxic substances to be analyzed in a short time.

The invention claimed is:

1. A toxic substance assay method of assaying a toxic substance present in an aqueous solution sample containing an unknown toxic substance, the toxic substance assay method comprising:
   a first step comprising:
      mixing a photosynthetic sample, having a photosynthetic function and able to emit delayed fluorescence, with the aqueous solution sample to prepare a test measurement solution,
      letting the test measurement solution stand for a predetermined standing time under white light illumination,
      setting the test measurement solution in a casing in which a light source and a measuring device are housed, the casing having a light blocking property,
      illuminating measurement light from the light source with a single wavelength selected from within a range of 280 nm to 800 nm onto the test measurement solution for a predetermined illumination time, and then putting the test measurement solution under total darkness for a predetermined standby time,
      then, illuminating the measurement light from the light source onto the test measurement solution for the predetermined illumination time,
      measuring with the measuring device in the casing a light amount of a delayed fluorescence that is emitted, and
      transmitting the measured light amount from the measuring device to a computer;
   a second step comprising:
      mixing the photosynthetic sample with a comparison sample containing only known elements in known concentrations to prepare a comparison measurement solution,
      letting the comparison measurement solution stand for the predetermined standing time under white light illumination,
      setting the comparison measurement solution in the casing having the light blocking property,
      illuminating the measurement light from the light source onto the comparison measurement solution for the predetermined illumination time, and then putting the comparison measurement solution under total darkness for the predetermined standby time,
      then, illuminating the measurement light from the light source onto the comparison measurement solution for the predetermined illumination time, measuring with the measuring device in the casing a light amount of the delayed fluorescence that is emitted to thereby prepare a comparison measurement result, and transmitting the measured light amount from the measuring device to the computer;

a third step, implemented by the computer programmed to perform the steps comprising:
i) plotting delayed fluorescence decay curves of temporal variations of the light amount of delayed fluorescence acquired in each of the first step for the test measurement solution and the second step for the comparison measurement solution;
ii) finding a first peak P1 which is a peak of the decay curve that follows from the end of light illumination, and a second peak P2 which appears after the end of light illumination on the delayed fluorescence decay curves in each of the first step for the test measurement solution and the second step for the comparison measurement solution;
iii) computing a delayed fluorescence amount CP1 at the first peak P1, in each of the first step and the second step, as the integrated amount of delayed fluorescence from 0.1 seconds to 0.5 seconds after the end of light illumination;
iv) computing the time TP2 elapsed, in each of the first step and the second step, from the end of light illumination to the point at which the second peak P2 appears;
v) computing a delayed fluorescence amount CP2 at the second peak P2, in each of the first step and the second step, as the integrated amount of delayed fluorescence in +0.5 seconds with respect to the time at which the second peak P2 appears;
vi) computing a first ratio of the value obtained in step iii) for the first step to the value obtained in step iii) for the second step, computing a second ratio of the value obtained in step iv) for the first step to the value obtained in step iv) for the second step, computing a third ratio of the value obtained in step v) for the first step to the value obtained in step v) for the second step; and a fourth step comprising reporting an evaluation of the presence or absence of a toxic substance or toxic substances selected from the group consisting of atrazine, DCMU, paraquat, free cyanide, and TPN, and combinations thereof in the aqueous solution sample using the computed first, second, and third ratios to respective ratios for aqueous solutions containing known toxic substances.

2. The toxic substance assay method according to claim 1, wherein in the second step, a standard sample to be compared with is used as the comparison sample.

3. The toxic substance assay method according to claim 1, wherein in the second step, another aqueous solution sample is used as the comparison sample.

4. The toxic substance assay method according to claim 1, wherein, the second step is performed in advance of the first step.

5. The toxic substance assay method according to claim 1, wherein in the first step and the second step, the test measurement solution and the comparison measurement solution are left to stand for a predetermined standing time with light conditions being varied in each set of test measurement and comparison measurement, and in the third step, a variation of the comparison values according to the light conditions is evaluated.

6. The toxic substance assay method according to claim 1, wherein the densities of the photosynthetic sample in the test measurement solution and in the comparison measurement solution are within a range of densities that are in a proportional relationship with the light amount of delayed fluorescence.

7. The toxic substance assay method according to claim 1, wherein in the first step, the test measurement solution is homogenized before measuring the light amount of delayed fluorescence, and in the second step, the comparison measurement solution is homogenized before measuring the light amount of delayed fluorescence.

8. The toxic substance assay method according to claim 1, wherein the photosynthetic sample includes at least one type of photosynthetic sample, selected from the group consisting of halotolerant algae, alkali-tolerant algae, and acid-tolerant algae.

9. The toxic substance assay method according to claim 8, wherein the photosynthetic sample is *Spirulina*.

* * * * *